(12) United States Patent
Hada et al.

(10) Patent No.: US 8,092,663 B2
(45) Date of Patent: Jan. 10, 2012

(54) GAS SENSOR CONTROL DEVICE

(75) Inventors: Satoshi Hada, Inazawa (JP); Katsuhide Akimoto, Nishio (JP); Shoichiro Emmei, Nagoya (JP); Keigo Mizutani, Okazaki (JP); Shinya Teranishi, Kariya (JP)

(73) Assignee: Denso Corporation, Kariya (JP)

( * ) Notice: Subject to any disclaimer, the term of this patent is extended or adjusted under 35 U.S.C. 154(b) by 522 days.

(21) Appl. No.: 12/388,625

(22) Filed: Feb. 19, 2009

(65) Prior Publication Data
US 2009/0205957 A1 Aug. 20, 2009

(30) Foreign Application Priority Data

Feb. 19, 2008 (JP) ................... 2008-037295
Feb. 19, 2008 (JP) ................... 2008-037296

(51) Int. Cl.
*G01N 27/41* (2006.01)
(52) U.S. Cl. ....... 204/406; 204/425; 73/23.31; 73/23.32
(58) Field of Classification Search ................... 204/406
See application file for complete search history.

(56) References Cited

U.S. PATENT DOCUMENTS

| 5,810,997 | A | 9/1998 | Okazaki et al. |
| 6,164,125 | A | 12/2000 | Kawase et al. |
| 6,383,354 | B1 | 5/2002 | Kurokawa et al. |
| 6,547,955 | B1 | 4/2003 | Hada et al. |
| 6,994,780 | B2 | 2/2006 | Mizutani et al. |
| 7,073,320 | B2 | 7/2006 | Moritsugu et al. |
| 2002/0189942 | A1 | 12/2002 | Niwa et al. |
| 2004/0089545 | A1 | 5/2004 | Kawase et al. |
| 2004/0221641 | A1 | 11/2004 | Moritsugu et al. |
| 2005/0230248 | A1 | 10/2005 | Kawase et al. |
| 2006/0011476 | A1 | 1/2006 | Hada et al. |
| 2007/0284248 | A1* | 12/2007 | Kawase et al. ................ 204/424 |
| 2008/0185289 | A1* | 8/2008 | Matsuoka et al. ............ 204/425 |

FOREIGN PATENT DOCUMENTS

| EP | 1 480 039 | 11/2004 |
| JP | 08-271476 | 10/1996 |
| JP | 09-061397 | 3/1997 |

(Continued)

OTHER PUBLICATIONS

Extended European Search Report dated Sep. 17, 2009, issued in corresponding European Application No. 09153115.2-2204.

*Primary Examiner* — Jeffrey T Barton
*Assistant Examiner* — Louis Rufo
(74) *Attorney, Agent, or Firm* — Nixon & Vanderhye P.C.

(57) ABSTRACT

A gas sensor control device is disclosed as including a sensor cell having a negative terminal, to which a current-voltage converter is connected, and a differential amplifier is connected to the current-voltage converter to provide a current measured result applied to a microcomputer. The current-voltage converter has an opposite-to-sensor terminal to which another differential amplifier is connected. A sensor-side terminal of the current-voltage converter and another differential amplifier is electrically connected to each other via an electric pathway having a sensor-current flow disabling pathway in which a switch circuit is provided. Closing the switch circuit allows a potential difference between both terminals of the current-voltage converter is zeroed. With the switch circuit closed, the microcomputer calculates an element current correcting value, while detecting an electromotive force of the sensor cell based on which a failure is determined.

17 Claims, 38 Drawing Sheets

FOREIGN PATENT DOCUMENTS

| | | |
|---|---|---|
| JP | 11-006815 | 1/1999 |
| JP | 2000-155109 | 6/2000 |
| JP | 2002-372514 | 12/2002 |
| JP | 2004-205488 | 7/2004 |
| JP | 2004-245662 | 9/2004 |
| JP | 2005-326388 | 11/2005 |
| JP | 2006-071429 | 3/2006 |

\* cited by examiner

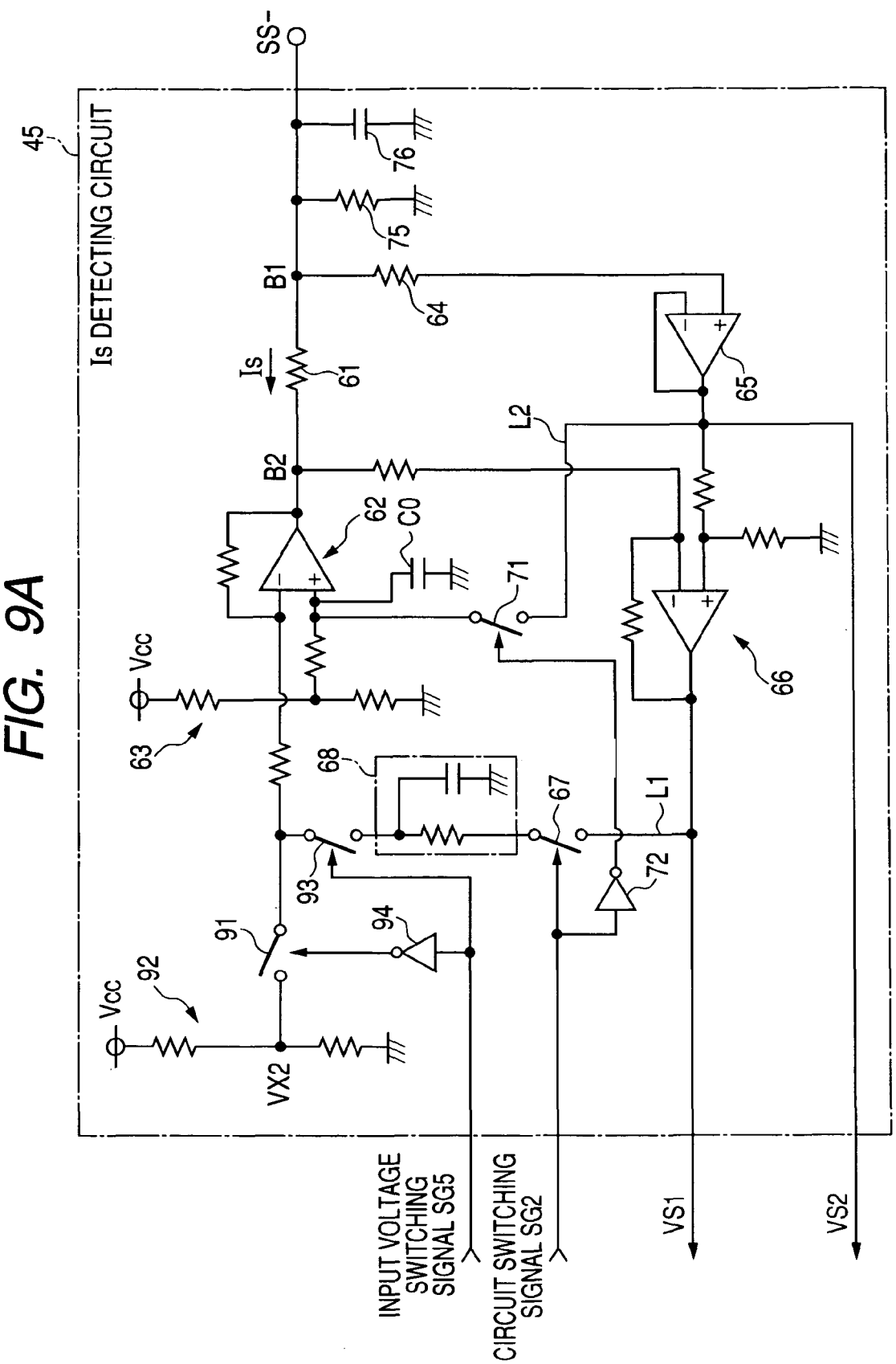

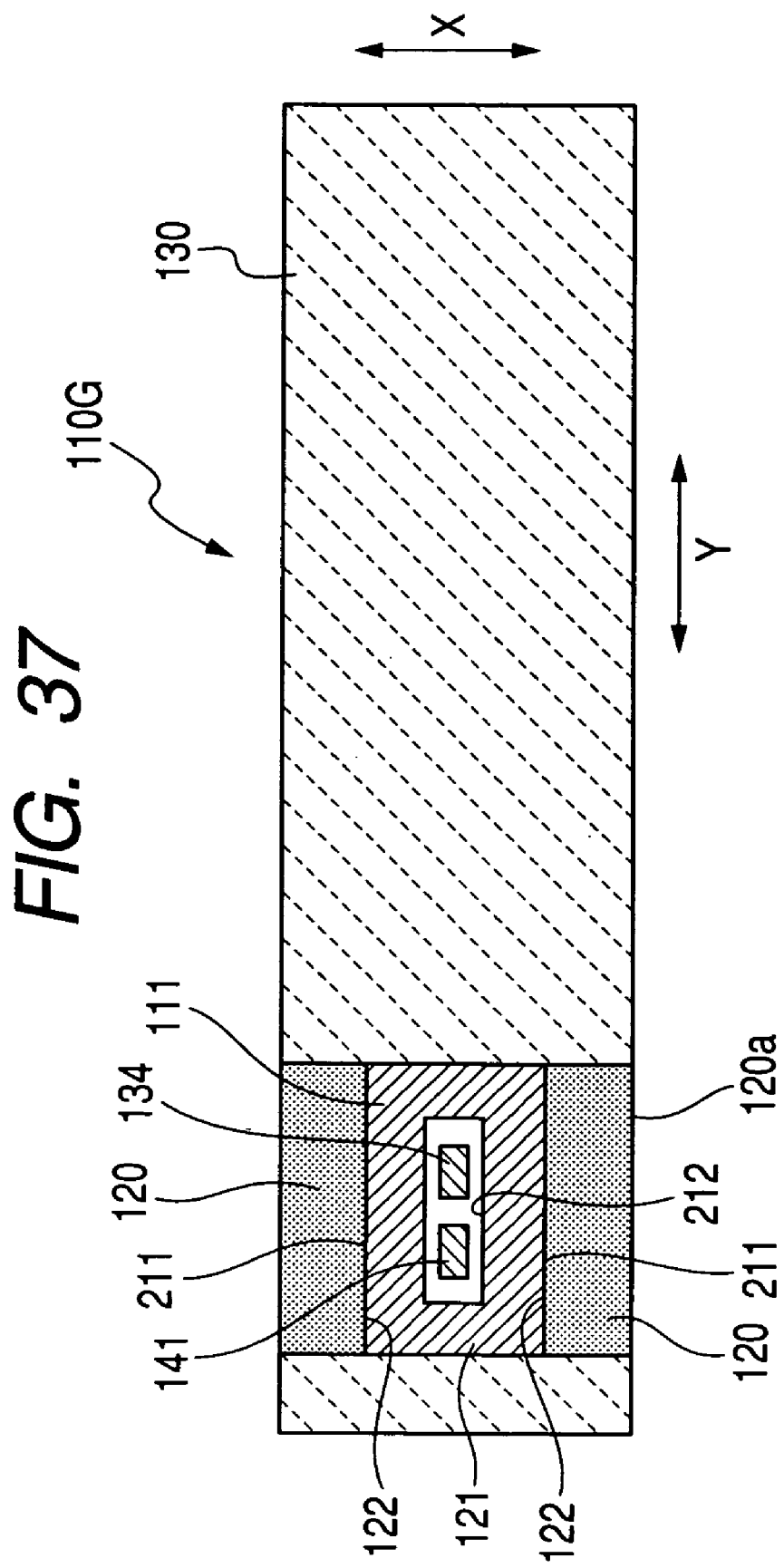

GAS SENSOR CONTROL DEVICE

CROSS REFERENCE TO RELATED APPLICATIONS

This application is based on Japanese Patent Application Nos. 2008-37295 filed on Feb. 19, 2008, and 2008-37296 filed on Feb. 19, 2008, the contents of which are hereby incorporated by reference.

BACKGROUND OF THE INVENTION

1. Technical Field of the Invention

The present invention relates to gas sensor controllers and, more particularly, to a gas sensor control device connected to a gas sensor such as a NOx sensor or the like for detecting a concentration of a specified component based on an output of the gas sensor.

2. Description of the Related Art

In recent years, there has been a tendency with tighter controls on exhaust emissions and fuel efficiency requirements. Thus, a need has been arisen to provide a technology related to, for instance, NOx emission reduction of a diesel engine and another technology related to failure detection on a NOx purifying device. Further, even a gasoline engine has an expanded application with a need to combust an air/fuel mixture in a lean-burn region accompanied by an increase NOx emissions. Thus, a need arises to provide a technology related to NOx emission control and another technology related to failure detection on a NOx purifying device. Because of these situations, there has been an increasing demand for a NOx sensor. Also, the NOx sensor may preferably include a sensing element of a multi-cell type employing a zirconia solid electrolyte body.

With the gas sensor involving the NOx sensor set forth above, an output error exists on a sensor current measured value due to an error factor peculiar to the sensor per se in general practice and another error factor present in a detection circuit connected to the gas sensor. Examples of the error factor of the gas sensor may include an individual difference and deterioration with age, etc. Examples of the error factor of the detection circuit may include a precision of a circuit element and a temperature characteristics, etc. Especially, with NOx sensor, a weak sensor current flows depending on a NOx concentration, resulting in a her increased risk of a drop in detecting precision due to the error factors. With an oxygen sensor (A/F sensor) arranged to detect an oxygen concentration, a sensor current is present in a mA-order. In contrast, the NOx sensor generates a sensor current in a nA-order with a difference in current level by 4 to 5 order of magnitudes.

With a prior art to address such issues, an attempt has been made to provide a detection circuit having a switch provided on a current pathway through which a sensor current flows. The switch is temporarily opened to shut off the sensor current from flowing through the detection circuit and a sensor current measured value is is acquired under such a state to allow an output error of the detection circuit to be calculated (see, for instance, Japanese Patent Application Publication No. 2005-326388).

However, with the detection circuit of such a structure having the switch provided on the electric pathway through which the sensor current flows, there is concern that an adverse affect occurs on sensor current detection caused by the switch. In case of using the switch comprised of, for instance, a semiconductor switching element, a leakage current (leak current) occurs in the switching element in the order of several tens nA. From this, there is a fear that a measuring error occurs when measuring the weak current like a phase when detecting the NOx concentration and there is room for improvement.

Meanwhile, with the gas sensor involving the NOx sensor set forth above, there is a need to detect that a function of the gas sensor is normal and examples of a detecting item include disconnection determination for the sensing element. With an automotive exhaust gas sensor, there is likelihood that disconnection determination is specified under a provision of law and regulations. Examples of technology of detecting a failure in the gas sensor may include those which detects a sensor disconnection based on an element impedance of, for instance, an A/F sensor. More particularly, in detecting impedance, a sweep variation is caused to occur in an set voltage to obtain a current change magnitude or an impedance value can be calculated during such sweep variation. Thus, failure detection is executed based on the current change magnitude or the impedance value. By conducting failure detection based on the element impedance, it becomes possible to make a query as to whether there is a normal operation or a failure operation even if the sensor output is "0". That is, with an air/fuel ratio feedback control executed with a target on a theoretical air fuel ratio (in stoichiometric ratio), the sensor output is kept intact at nearly "0" and, even in such a case, failure such as disconnection or the like can be detected.

However, with a circuit arranged to detect a weak current like, for instance, a NOx detection signal, the weak current detection and impedance detection can be realized on a common circuit, causing a risk of deterioration in precision of NOx detection. That is, a current level resulting from impedance detection is in a mA order. On the contrary, a current level for the NOx detection signal lies in an nA-order with a difference in current level differing from each other by the 4th-order to 5th-order digits. Accordingly, it is difficult to perform both the NOx detection and the impedance detection at increased precision, causing deterioration in precision of detecting the NOx concentration.

Further, a technology has been proposed in which a detection circuit has a switch provided on a current pathway through which a NOx detected current flows (see, for instance, Japanese Patent Application Publication No. 2005-326388). With the use of such a technology, a NOx detection circuit and an impedance detection circuit can be suitably switched, thereby making it possible to extract a signal of a current level depending on needs.

However, with the structure in which the switch is provided in the current pathway through which a NOx detection current flows in the detection circuit, there is concern that the switch adversely affect on NOx current detection. That is, with the switch composed of, for instance, a semiconductor switching element, a leakage current (leak current) occurs in the witching element in the order of several tens nA. Therefore, in measuring a weak current like a phase when detecting the NOx concentration or the like, there is a risk of a measuring error and there is room for improvement.

SUMMARY OF THE INVENTION

It is therefore an object of the present invention to provide a gas sensor control device in which a current correcting value for correcting an element current is appropriately calculated to detect a concentration of a specified component such as NOx concentration or the like with high precision.

It is another object of the present invention to provide a gas sensor control device in which a failure such as an activity deficiency or disconnections can be properly determined while suppressing an adverse affect on precision of detecting a gas concentration.

Hereunder, a structure for addressing the above issues and advantageous effects are described below.

According to the present invention, a gas sensor control device is connected to a gas sensor, including a gas sensing element composed of a solid electrolyte body and a pair of electrodes formed on the solid electrolyte body, in which an element current occurs depending on a concentration of a specified component in measuring gases upon receipt of a voltage applied across the pair of electrodes. With the gas sensor control device, the element current is measured with a current-voltage converter and a measured result on the element current, measured with the current-voltage converter, is output as an element current measured value from an output circuit. Further, a concentration of a specified component (oxygen concentration and NOx concentration or the like) is calculated based on the element current measured value, output from the output circuit, in the presence of a voltage applied from an applied voltage setting circuit.

With one embodiment of the present invention, further, switch means (a switch circuit 71 shown in FIG. 4) is provided in an element-current flow disabling pathway through which no element current flows. With the switch means being closed, a set voltage (applied voltage) of an applied voltage setting circuit is regulated such that a potential difference between both terminals of the current-voltage converter lies at a predetermined specified value. A current correcting value for correcting the element current is calculated using the output value of the output circuit under such a state. Also, on the way of detecting the gas concentration based on the element current measured value, the switch means is temporarily closed to calculate the current correcting value.

With such a structure, causing the switch means to be brought into a closed state allows two phases to be established.

In one phase, a sensor-side terminal voltage of the current-voltage converter is input to the applied voltage setting circuit in a feedback loop.

In the other phase, the applied voltage of the applied voltage setting circuit is regulated in response to a feedback input such that the potential difference between the both terminals of the current-voltage converter lies at the predetermined specified value.

With such phases in operation, it becomes possible to appropriately obtain the current correcting value for correcting the element current equivalent to a variation component in characteristic of the instant gas sensor control device. That is, by comparing the element current measured value (an element current value actually measured with a circuit), appearing when the potential difference between the both terminals of the current-voltage converter is set to the specified value, and an output value (a design value, etc.,) to be originally output, the current correcting value for correcting the element current can be calculated depending on a difference between those factors.

With the present embodiment of the present invention, further, the switch means is provided on the element-current flow disabling pathway in which no element current flows. This can avoid an inconvenience of causing an error in the element current measured value due to a cause of a leak current induced in the switch means, i.e., a semiconductor switching element such as a transistor, etc. Especially, when measuring a weak element current, there is likelihood that an error occurs in the current measuring value due to a cause of the existence of the switch means. Such an error results in an increase in an adverse affect on a consequence of detecting the gas concentration. However, the provision of such switch means can avoid the occurrence of such inconvenience.

With the present embodiment of the present invention set forth above, furthermore, the current correcting value for correcting the element current can be appropriately calculated with a resultant capability of improving precision of detecting the gas concentration.

With the present embodiment of the present invention, closing the switch means allows the potential difference between the both terminals of the current-voltage converter to be zeroed. This allows the output value of the output circuit to be obtained under a condition where the potential difference remains zeroed. In this case, with the potential difference between the both terminals of the current-voltage converter being zeroed, it becomes possible to establish a state in which no element current flows, i.e., a state of element current ≈0 nA and the current correcting value can be obtained with the state of element current ≈0 nA.

Further, as used herein, the state under which "the potential difference between the both terminals of the current-voltage converter is zeroed" corresponds to a state in which the current, flowing through the sensing element, lies at 0 nA or nearly 0 nA. In this case, an actual circuit structure is comprised of a variety of circuit elements and due to the existence of such circuit elements, a negligible current flows through the actual circuit structure. Strictly speaking, although no situation stands for the state of "element current ≈0 nA", it is supposed that the presence of a flow of such a negligible current due to a cause of the circuit structure corresponds to the state in which the potential difference between the both terminals of the current-voltage converter is "zeroed".

The state (i.e., a state with element current ≈0 nA) in which the potential difference between the both terminals of the current-voltage converter is zeroed represents a specified component concentration=0% (or 0 ppm) and element current ≈0 nA. In such a case, the element current measured value with the state (i.e., the state with element current ≈0 nA) in which the potential difference between the both terminals of the current-voltage converter is zeroed corresponds to an offset error. Thus, an offset correcting value may be preferably calculated as the current correcting value under the state in which the potential difference between the both terminals of the current-voltage converter is zeroed.

With the present embodiment of the present invention, a first feedback pathway (a feedback pathway L1 in FIG. 4), through which an output of the output circuit is input in feedback to the applied voltage setting circuit, and a second feedback pathway (a feedback pathway L2 in FIG. 4), through which a voltage at a sensor-side terminal of the current-voltage converter is input in feedback to the applied voltage setting circuit. The switch means is provided in the second feedback pathway of the two feedback pathways. During normal concentration detecting operation, of the two feedback pathways, the first feedback pathway is brought into a conducting state to allow the applied voltage setting circuit to set the applied voltage depending on the output of the output circuit input in feedback via the first feedback pathway. During an operation to calculate the current correcting value for correcting the element current, of the two feedback pathways, only the second feedback pathway is brought into a conducting state to allow the applied voltage setting circuit to set the applied voltage depending on a sensor-side terminal voltage of the current-voltage converter input in feedback via the second feedback pathway.

With such a structure, suitably selecting the feedback pathway to the applied voltage setting circuit enables the gas concentration detecting operation to be temporarily interrupted, upon which the current correcting value can be calculated.

With the present embodiment of the present invention, at least one of a voltage follower and a noninverting amplifier circuit is disposed in an electric pathway through which a sensor-side terminal of the current-voltage converter and the applied voltage setting circuit are electrically connected to each other. The switch means is provided in a pathway between the at least one of the voltage follower and the noninverting amplifier circuit and the applied voltage setting circuit. With such a structure, no element current flows through an output side of at least one of the voltage follower and the noninverting amplifier circuit and the applied voltage setting circuit. This makes it possible to establish a pathway in the electric pathway between the sensor-side terminal of the current-voltage converter and the applied voltage setting circuit in which no element current flows. With the switch means being provided on such a pathway, it becomes possible to prevent the switch means from adversely affecting the element current.

With the present embodiment of the present invention, the applied voltage setting circuit includes an operating amplifier having a negative feedback portion and the current-voltage converter is connected to an output side of the operating amplifier at a location outside of the negative feedback portion. With such a structure, measuring a voltage of at least an opposite-to-sensor side terminal of the current-voltage converter enables the element current to be measured. In addition, the output terminal voltage of the operating amplifier, i.e., the voltage at the opposite-to-sensor side terminal of the current-voltage converter, can be controlled, enabling an opposite-to-sensor side terminal voltage to increase or decrease with respect to a sensor-side terminal voltage. In other words, the potential difference between the both terminals of the current-voltage converter can be controlled. Accordingly, this makes it possible to allow the potential difference between the both terminals of the current-voltage converter to be zeroed or controlled to other differing values.

With the present embodiment of the present invention, it is structured that with the switch means remains closed, the applied voltage of the applied voltage setting circuit is set to a voltage having a given potential difference ($\neq 0$) with respect to a sensor-side terminal voltage of the current-voltage converter. With such a structure, causing the potential difference between the both terminals of the current-voltage converter to be set to the given value except for the zeroed value establishes a status in which a given element current flows. That is, a situation stands for a state with "element current=given value ($\neq 0$ nA)". This results in a capability of acquiring the current correcting value under the state with "element current=given value".

When a gain error occurs as a variation in characteristic of the instant sensor control device, the potential difference between the both terminals of the current-voltage converter is adjusted to at least two different voltage values to permit the gain correcting value to be calculated depending on the circuit output present at that time. In such a case, the gain correcting value may be calculated in a manner described below.

With the present embodiment of the present invention, when the switch means is brought into a closed state, the applied voltage of the applied voltage setting circuit is regulated to voltages inducing a plurality of potential differences with respect to a sensor-side terminal voltage of the current-voltage converter, thereby acquiring an output value from the output circuit under a plurality of states for the voltages to be regulated. The correcting value calculating means calculates a gain correcting value as the current correcting value in response to the output value of the output circuit acquired under the plurality of states.

With the present embodiment of the present invention, when the switch means is brought into a closed state, the applied voltage of the applied voltage setting circuit is regulated in a first state to a first voltage, inducing a zeroed potential difference with respect to a sensor-side terminal voltage of the current-voltage converter, and in a second state to a second voltage inducing a given potential difference ($\neq 0$) with respect to the sensor-side terminal voltage of the current-voltage converter. The correcting value calculating means calculates a gain correcting value as the current correcting value in response to the output value of the output circuit acquired under the first and second states.

With such a structure, when causing a given potential difference between the both terminals of the current-voltage converter, a voltage generating section allows the voltage equivalent to the potential difference between the both terminals of the current-voltage converter to be input to the applied voltage setting circuit. Permitting the voltage equivalent to the potential difference between the both terminals of the current-voltage converter to be input to the applied voltage setting circuit in conformity to the closed state of the switch means causes the given potential difference ($\neq 0$) to occur with respect to the sensor-side terminal voltage of the current-voltage converter.

In short, with the invention mentioned above, the voltage generating section is connected to the input of the applied voltage setting circuit as a structure for causing the potential difference between the both terminals of the current-voltage converter. In this case, the potential difference is caused to occur between the both terminals of the current-voltage converter in line with the output voltage of the voltage generating section, making it possible to set the potential difference between the both terminals to an arbitrary level.

Further, the concentration of the specified component in measuring gases can be adjusted to two or more reference concentrations (i.e., for instance, a stoichiometric state and an atmospheric state for detecting an oxygen concentration in exhaust gases). In such a case, measuring the element current after the adjustment is made to such reference concentrations makes it possible to utilize the respective measured value for acquiring the gain error. In another case where the concentration of the specified component in measuring gases cannot be adjusted to the two or more reference concentrations, an effective expedient is to provide the voltage generating section to allow the voltage, equivalent to the potential difference between the both terminals, to be input to the applied voltage setting circuit. That is, such an expedient is effective for a gas sensor control device that detects, for instance, a NOx concentration in exhaust gases.

With the present embodiment of the present invention, moreover, the correcting value calculating means may preferably calculate the current correcting value subjected to the sensing element remaining in an activating state. This allows a stabilized voltage to appear at a terminal portion connected to the sensing element, making it possible to obtain the current correcting value with increased precision.

The gas sensor control device, implementing the present invention, can be suitably applied to a gas sensor of the type described below. That is, the gas sensor may preferably include the sensing element composed of the solid electrolyte body and first and second cells (a pump cell and a sensor cell) exposed to a gas chamber. Each of the first and second cells is composed of a pair of electrodes formed on the solid electrolyte body. The first cell regulates an oxygen quantity of measuring gases, admitted to the measuring gas chamber, to a given concentration level and the second cell detects a specified component of the measuring gases with the oxygen quantity being regulated with the first cell. With the gas sensor control device, the current-voltage converter measures a second cell current caused in the second cell to provide a second cell current measured value based on which the concentration of the specified component is calculated. In such a case, examples of the concentration of the specified component, measured with the second cell, include concentrations of NOx and HC, etc., except for oxygen. In this case, the element current to detect the relevant concentration is weak. For instance, the element current for the operation to detect the NOx concentration lies in nA (Nanoampere) order. In this respect, with the structure having the various features mentioned above, even if the element current is weak, the gas concentration can be appropriately detected.

With the gas sensor control device of the present invention, the gas sensor (sensing element), having the first and second cells as mentioned above, may further preferably include a third cell (monitor cell) for detecting a residual oxygen concentration of the measuring gases in the measuring gas chamber. With such a gas sensor, the second and third cells have electrodes formed in a common electrode to which a voltage is applied from a common driver circuit section. In this case, the gas sensor control device includes a second cell current detecting circuit for measuring a second cell current caused in the second cell, and a third cell current detecting circuit for measuring a third cell current caused in the third cell and the second and third cells incorporate the switch means. The second cell current detecting circuit and the third cell current detecting circuit may calculate a current correcting value for correcting the second cell current and a current correcting value for correcting the third cell current based on the output value of the output circuit acquired under conditions where the second and third cell current detecting circuits are closed with the switch means.

With such a structure, the switch means, located in the current detecting circuits for the second and third cells, respectively, are individually opened or closed, thereby making it possible to individually calculate characteristic variations (circuit errors) of the respective current detecting circuits. Such a structure enables the current correcting values to be calculated at further increased precision than that achieved with the structure in which the switch means is provided in the driver circuit section common to the second and third cells.

Further, failure determining means may be preferably provided for determining a failure occurring in at least one of the sensing element and a sensor circuit based on a current correcting value for correcting the element current resulting from the correcting value calculating means. That is, during the occurrence of the failure in at least one of the sensing element and the sensor circuit, there is a risk in that the current correcting value to be calculated in a manner described above, takes an unlikely value (a value that cannot be addressed with the correction). Accordingly, a failure determination can be executed using the current correcting value.

Further, voltage application interrupting means may be preferably provided for interrupting the voltage from being applied to the sensing element when the failure determining means determines that the failure is present. This suppresses an adverse affect on the sensing element caused by a continuous application of voltage to the sensing element in the occurrence of the failure, thereby enabling the sensing element to be protected.

With another embodiment of the present invention, the gas sensor, connected to the gas sensor control device, includes the sensing element composed of the solid electrolyte body and the pair of electrodes formed on the solid electrolyte body, in which the element current occurs depending on the concentration of the specified component in measuring gases upon receipt of the voltage applied across the pair of electrodes. With the gas sensor control device, the element current is measured with the current-voltage converter and the measured result on the element current, measured with the current-voltage converter, is output as the element current measured value from the output circuit. Further, the concentration of the specified component (oxygen concentration and NOx concentration or the like) is calculated based on the element current measured value, output from the output circuit, in the presence of the voltage applied from the applied voltage setting circuit.

With the present embodiment, further, the switch means (switch circuit 71 shown in FIG. 4) is connected to the pathway, in which no element current flows, of electrical electric pathways through which the sensor-side terminal of the current-voltage converter and the applied voltage setting circuit are electrically connected to each other. With the switch means being closed, the potential difference between the both terminals of the current-voltage converter is zeroed, under which an electromotive force of the sensing element is detected. Then, the operation is executed to determine a failure in at least one of the sensing element and the sensor circuit based on the detected electromotive force. In addition, on the way of detecting the gas concentration based on the element current measured value, the switch means may be temporarily closed to detect the electromotive force.

With such a structure, by causing the potential difference between the both terminals of the current-voltage converter to be zeroed, it becomes possible to establish a state in which no element current flows, i.e., a state of element current ≈0 nA and the electromotive force of the sensing element can be properly detected. In such moment, if the sensing element encounters a failure, such as damage or defective activity or the like, or another failure such as disconnection or the like in the sensor circuit, the sensor electromotive force cannot take an appropriate value. This makes it possible to make a failure determination based on the sensor electromotive force.

With the present embodiment, the switch means is provided on the pathway in which no element current flows. This can avoid an inconvenience of causing an error in the element current measured value due to a cause of a leak current induced in the switch means, i.e., a semiconductor switching element such as a transistor, etc. Especially, when measuring a weak element current like a NOx detection current, there is likelihood that an error occurs in the current measuring value due to a cause of the existence of the switch means. Such an error results in an increase in an adverse affect on a consequence of detecting the gas concentration. However, such an inconvenience can be avoided.

With the present embodiment set forth above, a failure such as the disconnection caused in the sensor can be properly determined while minimizing the occurrence of the adverse affect on precision of detecting the gas concentration.

Further, the state under which the potential difference between the both terminals of the current-voltage converter is "zeroed" corresponds to a state in which the current, flowing through the sensing element, lies at 0 nA or nearly 0 nA. In this case, an actual circuit structure is comprised of a variety of circuit elements and due to the existence of such circuit elements, a negligible current flows through the actual circuit structure. Strictly speaking, although no situation stands for the state of "element current ≈0 nA", it is supposed that the presence of a flow of such a negligible current due to a cause of the circuit structure corresponds to the state in which the potential difference between the both terminals of the current-voltage converter is "zeroed".

The potential difference between the both terminals of the current-voltage converter can be zeroed using such a structure described below. That is, the gas sensor control device may be preferably arranged in structure such that with the switch means being closed, inputting a sensor-side terminal voltage of the current-voltage converter to the applied voltage setting circuit in a feedback loop to allow the set voltage, determined by the applied voltage setting circuit, to be equal to the sensor-side terminal voltage.

As a method of detecting the sensor electromotive force, the electromotive force of the sensing element may be preferably detected using the sensor-side terminal voltage of the current-voltage converter with the switch means being closed. In an alternative, voltages at positive and negative terminals of the sensing element are measured with the switch means being closed and the operation may be executed to detect the electromotive force of the sensing element based on a difference between measured voltage values.

With any one of such structures mentioned above, the electromotive force can be appropriately detected. However, using the difference between the measured voltage values of the positive and negative terminals of the sensing element allows the electromotive force to be reliably detected with high precision.

With the present embodiment, the sensor-side terminal of the current-voltage converter may be preferably connected to a reference potential portion (such as, for instance, ground) via a bias resistor. In short, with the occurrence of a failure such as a disconnection or the like, no sensor electromotive force is generated, resulting in an indefinite circuit output. With such a structure, even if no sensor electromotive force is present, the bias resistor allows the sensor-side terminal voltage of the current-voltage converter to be kept at a given voltage. Consequently, even in the absence of electromotive force, the circuit output can be stabilized, making it possible to detect the sensor electromotive force as a failure value.

With the present embodiment, a first feedback pathway (a feedback input electric pathway L1 in FIG. 4), causing the output of the output circuit to be input to the applied voltage setting circuit in feedback loop, and a second feedback pathway (a feedback input electric pathway L2 in FIG. 4), causing the voltage at the sensor-side terminal of the current-voltage converter to be input to the applied voltage setting circuit in feedback loop, may be preferably provided. Of the two feedback pathways, the second feedback pathway incorporates the switch means. During a normal concentration detecting operation, only the first feedback pathway of the two feedback pathways is brought into a conductive state to allow the applied voltage setting circuit to set the applied voltage depending on the output of the output circuit input thereto via the first feedback pathway in feedback loop. Further, during the operation to detect the electromotive force, only the second feedback pathway of the two feedback pathways is brought into a conductive state to allow the applied voltage setting circuit to set the applied voltage depending on the sensor-side terminal voltage of the current-voltage converter input via the second feedback pathway in feedback loop. In this case, the potential difference between the both terminals of the current-voltage converter is zeroed.

With such a structure, suitably switching the feedback pathway to the applied voltage setting circuit enables the gas concentration detection to be temporarily interrupted, thereby detecting the sensor electromotive force.

With the present embodiment, at least one of a voltage follower and a noninverting amplifier circuit may be preferably disposed in an electric pathway through which the sensor-side terminal of the current-voltage converter and the applied voltage setting circuit are electrically connected to each other. The switch means is provided in a pathway between the at least one of the voltage follower and the noninverting amplifier circuit and the applied voltage setting circuit. With such a structure, no element current flows through the voltage follower or the noninverting amplifier circuit. This makes it possible to provide a pathway, interrupting the flow of element current, in the pathway between the sensor-side terminal of the current-voltage converter and the applied voltage setting circuit. Further, providing the switch means in such a pathway prevents the switch means from adversely affecting the element current.

With the present embodiment, the applied voltage setting circuit may preferably include an operating amplifier having a negative feedback portion and the current-voltage converter may be preferably connected to an output side of the operating amplifier at a location outside of the negative feedback portion. With such a structure, measuring a voltage of at least the opposite-to-sensor terminal of the current-voltage converter enables the element current to be detected. In addition, the output terminal voltage of the operating amplifier, i.e., the voltage at the opposite-to-sensor terminal of the current-voltage converter can be controlled. This results in a capability of increasing or decreasing an opposite-to-sensor side terminal voltage with respect to a sensor-side terminal voltage. In other words, it becomes possible to control the potential difference between the both terminals of the current-voltage converter. Accordingly, this makes it possible to zero the potential difference between the both terminals of the current-voltage converter.

With the present embodiment, terminal voltage measuring means may be preferably provided for measuring voltages at terminal portions connected to respective electrodes of the sensing element. Further, not only a failure determination may be preferably made based on the electromotive force but also a failure determination may be preferably made based on at least one of the sensing element and the sensor circuit based on the respective terminal voltages. This results in a capability of detecting not only a failure such as a breakdown, a detective activity and a disconnection or the like but also another failure such as a power-supply shortage and a ground shortage at the electrodes of the sensing element.

With the present embodiment, voltage application interrupting means may be preferably provided for interrupting the application of the set voltage to the sensing means when the determination is made that a failure is present. This eliminates an adverse affect on the sensing element due to continuous application of voltage to the sensing element during the occurrence of the failure, thereby enabling the sensing element to be favorably protected.

With the present embodiment, an electromotive force detection may be preferably executed under a condition with the sensing element placed in an active state. That is, during, for instance, a startup of the gas sensor, the sensing element is raised to a given active temperature to fall in a completely active state, after which the sensor electromotive force can be property detected. With the present invention, it becomes possible to minimize a defect of detecting the electromotive force arising from inactivity (i.e. at a low temperature) of the sensing element. This enables a failure detection to be conducted with increased precision.

With the present embodiment, the gas sensor control device may be preferably applied to a gas sensor described below. That is, the gas sensor includes a sensing element having first and second cells, exposed to a gas chamber, each of which is composed of a pair of electrodes formed on the solid electrolyte body. The first cell regulates an oxygen quantity of measuring gases, admitted to the measuring gas chamber, to a given concentration level and the second cell detects a concentration of a specified component (NOx concentration) of the measuring gases with the oxygen quantity being regulated with the first cell. With the gas sensor control device, the current-voltage converter measures the element current occurring in the second cell. In such a case, the specified component, measured with the second cell, includes a concentration of NOx and HC or the like except for oxygen and the element current for detecting such a concentration is weak. For instance, the element current appearing when detecting the NOx concentration lies in the nA (nanoampere) order. With the various characteristic features set forth above, the gas concentration can be favorably detected even in the presence of the weak element current.

With the present embodiment, electromotive force detection may be preferably executed under a condition in which an oxygen concentration in the measuring gas chamber lies at a low oxygen level representing the given concentration level. That is, during, for instance, the startup of the gas sensor, the sensor electromotive force can be properly detected upon causing the first cell to adequately discharge excessive oxygen form the measuring gas chamber. Thus, it becomes possible to eliminate a defect in detecting the electromotive force arising from the existence of excess oxygen (with oxygen in excessive quantities) present in the measuring gas chamber. This enables the failure detection to be executed with increased precision.

It is conceived that the residual oxygen concentration incrementally varies in the measuring gas chamber to cause the electromotive force of the second cell to vary depending on the residual oxygen concentration. With the present embodiment, accordingly, the residual oxygen concentration present in the measuring gas chamber may be preferably detected and a failure determining value is set to a variable level depending on the detected residual oxygen concentration present in the measuring gas chamber. Then, a failure determination is executed on at least one of the sensing element and the sensor circuit based on the failure determining value and the detected electromotive force. Thus, even if the residual oxygen concentration incrementally varies in the measuring gas chamber, the failure determination can be realized with high precision.

BRIEF DESCRIPTION OF THE DRAWINGS

These and other features and advantages of the present invention will become more apparent in light of the following description, as illustrated in the accompanying drawings, in which:

FIG. 5 is a flow char showing a failure detection routine to be executed by the microcomputer shown in FIG. 1.

FIG. 9A is a circuit structural view of an Is detecting circuit section of a gas sensor control device of another embodiment according to the present invention.

FIG. 37 is a cross sectional view of the gas sensing element taken on line Q-Q of FIGS. 35 and 36.

DETAILED DESCRIPTION OF PREFERRED EMBODIMENTS

Now, gas sensor control devices of various embodiments according to the present invention will be described below in detail with reference to the accompanying drawings. However, the present invention is construed not to be limited to such embodiments described below and technical concepts of the present invention may be implemented in combination with other known technologies or other technologies having functions equivalent to such known technologies.

In the following description, it is to be understood that such terms as "right side", "left side", "base end portion", "leading end portion", "top", "bottom", "upper", "lower", "fore", "aft", "sensor-side terminal", "opposite-to-sensor side terminal", "sensor-side terminal voltage", and "opposite-to-sensor side terminal" and the like are words of convenience and are not to be construed as limiting terms.

As used herein, the term "sensor-side terminal" refers to one terminal of a current-voltage converter placed at one position closer to a sensor cell and the term "opposite-to-sensor side terminal" refers to the other terminal of the current-voltage converter, i.e., a terminal placed at the other position opposite to the sensor cell. Likewise, the term "sensor-side terminal voltage" refers to a terminal voltage appearing at the one terminal of the current-voltage converter and the term "opposite-to-sensor side terminal voltage" refers to a terminal voltage at the other terminal of the current-voltage converter.

Now, a gas sensor controller of one embodiment according to the present invention will be described below in detail with reference to the accompanying drawings.

The present embodiment is described below with reference to a NOx concentration detecting system, employing a NOx sensor mounted on an exhaust pipe of an on-vehicle engine, which is arranged to detect a NOx concentration of exhaust gases in response to an output delivered from the NOx sensor. Further, the on-vehicle engine may include, for instance, a diesel engine. The diesel engine has an exhaust pipe carrying thereon an exhaust gas purifying device, including a NOx purifying catalyst (NOx occlusion-reduction type catalyst and ammonia selective reduction catalyst, etc.), a failure diagnosis of which is conducted on the basis of the output of the NOx sensor. The NOx sensor is mounted on the exhaust pipe in an area downstream of the NOx purifying catalyst to deliver the output. A NOx concentration (NOx purifying rate) of the NOx purifying catalyst is calculated in response to the output from the NOx sensor. If the resulting concentration is found to exceed a given failure determining value, then, a diagnosis is made that the NOx purifying catalyst has failed.

First, a gas sensing element 10, forming the NOx sensor, will be described below in detail with reference to FIG. 1 of the accompanying drawings.

Figure 1:
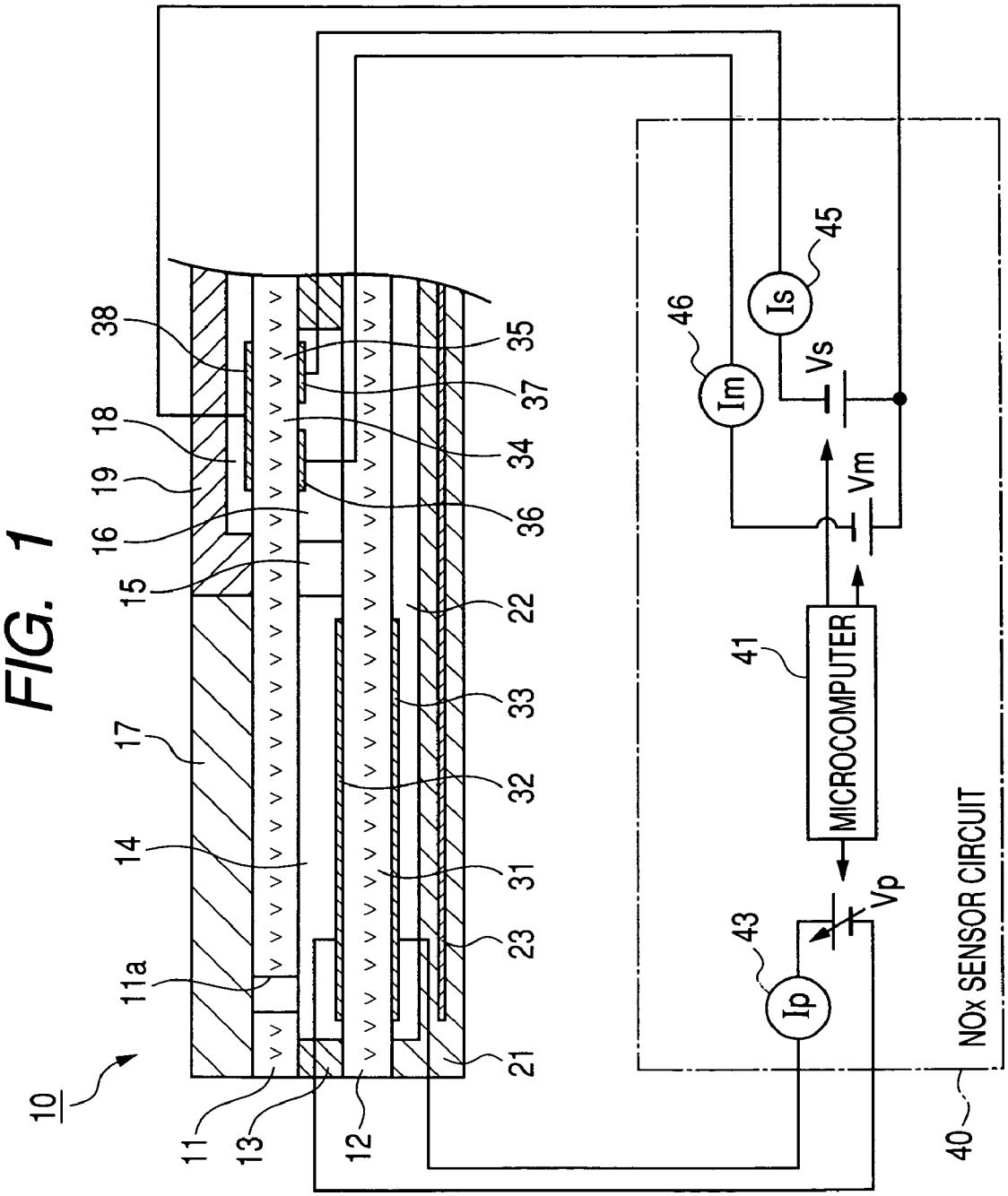
FIG. 1 is a cross-sectional view showing a gas sensor control device of an embodiment according to the present invention as applied to a gas sensor including a NOx sensor and a NOx sensor circuit while illustrating an element internal structure of the NOx sensor.

The sensing element 10 takes the form of a so-called stack type structure having an internal structure as shown in FIG. 1. It will be appreciated that a lateral direction in FIG. 1 represents a longitudinal direction of the sensing element 10. The sensing element 10 has a right side, representing an element base end portion (adapted to be mounted on the exhaust pipe), and a left side representing an element leading end portion.

The sensing element 10 has a so-called three-cell structure composed of a pump cell, a sensor cell and a monitor cell. These cells are stacked in structure to form an assembly. In addition, like the pump cell, the monitor cell has a function to exhaust oxygen from measuring gases and, hence, the monitor cell is often said to be an auxiliary pump cell or a second pump cell.

With the sensing element 10, first and second electrolyte bodies 11 and 12 are made of oxygen ion conducting material such as zirconia or the like and formed in sheet-like configurations. The first and second electrolyte bodies 11 and 12 are stacked on one another via a spacer 13, made of insulation material such as alumina or the like, to be spaced from each other by a given distance. Of these, the first electrolyte body 11, placed in an upper area, has a leading end portion formed with an exhaust gas inlet port 11a through which exhaust gases, prevailing in an area around the leading end portion of the gas sensing element 10, is admitted to a first chamber 14 defined between the first and second electrolyte bodies 11 and 12. The first chamber 14 communicates with a second chamber 16 defined between the first and second electrolyte bodies 11 and 12 via a throttle portion 25 located between the first and second chambers 14 and 16. The first electrolyte body 11 has a top surface including one half, provided with a porous diffusion layer 17 for extracting exhaust gases to and discharging the same from the first chamber 14, and the other half provided with an insulation layer 19 having a recessed portion 19a to define an atmospheric air passage 18 acting as a reference gas compartment.

Further, the second solid electrolyte body 12 has a bottom surface carrying thereon an insulation layer 21 having a recessed portion 21a defining an atmospheric air passage 22. A heater (heating body) 23 is embedded in the insulation layer 21 for heating a whole of the sensing element 10. With such a structure, the heater 23 heats the pump cell 31, the monitor cell 34 and the sensor cell 35. This promotes the activation of these cells 31, 34 and 35. The heater 23 is supplied with electric power from an external power supply (not shown) to generate heat energy.

The second solid electrolyte body 12, placed in a lower area, has the pump cell 31 disposed in face-to-face relation to the first chamber 14. The pump cell 31 is operative to admit oxygen in exhaust gases, admitted to the first chamber 14, or discharge the same such that a residual oxygen concentration is regulated at a given concentration in the first chamber 14.

The pump cell 31 includes a pair of upper and lower electrodes 32 and 33 between which the second solid electrolyte body 12 is sandwiched. The upper electrode 32, facing the first chamber 14, acts as a NOx inactive electrode (electrode that is hard to decompose NOx). The pump cell 31 is operative in response to a voltage applied across the electrodes 32 and 33 to cause oxygen present in the first chamber 14 to be decomposed and discharged through the electrode 33 to the atmospheric air passage 22.

Further, the first solid electrolyte body 11, placed on the upper side, has a base end portion formed with the monitor cell 34 and the sensor cell 35. After the pump cell 31 has discharged surplus oxygen, the monitor cell 34 generates an electromotive force depending on a residual oxygen concentration in the second chamber 16 or generates an electric current output in response to the application of a voltage. The sensor cell 35 detects a NOx concentration based on gases present in the second chamber 16.

The monitor cell 34 and the sensor cell 35, placed in juxtaposed positions in close proximity to each other, include electrodes 36 and 37, placed in face-to-face relation to the second chamber 16, and a common electrode 38 placed in face-to-face relation to the atmospheric air passage 18. That is, the monitor cell 34 takes the form of a structure including the first electrolyte body 11 and the electrode 36 and the common electrode 38 placed in opposite positions with the intervening of the first electrolyte body 11. Likewise, the sensor cell 35 takes the form of a structure including the first electrolyte body 11 and the electrode 37 and the common electrode 38 placed in opposite positions with the intervening of the first electrolyte body 11. The electrode 36 (placed in a position facing the second chamber 16) of the monitor cell 34 is made of noble metal such as Au—Pt that is inactive to NOx. The electrode 37 (placed in a position facing the second chamber 16) of the sensor cell 35 is made of noble metal such as platinum Pt and rhodium Rh or the like that are active to NOx. Although FIG. 1 shows the monitor cell 34 and the sensor cell 35 placed in a structure juxtaposed in a fore and aft direction with respect to a flow direction of exhaust gases for the sake of convenience, it will be appreciated that, in actual practice, the monitor cell 34 and the sensor cell 35 are located in positions equivalent to the flow direction of exhaust gases.

Here, the pump cell 31, the monitor cell 34 and the sensor cell 35 are juxtaposed in the longitudinal direction of the sensing element 10. Thus, the pump cell 31 is located in the sensing element 10 at the leading end portion thereof, and the monitor cell 34 and the sensor cell 35 are located on the sensing element 10 at the base end portion (adapted to be mounted on the exhaust pipe).

With the sensing element 10 of such a structure set forth above, exhaust gases are admitted to the first chamber 14 via the porous diffusion layer 17 and the exhaust gas inlet port 11a. When exhaust gases pass through a vicinity of the pump cell 31, a pump cell applied voltage Vp is applied across the pump cell electrodes 32 and 33. During application of such a voltage, a decomposing reaction occurs to cause the pump cell 31 to extract or discharge oxygen depending on an oxygen concentration in the first chamber 14. When this takes place, the pump cell electrode 32, facing the first chamber 14, is comprised of the NOx inactive electrode. Thus, the pump cell 31 is inoperative to decompose NOx in exhaust gases, while permitting only oxygen to be decomposed and discharged to the atmospheric air passage 22 from the electrode 33. With such a function of the pump cell 31, the first chamber 14 is kept in a condition with a given low oxygen concentration.

Gases (with the oxygen concentration being regulated), passed through the vicinity of the pump cell 31, flow into the second chamber 16, causing the monitor cell 34 to generate an output depending on the residual oxygen concentration in gases. The output of the monitor cell 34 is detected as a monitor cell current Im upon applying a given monitor cell applied voltage from a monitor cell power supply Vm across the monitor cell electrodes 36 and 38. Further, applying a given sensor cell voltage from a sensor cell power supply Vs across the sensor cell electrodes 37 and 38 allows NOx in gases to be decomposed in reduction, causing resultant oxygen to be discharged to the atmospheric air passage 18 via the electrode 38. When this takes place, an electric current (sensor cell current Is) flows through the sensor cell 35 thereby detecting the NOx concentration in exhaust gases.

To this end, the sensing element 10 is connected to a NOx sensor circuit 40. The NOx sensor circuit 40 includes a microcomputer 41, acting as a main body for executing sensor control, and a control circuit section (described below in detail with reference to FIG. 2). The microcomputer 41 and the control circuit section control various voltages including: the pump cell voltage Vp to be applied across the electrodes 32 and 33 of the pump cell 31; the monitor cell voltage Vm to be applied across the electrodes 36 and 38 of the monitor cell 34; and the censor cell voltage Vs to be applied across the electrodes 37 and 38 of the sensor cell 35. The microcomputer 41 is sequentially applied with various measured values on the pump cell current Ip, the monitor cell current Im and the sensor cell current Is, upon which the microcomputer 41 calculates the oxygen concentration and the NOx concentration depending on the measured values on those parameters.

Figure 2:
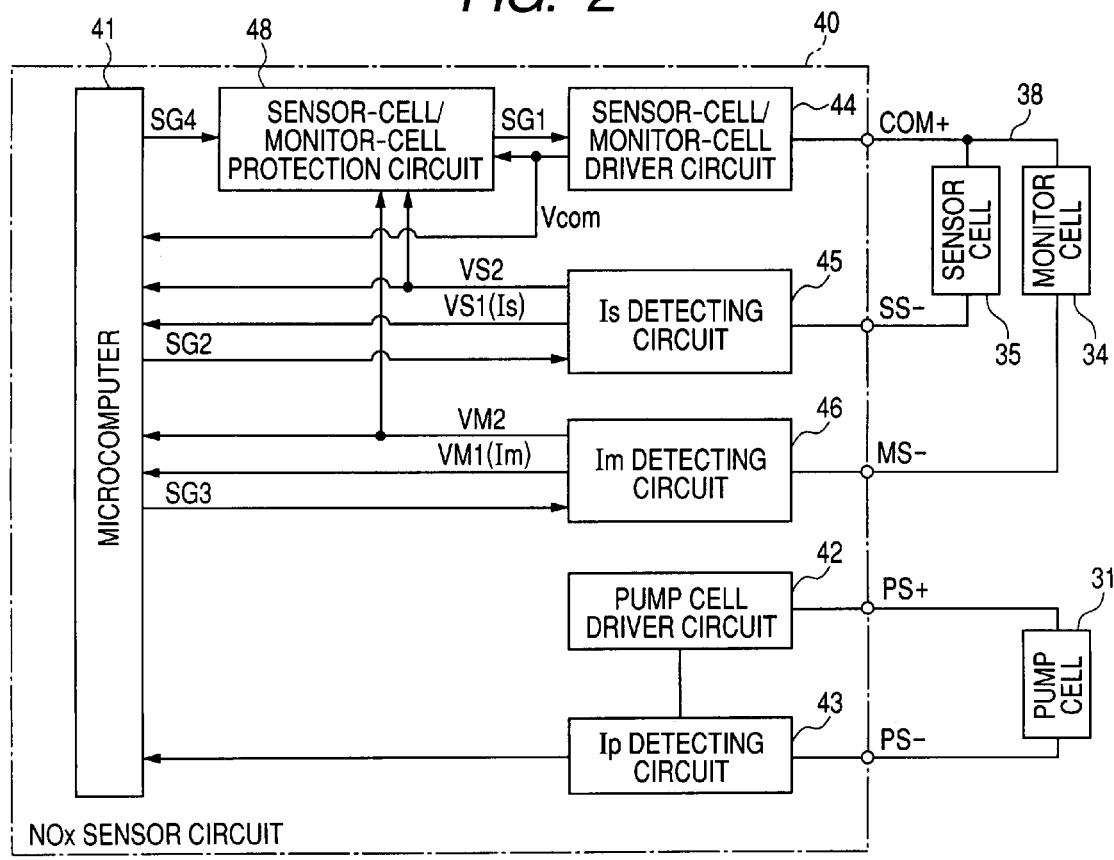
FIG. 2 is a block diagram showing an outline of the NOx sensor circuit shown in FIG. 1.

FIG. 2 is a block diagram showing an outline of the NOx sensor circuit 40. Although the NOx sensor circuit 40 includes not only various circuits, shown in the drawing, but also a heater driver circuit that is not shown in FIG. 2 for simplicity of illustration.

As shown in FIG. 2, the NOx sensor circuit 40 has a positive terminal PS+ and a negative terminal PS− connected to the electrodes 32 and 33 of the pump cell 31, a common terminal COM+ connected to the common electrode 38 of the monitor cell 34 and the sensor cell 35, and negative terminals MS− and SS− connected to the electrodes 36 and 37 of the monitor cell 34 and the sensor cell 35.

A pump cell driver circuit section 42 is connected to the positive terminal PS+ of the pump cell 31 for variably setting a pump cell applied voltage to be applied to the pump cell 31. An Ip detection circuit section 43 is connected to the negative terminal PS− of the pump cell 31 for detecting the pump cell current Ip. The pump cell driver circuit section 42 controls the pump cell applied voltage depending on the pump cell current Ip detected with the Ip detection circuit section 43. The pump cell current Ip, detected with the Ip detection circuit section 43, is sequentially input to the microcomputer 41.

Further, a sensor-cell/monitor-cell driver circuit section 44 is connected to the common terminal COM+ of the sensor cell 35 and the monitor cell 34 on the positive potential sides thereof to apply a common voltage thereto. An Is detection circuit section 45 and an Im detection circuit section 46 are connected to the negative terminals SS− and MS− of the sensor cell 35 and the monitor cell 34, respectively for detecting the censor cell current Im and the monitor cell Im, respectively. The Is detection circuit section 45 and the Im detection circuit section 46 are connected to the microcomputer 41. The Is detection circuit section 45 and the Im detection circuit section 46 calculate current measured values VS1 and VM1, measured depending on the sensor cell current Is and the monitor cell current Im, which are sequentially input to the microcomputer 41. In addition, the Is detection circuit section 45 and the Im detection circuit section 46 measure terminal voltages at respective terminals COM+, SS− and MS− that are sequentially applied to the microcomputer 41.

A sensor-cell/monitor-cell protecting circuit section 48 is connected to the sensor-cell/monitor-cell driver circuit section 44 for interrupting the applications of voltages to the monitor cell 34 and the sensor cell 35 to protect the same during the occurrence of a failure or the like.

Hereunder, description is made of details of various circuit sections, forming part of the NOx sensor circuit 40. However, with the present embodiment, the pump cell 31 has the same circuit structure as that of the existing art and, hence, details of the pump cell driver circuit section 42 and the Ip detection circuit section are herein omitted.

Figure 3:
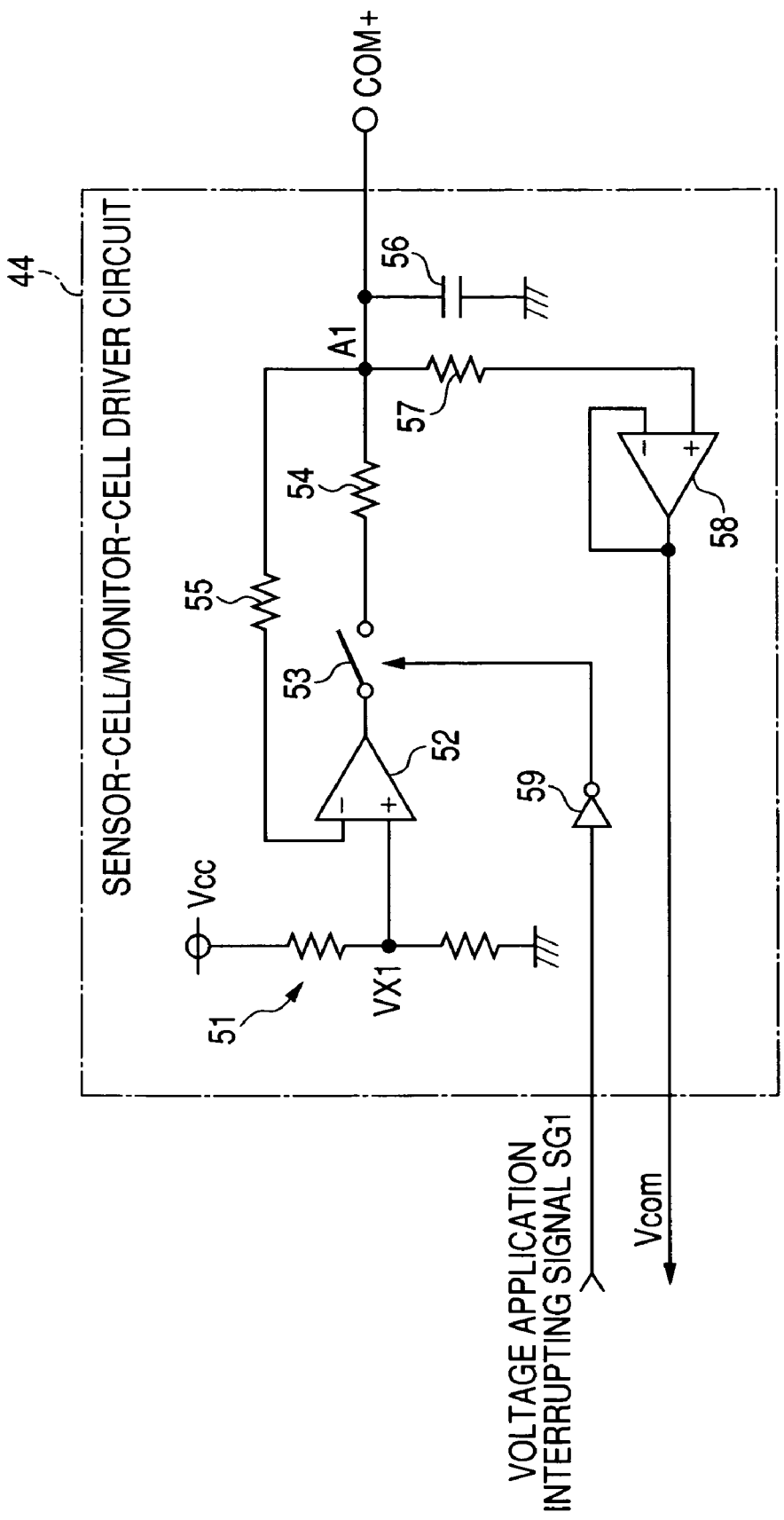
FIG. 3 is a circuit structural view showing a sensor-cell/monitor-cell driver circuit section shown in FIG. 2.

FIG. 3 is a circuit structural view of the sensor-cell/monitor-cell driver circuit section 44. In FIG. 3, a voltage divider resistance circuit 51, composed of two resistors, is connected to a constant voltage supply (at a constant Voltage Vcc) and applies a divided voltage VX1 to a "+" input terminal of an operating amplifier 52. The operating amplifier 52 has an output terminal to which the common terminal COM+ is connected via a switch circuit 53 and a protection resistor 54. The operating amplifier 52 has a negative feedback section in which a protection resistor 55 is provided. Connected to the common terminal COM+ is a capacitor 56 for addressing the occurrence of ESD (electrostatic discharging).

Further, a voltage follower 58 is connected to a junction A1, lying at the same voltage as that of the common terminal COM+, via a protection resistor 57. With the sensor-cell/monitor-cell driver circuit section 44, the voltage at the common terminal COM+ is output as a common terminal voltage Vcom.

The switch circuit 53 takes the form of a structure that is turned on and off (closed or opened) in response to a voltage application interrupting signal SG1 input from the sensor-cell/monitor-cell protecting circuit section 48, which will be described below in detail. The voltage application interrupting signal SG1 is applied to the switch circuit 53 via an inverting circuit 59. With the circuit of such a structure, if SG1="Low" (in an effect of permitting a voltage application), then, the switch circuit 53 is closed to allow the voltage divider resistance circuit 51 to apply the divided voltage VX1 to the common terminal COM+. In addition, if SG1="High" (in an effect of interrupting a voltage application), then, the switch circuit 53 is opened to interrupt the application of the divided voltage VX1 to the common terminal COM+.

Figure 4:
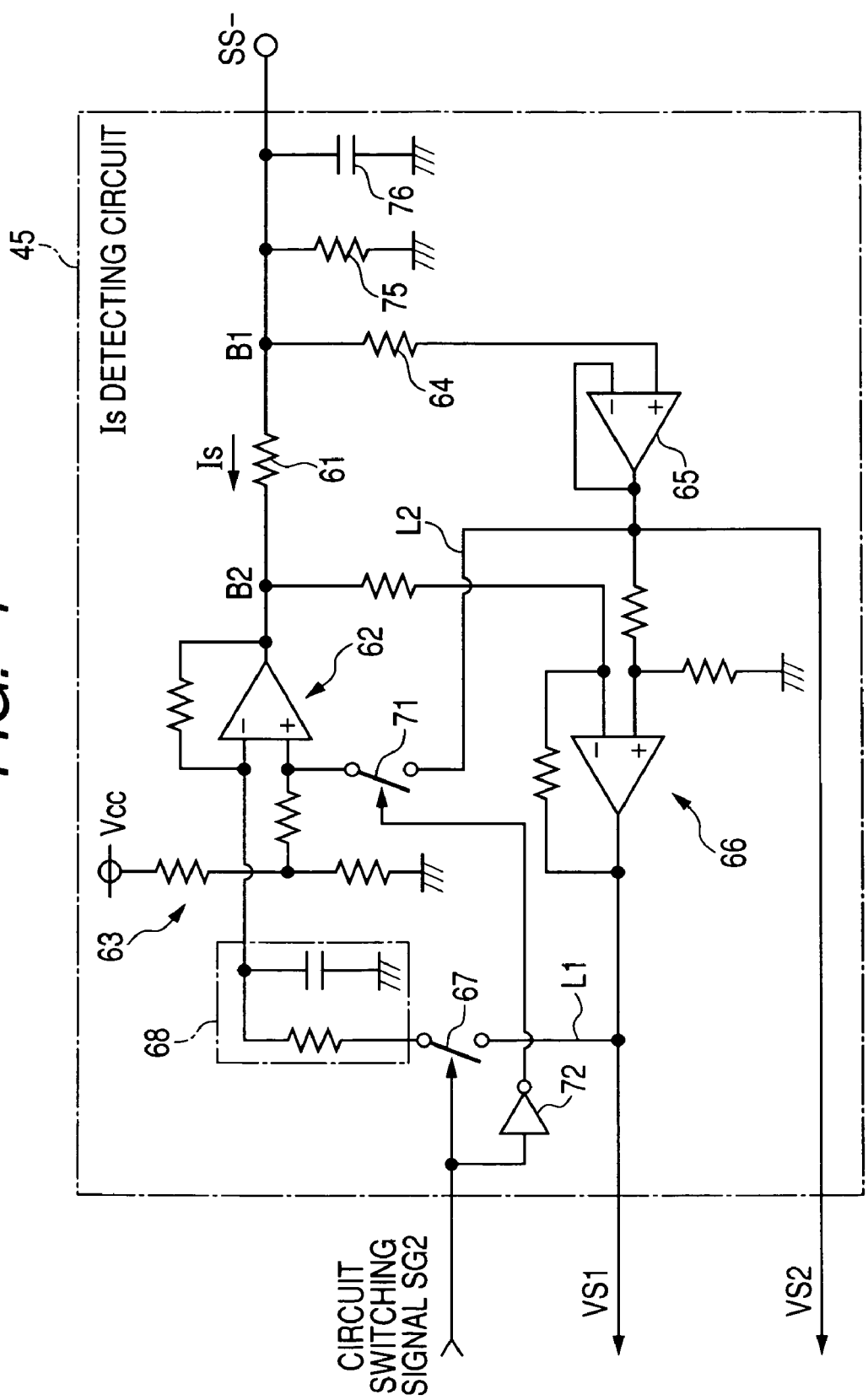
FIG. 4 is a circuit structural view showing an Is detecting circuit section shown in FIG. 2.

Next, a structure of the Is detection circuit 45 is described with reference to FIG. 4. In FIG. 4, the negative terminal SS− of the sensor cell 35 is connected to a current-voltage converter 61 and a differential amplifier circuit 62 in series. In this case, particularly, the current-voltage converter 61 is connected to an outside (an outside of a feedback system) of the negative feedback section representing an output of an operational amplifier forming the differential amplifier circuit 62. The differential amplifier circuit 62 has a "+" input terminal, connected to a resistor voltage dividing circuit 63 adapted to allow the constant voltage Vcc to be divided with two resistors, and a "−" input terminal to which a negative feedback input electric pathway L1 is connected.

Further, of both terminals (junctions B1 and B2) of the current-voltage converter 61, the junction B1 (hereinafter referred to as "sensor-side terminal of the current-voltage converter 61"), connected to the negative terminal SS−, is connected to a voltage follower 65 via a protection resistor 64 whose output terminal is connected to a "+" input terminal of a differential amplifier circuit 66. In addition, the junction B2 (hereinafter referred to as "opposite-to-sensor side terminal of the current-voltage converter 61") is connected to a "−" input terminal of the differential amplifier circuit 66. Accordingly, if the sensor cell current Is flows through the current-voltage converter 61, a potential difference occurs across the both terminals (i.e., the both junctions B1 and B2) of the current-voltage converter 61 depending on the sensor cell current Is, This voltage potential is amplified with the differential amplifier circuit 66 by a given amplification rate and subsequently output as the sensor-cell current measured value VS1.

The sensor-cell current measured value VS1, representing the output of the differential amplifier circuit 66, is input to the "−" input terminal of the differential amplifier circuit 62 via the negative feedback input electric pathway L1. To describe more particularly, the differential amplifier circuit 66 acts as an "output circuit" and the differential amplifier circuit 62 serves as an "applied voltage setting circuit". An output terminal of the differential amplifier circuit 66 and the "−" input terminal of the differential amplifier circuit 62 are connected to each other via the feedback input electric pathway L1. A switch circuit 67 is provided in the negative feedback input electric pathway L1 to connect or disconnect (close or open) the electric pathway L1, to which an LPF (Low Pass Filter) 68, composed of a resistor and a capacitor for removing noise, is also connected. In normal detecting operation, the switch circuit 67 remains closed, thereby permitting the sensor-cell current measured value VS1, representing the output of the differential amplifier circuit 66, to be input to the differential amplifier circuit 62 in feedback. In addition, the switch circuit 67 includes semiconductor switches such as, for instance, transistors or the like (with the same structure employed in each of various switch circuits described below).

The voltage follower 65 generates an output voltage, equal to a voltage at the junction B1 (i.e., a voltage at the negative terminal SS− of the sensor cell 35), which is output as the sensor-cell terminal voltage VS2.

Furthermore, an output terminal of the voltage follower 65 and the "+" input terminal of the differential amplifier circuit 62 are connected to each other via a negative feedback input electric pathway L2, which is connected to a switch circuit 71 for connecting or disconnecting (closing or opening) the negative feedback input electric pathway L2. In normal operation, the switch circuit 71 remains opened, thereby permitting the sensor-cell current measured value VS2, representing the output of the voltage follower 65, to be input to the differential amplifier circuit 62 in feedback. Here, the voltage follower 65 has increasing input impedance and no element current flows to an output of the voltage follower 65. Thus, the negative feedback input electric pathway L2 can be assigned to be an element-current flow disabling pathway in which no element current flows. The switch circuit 71 is provided in the element-current flow disabling pathway L2.

The switch circuits 67 and 71, connected to the negative feedback input electric pathways L1 and L2, have structures that are turned on or off (closed or opened) in response to a circuit switching signal SG2 with high or low levels delivered from the microcomputer 41. The circuit switching signal SG2 is input to the switch circuit 67 intact and also input to the switch circuit 71 via the inverting circuit 72. With the present embodiment, if SG2="High", the switch circuit 67 is closed and the switch 71 is opened. In this moment, only the negative feedback input electric pathway L1 of the negative feedback input electric pathways L1 and L2 is brought into a conducting state. On the contrary, if SG2="Low", the switch circuit 67 is opened and the switch 71 is closed. In this moment, only the negative feedback input electric pathway L2 of the negative feedback input electric pathways L1 and L2 is brought into a conducting state. The switch circuits 67 and 71 are opened and closed in a mode in which an opening and closing timing is reversed, thereby causing only one of the negative feedback input electric pathways L1 and L2 to be brought into the conducting state.

When detecting the NOx concentration during normal operation, i.e., when measuring the sensor current Is flowing depending on the NOx concentration of exhaust gases, the microcomputer 41 outputs the circuit switching signal SG2 at a high level. In this case, the output VS1 of the differential amplifier circuit 66 is input to the "−" input terminal of the differential amplifier circuit 62 via the negative feedback input electric pathway L1. Then, the output of the differential amplifier circuit 62 is amplified depending on the output VS1 of the differential amplifier circuit 66. In this moment, the greater the sensor cell current Is, the greater will be the output VS1 accompanied by a reduction in the output of the differential amplifier circuit 62.

In contrast, if the potential difference across the both terminals of the current-voltage converter 61 is zeroed and the current, flowing through the current-voltage converter 61, lies at 0 nA, then, the microcomputer 41 outputs a low signal as the circuit switching signal SG2. This causes the output VS2 of the voltage follower to be input to the "+" input terminal of the differential amplifier circuit 62 via the negative feedback input electric pathway L2. In this moment, the differential amplifier circuit 62 regulates the voltage of the current-voltage converter 61 at the terminal (junction B2) placed in opposition to the sensor to the same voltage as that of the current-voltage converter 61 at the terminal (junction B1) closer to the sensor. This causes the voltage potential across both terminals of the current-voltage converter 61 to be zeroed with a resultant state in which no current flows through the current-voltage converter 61 (i.e., a state as expressed as Current=0 nA). In such a case, the state under which no current flows through the current-voltage converter 61 represents a state with NOx Concentration=0 ppm. If an offset error is present, a deviation occurs in an output value by such an error. Therefore, it becomes possible to obtain the offset error based on such an output.

Further, the presence of the low signal output from the microcomputer 41 as the circuit switching signal SG2 results in the state with no current flowing through the current-voltage converter 61. In this moment, a voltage occurs on the negative terminal SS− of the sensor cell 35 at a level depending on a sensor cell electromotive force and this voltage is measured as the sensor-cell terminal voltage VS2.

Of the both terminals (junctions B1 and B2) of the current-voltage converter 61, the junction B1 is connected to a bias current resistor 75 and an ESD (Electrostatic Discharge) protection capacitor 76. That is, the bias current resistor 75 and the ESD protection capacitor 76 have terminals connected to the sensor-side terminal (B1) of the current-voltage converter 61 and the other ends connected to ground. The bias current resistor 75 has a resistance value of, for instance 1 MΩ or more.

Here, with the bias current resistor 75 connected to the junction B1 (the sensor-side terminal of the current-voltage converter 61), the sensor-cell current measured value VS2 can be set to a fixed voltage when measuring the sensor electromotive force in a manner set forth above under a condition where a failure such as disconnection or element cracking is present. In other words, it becomes possible to acquire a value addressing a failure in electromotive force representing the sensor-cell current measured value VS2. That is, under a condition where the failure such as disconnection or element cracking occurs, no electromotive force occurs in the sensor cell 35 and the sensor-cell current measured value VS2 (voltage at the junction B1 in the drawing figure) is indefinite. However, with the Is detection circuit section 45 having such a structure incorporating the bias current resistor 75, the sensor-cell current measured value VS2 can be kept at a given voltage (voltage depending on a resistance value of the bias current resistor 75) even under a condition where no sensor electromotive force is present. Accordingly, even if no electromotive force is present, the sensor-cell current measured value VS2 is stable, enabling the detection of the sensor electromotive force in the form of an abnormal value.

With the present embodiment, further, the bias current resistor 75 has a low potential side connected to ground. The present invention is not limited to such a circuit connection and may take a structure such that the low potential side of the bias current resistor 75 is connected to a reference potential kept at a fixed voltage potential. Other alternative structures may include, for instance, a structure in which the bias current resistor 75 has one end connected to a power supply circuit and a structure in which the one end of the bias current resistor 75 is connected to a circuit section that outputs a given voltage ranging from a ground voltage to a power supply voltage.

With the bias current resistor 75 provided in such a structure, a current flows through the bias current resistor 75 accompanied by a reduction caused in the amount of current flowing through the current-voltage converter 61 by that extent. Therefore, the Is detection circuit section 45 may be arranged in a circuit structure in that preliminarily measuring the amount of current flowing through the current-voltage converter 61 allows a component of measured current to be compensated.

The Im detection circuit section 46 has the same circuit structure as that of the Is detection circuit section 45 and, hence, redundant illustration and description of the same are herein omitted. That is, the circuit, shown in FIG. 4, can be also used intact as the Im detection circuit section 46. As shown in FIG. 2, also, the microcomputer 41 outputs a circuit switching signal SG3 for the monitor cell that is applied to the Im detection circuit section 46. Upon receipt of the circuit switching signal SG3, the Im detection circuit section 46 switches to select one of a state of detecting a residual oxygen concentration form a normal operation and a state (state with Current=0 nA) wherein the potential difference across the both terminals of the current-voltage converter is zeroed (in the same manner in which the operation is performed in response to the circuit switching signal SG2). In addition, the Im detection circuit section 46 is arranged to output a monitor-cell current measured value VM1 in place of the sensor-cell current measured value VS1 shown in FIG. 4, while outputting a monitor cell terminal voltage VM2 in place of the sensor-cell terminal voltage VS2. Under a circumstance where the potential difference across the both terminals of the current-voltage converter is zeroed, the monitor cell electromotive force can be measured based on the monitor cell terminal voltage VM2.

As shown in FIG. 2, the microcomputer 41 is applied with the sensor-cell current measured value VS2, output from the Is detection circuit section 45, and the monitor-cell current measured value VS1, output from the Im detection circuit section 46, on the basis of which the microcomputer 41 calculates a (Is−Im) value. Then, the microcomputer 41 fisher calculates a NOx concentration in exhaust gases based on the (Is−Im) value.

Next, a structure of the sensor-cell/monitor-cell protecting circuit section 48 will be described below in detail with reference to FIG. 5. The sensor-cell/monitor-cell protecting circuit section 48 detects power shortages or failures and ground shortages or failures occurring at circuit sections (circuit areas connected to the positive potential common terminal COM+ and the negative terminals SS− and MS−) of the sensor cell 35 and the monitor cell 34 at the positive and negative potential sides thereof. With the present embodiment, the sensor-cell/monitor-cell protecting circuit section 48 corresponds to a "voltage application interrupting means".

Figure 5:
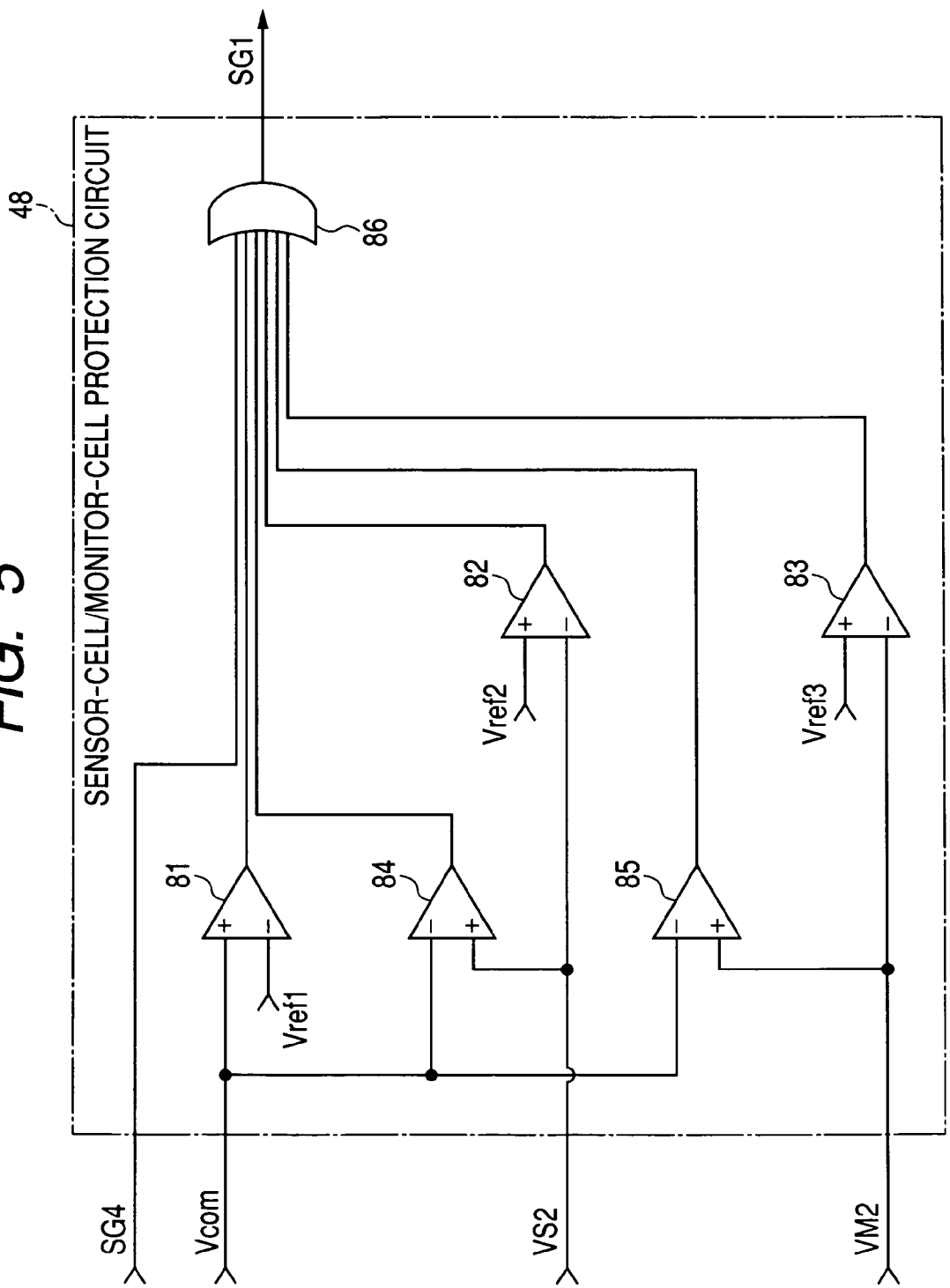
FIG. 5 is a circuit structural view showing a sensor-cell/monitor-cell protecting circuit section shown in FIG. 2.

In FIG. 5, the protecting circuit section 48 is applied with the common terminal voltage Vcom output from the censor-cell/monitor-cell driver circuit section 44, the sensor-cell terminal voltage VS2 output from the Is detection circuit section 45, and the monitor-cell terminal voltage VM2 output from the Im detection circuit section 46. In addition, the protecting circuit section 48 is applied with a failure determining signal SG4 delivered from the microcomputer 41. Although the failure determining signal SG4 will be described later in detail, in brief, the failure determining signal SG4 takes the form of a binary signal with SG4="High" for normal operation and SG4="Low" in the occurrence of a failure. Further, the sensor-cell/monitor-cell protecting circuit section 48 generates the voltage application stopping signal SG1 in response to these various input signals which is applied to the sensor-cell/monitor-cell driver circuit 44. Such a detail will be described below.

The sensor-cell/monitor-cell protecting circuit section 48 includes five comparing circuits 81 to 85, which operate in manners as described below.

The first comparing circuit 81 compares the common terminal voltage Vcom (of 4.4V during normal operation) and a reference voltage Vref1 (of, for instance, 4.6V). In this case, during normal operation, Vcom<Vref1 and the first comparing circuit 81 provides an output with "Low". In contrast, during the occurrence of a failure, Vcom>Vref1 and the first comparing circuit 81 provides another output with "High". If a power shortage occurs at, for instance, an area connected to the common terminal COM+, the first comparing circuit 81 generates an output with "High".

The second comparing circuit 82 compares the sensor-cell terminal voltage VS2 (of 4.0V during normal operation) and a reference voltage Vref2 (of, for instance, 3.8V). In this case, during normal operation, a situation stands for VS2>Vref2 and the second comparing circuit 82 provides an output with "Low". In contrast, during the occurrence of a failure, another situation stands for VS2<Vref2 and the second comparing circuit 82 provides another output with "High". If a ground shortage occurs at, for instance, an area connected to the negative terminal SS−, the second comparing circuit 82 generates an output with "High".

The third comparing circuit 83 compares the monitor cell terminal voltage VM2 (of 4.0V during normal operation) and a reference voltage Vref3 (of, for instance, 3.8V). In this case, during normal operation, a situation stands for VM2>Vref3 and the third comparing circuit 83 provides an output with "Low". In contrast, during the occurrence of a failure, another situation stands for VM2<Vref3 and the third comparing circuit 83 provides another output with "High". If a ground shortage occurs at, for instance, an area connected to the negative terminal MS−, the third comparing circuit 83 generates an output with "High".

The fourth comparing circuit 84 compares the common terminal voltage Vcom and the sensor-cell terminal voltage VS2. In this case, during normal operation, Vcom>VS2 and the fourth comparing circuit 84 provides an output with "low". In contrast, during the occurrence of a failure, Vcom<VS2 and the fourth comparing circuit 84 provides another output with "High". If a ground shortage occurs at, for instance, an area connected to the common terminal COM+ or a power shortage occurs at the negative terminal SS−, the fourth comparing circuit 84 generates an output with "High".

The fifth comparing circuit 85 compares the common terminal voltage Vcom and the monitor cell terminal voltage VM2. In this case, during normal operation, Vcom>VM2 and the fifth comparing circuit 85 provides an output with "Low". In contrast, during the occurrence of a failure, Vcom<VM2 and the fifth comparing circuit 85 provides another output with "High". If the ground shortage occurs at, for instance, the area connected to the common terminal COM+ or a power shortage occurs at the negative terminal MS−, the fifth comparing circuit 85 generates an output with "High".

Although not shown in the drawing, a resistor divider circuit, composed of two resistors, divides a constant voltage Vcc into each of the reference voltages Vref1 to Vref3.

The outputs of the five comparing circuits 81 to 85 and the failure determining signal SG4, output from the microcomputer 41, are input to an OR circuit 86. In this case, if either one of the plural input signals applied to the OR circuit 86 lies at a high level, then, the OR circuit 86 generates a "High" signal as the voltage application stopping signal SG1. If SG1="High", then, the switching circuit 53 of the sensor-cell/monitor-cell driver circuit 44 is opened as set forth above, thereby interrupting the supply of the voltage to the common terminal COM+ (see FIG. 3). That is, it is likely that the sensor cell 35 and the monitor cell 34 encounter the occurrence of the failure such as the power shortage or the ground shortage or, in alternative, the microcomputer 41 outputs the failure determining signal SG4. Under such circumstances, the voltage application to the sensor cell 35 and the monitor cell 34 is interrupted, thereby achieving an affect of protecting these cells. More particularly, this prevents an over current from flowing through the sensor cell 35 and the monitor cell 34, thereby enabling the suppression of damage to the sensing element.

Now, description will be made of a first operation executed by the microcomputer 41 to calculate a sensor output compensation value and a second operation to detect a failure. The calculating operation on the sensor output compensation value is an operation in which during in the course of detecting the NOx concentration, an operation is executed to temporarily zero the potential difference across both terminals of the current-voltage converter in the Is detecting circuit section 45 and the Im detecting circuit section 46 during a period in which an operation is executed to calculate an output compensating value (an offset correcting value in particular with the present embodiment) based on a circuit output under such a state. Further, a failure detecting operation is to detect the existence of or nonexistence of a failure, such as a disconnection or element cracking and an element activity deficiency or the like, based on the electromotive forces of the sensor cell 35 or the monitor cell 36 obtained upon temporarily zeroing the terminal potential difference of the current-voltage converters as set forth above.

Figure 6:
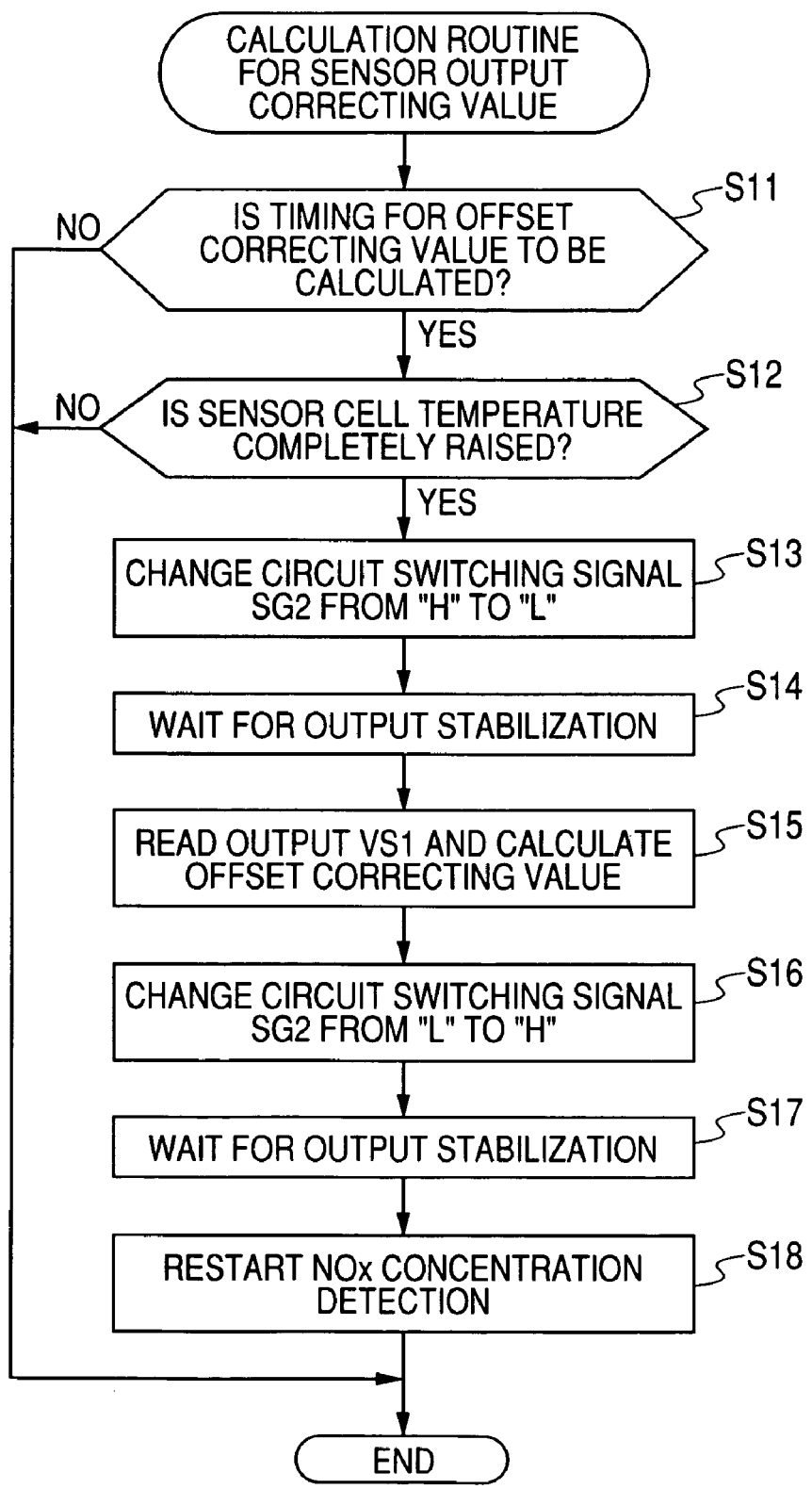
FIG. 6 is a flow chart showing a calculating routine for sensor output correcting value to be executed by a microcomputer shown in FIG. 1.

First, an operating routine for calculating the sensor output compensating value is described below in detail with reference to a flowchart shown in FIG. 6. Also, the operating routine, shown in FIG. 6, is repeatedly executed by the microcomputer 41 on a given time period. Here, description is made of a sequence of calculating the offset correcting value on the output value (VS1) of the Is detection circuit section 45.

In FIG. 6, at step S1, a query is made as to whether operation needs to be executed at current timing to calculate the offset correcting value. With the present embodiment, a calculating period for the offset correcting value to be obtained is set to a value of 10 seconds and, each time the elapse of 10 seconds, the answer to step S11 is yes. The calculating cycle for the offset correcting value may preferably be determined depending on a speed at which a variation occurs in, for instance, temperature of the circuit. If calculating timing for the offset correcting value is present, the operation goes to step S12 wherein a query is made as to whether the sensor cell 35 rises in temperature up to a given activating temperature (of, for instance, of 750° C.). More particularly, a temperature rising state of the sensor cell 35 is determined based on the elapse of time from a startup of an engine, the magnitude of electric power applied to a heater or an impedance detected value related to the sensor cell 35.

If the sensor cell 35 rises in temperature up to a given activating temperature, then, the operation proceeds to step S13, wherein the operation is executed to switch the level of the circuit switching signal SG2 from a high level to a low level. This allows the Is detection circuit section 45 to switch conducting states (in sequence L1→L2 with the present embodiment) of the feedback input electric pathways L1 and L2 connected to the differential amplifier circuit 62. This causes an electric current, flowing through the current-voltage converter 61, to be intentionally set to a value of 0 nA. In consecutive step S14, standby operation is executed until output stabilization is accomplished after the circuit switching signal SG2 is switched from "High" to "Low" level.

After the standby operation has been conducted for a given time interval, in step S15, the operation is executed to read the output VS1 of the differential amplifier circuit 66 and calculate an offset correcting value Foff based on the VS1 value. With the present embodiment, the VS1 value is converted in current at a given time to provide the offset correcting value Foff The offset correcting value Foff is stored in a backup device (such as, for instance, an EEPROM or a backup RAM). In other words, the offset correcting value Foff is stored as a learning value in the backup device and suitably updated.

Thereafter, in step S16, the circuit switching signal S82 is switched from "Low" state to "High" state. This allows the feedback input electric pathway L1 to be connected to the differential amplifier circuit 62 accompanied by a consequence in which the Is detection circuit section 45 is returned to a normal NOx concentration detecting state. In consecutive step S17, standby operation is executed to stabilize the output of the Is detection circuit section 45 after the circuit switching signal SG2 is switched from "Low" state to "High" state. Then, after the standby operation is executed for the given time interval, a normal NOx detecting operation is restarted (in step S18).

The offset correcting value Foff, calculated in such a way discussed above, is suitably used for correcting the sensor cell current Is (in a current converted value of VS1) that is sequentially measured during the operation to detect the NOx concentration. That is, the offset correcting value Foff is subtracted from the sensor cell current Is resulting from the measurement during the NOx concentrating operation, thereby calculating an aft-correction sensor cell current (Aft-Correction Sensor Cell Current=Is−Foff). Then, the NOx concentration is calculated based on the aft-correction sensor cell current.

In actual practice, the operation is executed to calculate the offset correcting values not only for the Is detection circuit section 45 but also for the Im detection circuit section 46 and the NOx concentration is calculated using both of the offset correcting values of these two detection circuit sections 45 and 46. In this case, the offset correcting value for the sensor cell is subtracted from the sensor cell current Is (measured value) to calculate the aft-correction sensor cell current and the offset correcting value for the monitor cell is subtracted from the monitor cell current Im (measured value) to calculate the aft-correction sensor cell current. Then, the NOx concentration is calculated based on a difference (=Aft-Correction Sensor Cell Current−Aft-Correction Monitor Cell Current) between the aft-correction sensor cell current and the aft-correction monitor cell current.

Figure 7A:
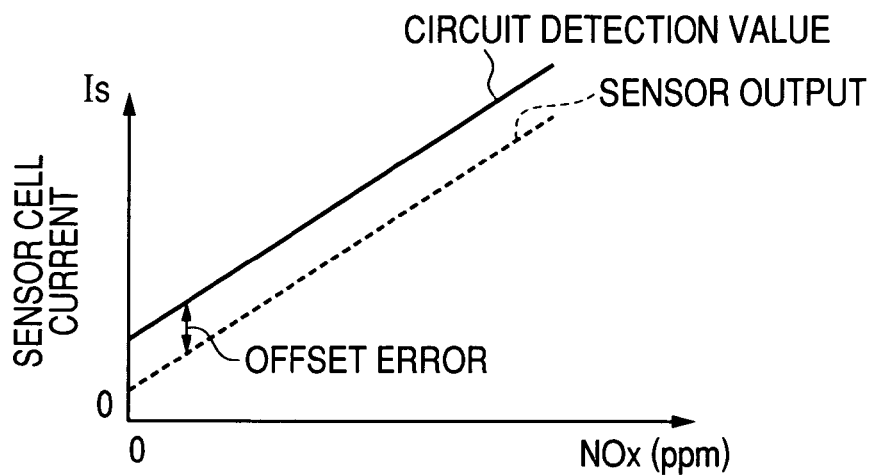
FIG. 7A is a graph showing the relationship between a sensor cell current Is and a NOx concentration.

As shown in FIG. 7A, the NOx sensor circuit 40 encounters the occurrence of offset errors in the sensor cell current Is and the monitor cell current Im, respectively. In FIG. 7A, the term "SENSOR OUTPUT" refers to a current value actually occurring on the sensor element 10 and the term "CIRCUIT DETECTION VALUE" refers to a measured value, measured with the NOx sensor circuit (including the Is detection circuit section 45 and the Im detection circuit section 46), for an actual sensor output.

In FIG. 7A, the CIRCUIT DETECTION VALUE and the SENSOR OUTPUT linearly increase with an increase in the NOx concentration. There is an offset error between the CIRCUIT DETECTION VALUE and the SENSOR OUTPUT.

Figure 7B:
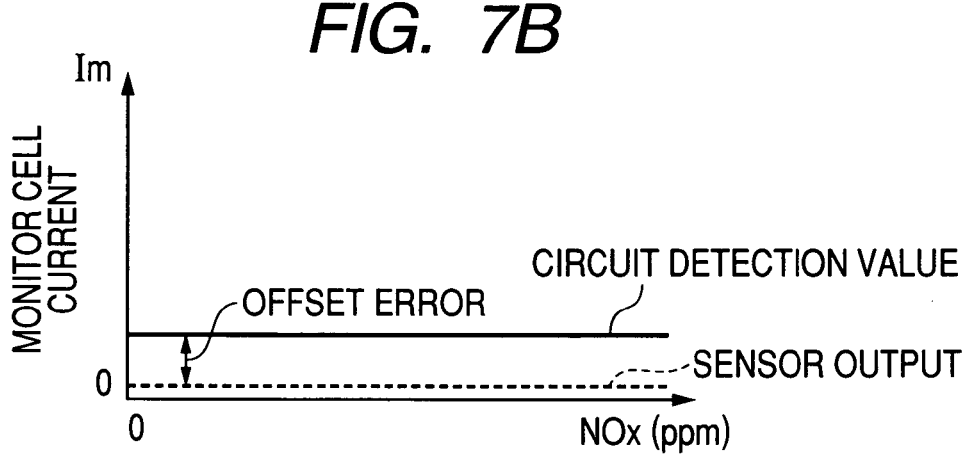
FIG. 7B is a graph showing the relationship between a monitor cell current Im and the NOx concentration.

In FIG. 7B, the CIRCUIT DETECTION VALUE lies at a first monitor cell current Im and the SENSOR OUTPUT lies at a second monitor cell current Im with an offset error intervening therebetween.

Figure 7C:
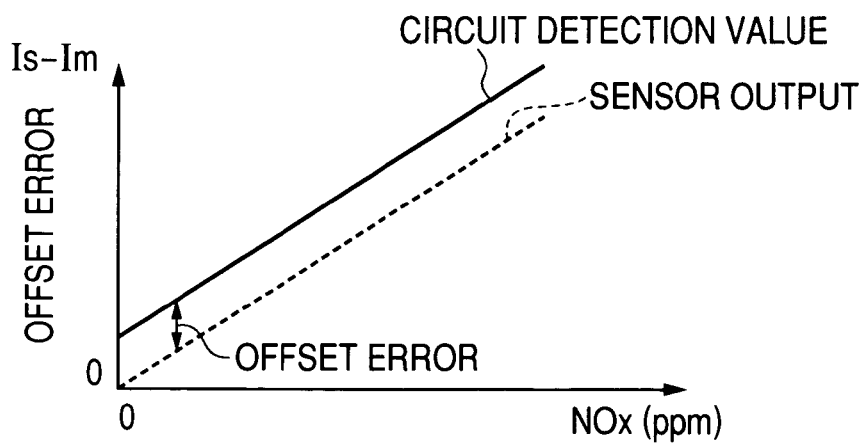
FIG. 7C is a graph showing the relationship between an offset error (Is−Im) and the NOx concentration.

In FIG. 7C, the CIRCUIT DETECTION VALUE and the SENSOR OUTPUT linearly increase with an increase in the offset error. There is an offset error between the CIRCUIT DETECTION VALUE and the SENSOR OUTPUT.

In such a case, the operation is executed to acquire the offset error related to the sensor output as an offset correcting value, which in turn is used for correcting the sensor cell current Is and the monitor cell current Im, respectively. This enables the suppression of a drop in precision of calculating the NOx concentration resulting from the offset error on the circuit detection value.

Figure 8:
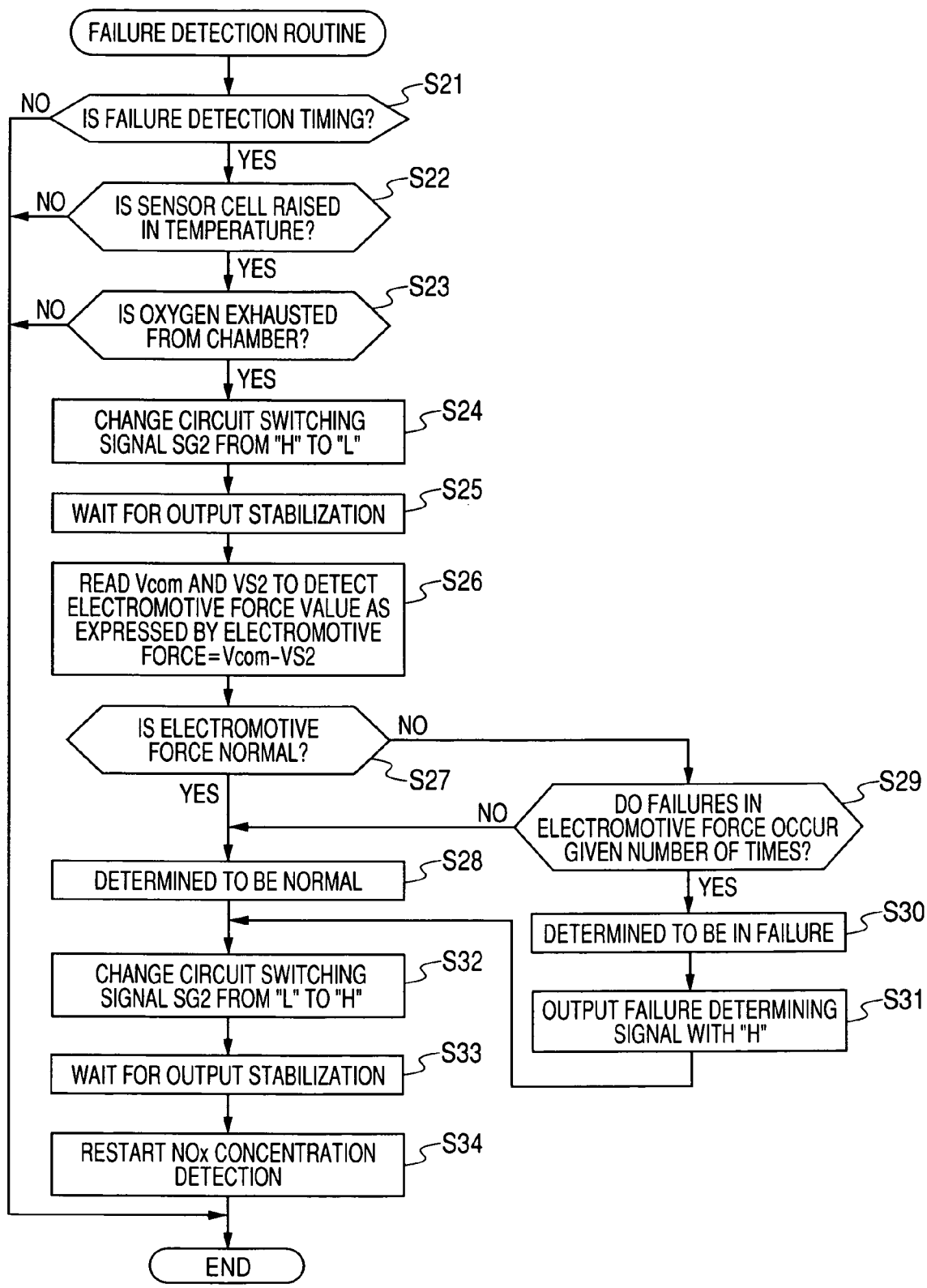

FIG. 8 is a flow chart showing an operating routine for the failure detecting operation executed in response to the sensor cell electromotive force. The present operating routine is repeatedly executed with the microcomputer 41 on a given time period.

In FIG. 8, in step S21, a query is made as to whether failure detecting timing is present. With the present embodiment, a failure detecting cycle is set to 0.5 seconds and, each time 0.5 s elapsed, the answer to step S21 is yes. If failure detecting timing is present, then the operation proceeds to step S22, where a query is made as to whether the sensor cell 35 is raised in temperature up to a given activating temperature (of, for instance, 750° C.) in the same manner as that executed in step S12. Further, in step S23, a query is made as to whether oxygen is adequately exhausted from the chambers 14 and 16 of the sensor element 10 after the engine has started up and whether a residual oxygen concentration lies at a given low oxygen concentration. An exhausting state of residual oxygen is determined based on, for instance, the elapse of time from the startup of the engine.

If the answers to steps S22 and S23 are yes, then, the operation goes to step S24, wherein the circuit switching signal SG2, output to the Is detection circuit section 45, is switched from "High" to "Low" level. This causes the feedback input electric pathways L1 and L2 to be switched (in sequence L1→L2 with the present embodiment) for the differential amplifier circuit 62. This allows electric current, flowing through the current-voltage converter 61, to be intentionally set to 0 nA. In succeeding step S25, the standby operation is executed until the output stabilization is accomplished after the circuit switching signal SG2 is switched from "High" to "Low" level.

Upon the execution of the standby operation for the given time interval, in step S26, the operation is executed to read the common terminal voltage Vcom and the sensor-cell terminal voltage VS2, based on which the electromotive force of the sensor cell 35 is detected. More particularly, subtracting the sensor-cell terminal voltage VS2 (i.e., an electromotive-force measured value on the negative terminal of the sensor cell) from the common terminal voltage Vcom (i.e., an electromotive-force measured value on the positive terminal of the sensor cell) allows an electromotive force value of the sensor cell 35 to be calculated. In addition, at this moment, the electromotive force value of the sensor cell 35 is stored in the backup device (such as, for instance, the EEPROM or backup RAM).

Subsequently, in step S27, a query is made as to whether the electromotive force, detected in step S26, lies in a predetermined normal range. More particularly, the chamber of the sensing element 10 fundamentally remains in a thinned lean state and the electromotive force of the sensor cell 35 takes a voltage value of approximately 0.2V. Thus, the normal range is set to a range (of a value ranging from 0.1 to 0.3V) at $0.2V \pm 0.1V$. However, the normal range may fall in a value ranging from 0.1 to 0.4V in consideration of the fact in that the sensor cell application voltage lies at 0.4V (=4.4−4.0V) during a normal operation.

If the electromotive force falls within the normal range, the operation proceeds to step S28 where a normalcy decision is made with no occurrence of the failure such as disconnection or element cracking or the like. Further, if the electromotive force is out of a normal range, the operation proceeds to step S29 wherein a query is made as to whether failures in electromotive force continuously occur a given number of times. If the failures in electromotive force continuously occur the given number of times, the operation proceeds to step S30 wherein a failure decision is made in the presence of the failure such as disconnection or element cracking or the like.

If the decision is made that the failure such as disconnection or element cracking or the like occurs, then, the operation is executed in step S31 so as to allow the failure determining signal SG4 with a "High" level to be output to the sensor-cell/monitor-cell protection circuit section 48.

Subsequently, in step S32, the operation is executed to switch the circuit switching signal SG2 from "Low" to "High" level. This allows the feedback input electric pathway for the differential amplifier circuit 62 to be returned to "L1" accompanied by an effect in which the Is detection circuit section 45 is returned to the normal NOx concentration detecting state. In consecutive step S33, the standby operation is executed to stabilize the output after the circuit switching signal S82 is switched in sequence "Low"→"High". After the standby operation is executed for the given time interval, the normal NOx concentration detecting operation is restarted (in step S34).

Though not shown in the drawing figure, the monitor cell 34 is arranged to execute the failure detecting operation based on the monitor-cell electromotive force in the same manner as that described above in a sequence similar to that shown in FIG. 8. To explain this briefly, the Im detection circuit section 46 is brought into a state in which the potential difference on both terminals of the current-voltage converter is zeroed, under which the monitor cell voltage is detected suing the monitor-cell terminal voltage VM2. Then, a query is made as to whether the monitor cell electromotive force falls within a normal range (ranging from 0.1 to 0.3 or ranging from 0.1 to 0.4V), upon which the failure decision is made. This allows the monitor cell 34 to detect a failure like disconnection or element cracking or the like.

With the present embodiment of such a structure, the gas sensor control device has various advantages as listed below.

The Is detection circuit section 45 (or the Im detection circuit section 46) is structured to have the switch circuit 71 provided in the electric pathway through which no element current (sensor cell current or the monitor cell current) flows. Even if the switch circuit 71 remains closed, the Is detection circuit section 45 calculates the offset correction value Foff based on the output VS1 (or VM1) of the differential amplifier circuit 66. With such a structure, if the offset error occurs on the NOx sensor circuit 40, it becomes possible to appropriately obtain the offset correction value Foff equivalent to the offset error.

In particular, further, the switch circuit 71 is provided in the electric pathway (feedback input electric pathway L2) through which no element current flows (stated another way, the switch circuit 71 is not provided in the electric pathway through which the element current flows). This avoids an inconvenience with an error occurring on the element current measured value because of a leakage current caused in the switch circuit 71, i.e., more particularly, a leakage current caused in a semiconductor switch such as a transistor or the like. That is, even if the leakage current occurs in the switch circuit 71, no adverse affect occurs as the element current measured value (even if the adverse affect occurs, it extremely remains in a negligible effect). When measuring a weak NOx detection current like that of the structure of the present embodiment, the presence of the error in the current measured value due to the existence of the switch circuit results in an increased adverse affect on NOx concentration detection but such an inconvenience can be avoided.

With such a capability of appropriately calculating the offset correction value Foff and excluding the adverse affect arising from the leakage current flowing through the switch circuit, the NOx concentration can be detected at increased precision. Further, even if the output error occurs in the NOx censor circuit 40 due to temperature characteristics and deterioration with age, the output characteristic can be appropriately addressed, enabling the NOx concentration to be appropriately detected.

With the present embodiment, the structure is arranged such that closing the switch circuit 71 to zero the potential difference on both terminals of the current-voltage converter 61 allows the offset correction value Foff to be calculated based on the output VS1 (or VM1) of the differential amplifier circuit 66 even if the potential difference remains a zeroed state. This enables the offset correction value Foff to be appropriately detected based on the output VS1 (or VM1) under a measuring state with NOx Concentration=0 ppm.

With the switch circuit 71 remained closed, terminal voltages (i.e., common terminal voltage Vcom and sensor-cell terminal voltage VS2), appearing at positive and negative terminals of the sensor cell 35 are measured. Then, the electromotive force of the sensor cell 35 is detected using a difference between the detected terminal voltages (in the same operation as that of the monitor cell 34). This enables the electromotive force to be accurately detected. However, it will be appreciated that the electromotive force can be detected with the use of only the sensor-cell terminal voltage VS2.

The Is detection circuit section 45 (or the IM detection circuit section 46) has the structure in which the two feedback input electric pathways L1 and L2 are provided with the switch circuits 67 and 71, respectively. This allows the switch circuits 67 and 71 to be opened or closed depending on a need to detect a normal NOx concentration or a need to calculate the offset correcting value whereby the operation is executed to properly switch the feedback input electric pathway that lies in a conducting state. With such a structure, suitably switching the feedback input electric pathway to the differential amplifier circuit 62 enables the NOx concentration detection to be temporarily interrupted to execute the calculation on the offset correcting value.

Further, the current-voltage converter 61 is connected to the outside of the negative feedback section of the differential amplifier circuit 62, thereby making it possible to control the output (the voltage of the current-voltage converter 61 at the terminal opposite to the sensor) of the differential amplifier circuit 62. This enables the potential difference on both terminals of the current-voltage converter 61 to be regulated at varying degrees. Accordingly, it becomes possible to zero the potential difference on both terminals of the current-voltage converter 61.

With the Is detecting circuit section 45, the sensor-side terminal of the current-voltage converter 61 is connected to ground (at a reference voltage portion) via the bias current resistor 75. Thus, even if no sensor electromotive force is present, the current-voltage converter 61 ran have a sensor-side terminal voltage kept at a given voltage due to the existence of the bias current resistor 75. Accordingly, even if no electromotive force is present, a circuit output can be stabilized in operation, enabling the sensor electromotive force to be detected as a failure value.

With the present embodiment, the common driver circuit 44 is connected to the sensor cell 35 and the monitor cell 34 at the positive potential electrodes thereof and the negative potential electrodes of the sensor cell 35 and the monitor cell 34 are connected to the Is detection circuit section 45 and the Im detection circuit section 46, respectively, to which the switch circuits 71 are connected. This allows the offset correcting values of the respective detection circuit sections 45 and 46 to be calculated based on the current measured values VS1 and VM1 acquired from the respective detection circuit sections 45 and 46. This enables characteristic variations (circuit errors) of the respective detection circuit sections 45 and 46 to be calculated for each cell. Accordingly, the offset correcting value to be calculated can be further increased in precision than that achieved when the switch circuit is provided in the sensor-cell/monitor cell driver circuit 44 that represents the common driver circuit of the respective cells 34 and 35.

For calculating the sensor output correcting value (see FIG. 6), it is structured such that the offset correcting value Foff is calculated subjected to a state in which the sensor cell 35 (or the monitor cell 34) remains active in temperature. This enables the offset correcting value Foff to be obtained at an increased precision with the circuit output remaining in a stabilized state.

For calculating the sensor output correcting value (see FIG. 6), likewise, it is arranged such that the standby time interval is provided to wait for output stabilization to be obtained during switchover on the opening and closing operations of the switch circuit 67 and 71. This enables the sensor-cell current measured value VS1 to be obtained with the circuit output being stabilized. Thus, it becomes possible to obtain the NOx concentration value and the offset correcting value Foff at increased precisions. In addition, in place of waiting for a given time, the standby operation may be conducted until a varying quantity (variation rate) per time of VS1 reaches a given value or less.

Further, the Is detection circuit section 45 takes the form of a structure arranged to detect the electromotive force of the sensor cell 35 with the switch circuit 71 being closed (in the same manner as that of the Im detection circuit section 46 to detect the electromotive force) upon which the failure determination is made based on such an electromotive force. This makes it possible to appropriately detect the occurrence of a failure when the failure occurs in the from of element cracking, activity defect and disconnection or the like.

The sensor-cell/monitor-cell protection circuit section 48 takes the form of the structure in which the failure is executed based on the common terminal voltage Vcom, the sensor-cell terminal voltage VS2 and the monitor cell terminal voltage VM2 which represent the respective terminal voltages of the sensor cell 35 and the monitor cell 34, respectively (i.e., with the structure arranged to output the failure determining signal SG4 based on the respective terminal voltages in actual practice). This results in a capability of detecting not only the failures such as element cracking, defective activity and disconnection or the like but also failures such as power shortage and ground shortage occurring at the electrodes of the sensor cell 35 and the monitor cell 34.

With the control device of the present embodiment, it is structured that if determination is made that various failures such as disconnections or the like occur, then, the "High" signal is output as the failure determining signal SG4 to allow the sensor-cell/monitor-cell driver circuit section 44 to interrupt the supply of voltage to be applied to the sensor cell 35 and the monitor cell 34. This results in a capability of suppressing an adverse affect on the sensing element arising from continuously applying the voltage to the respective cells during the occurrence of the failure while enabling the protection of the sensing element.

With the NOx sensor circuit 40 with a supposition in that in the first place, a weak current flows, if various failures (such as power shortage and ground shortage especially at the terminals) occur, then an excessive current is caused to flow through the sensing element. This results in an adverse affect of causing a risk of damage to the sensing element and a variation of output characteristic. In this regard, interrupting the application of voltages to the respective cells during the occurrence of the failures, as set forth above, enables the sensing element to be protected.

With the failure detection routine (see FIG. 8) arranged to detect the sensor electromotive force subjected to the presence of a state in which the sensor cell 35 (or the monitor cell 34) has an activity in temperature and the presence in which after startup of the engine, oxygen inside the chambers 14 and 16 of the sensing element 10 is adequately exhausted. This enables the sensor electromotive force to be appropriately detected accompanied by an increase in precision of the operation to detect the failures.

With the failure detection routine (see FIG. 8), likewise, the standby time interval is provided to wait for the output stabilization during the switchover to open or close the switch circuits 67 and 71. This enables the sensor electromotive force to be detected in a stabilized state, thereby increasing precision of detecting the failures. In addition, in place of waiting for a given time, the standby operation may be conducted until a varying quantity (variation rate) per time of VS1 reaches a given value or less.

Second Embodiment

A circuit structure of an IS detection circuit section forming a gas sensor control device of a second embodiment according to the present invention will be described below with a focus on points different from that of the first embodiment.

With the gas sensor control device of the present embodiment, an Is detection circuit section 45A (or an Im detection circuit section 46A) is rendered to assume one state (referred to as a "first state" for the sake of convenience), in which a potential difference across both terminals of a current-voltage converter is zeroed, and the other state (referred to as a "second state" for the sake of convenience) in which the potential difference across the both terminals of the current-voltage converter takes a value other than the zeroed level. The gas sensor control device of the present embodiment acquires outputs of the Is detection circuit section 45A (or the Im detection circuit section 46A) under such first and second states to calculate a gain correcting value as a current correcting value based on these outputs resulting from these first and second states.

With the gas sensor control device of the present embodiment, the Is detection circuit section 45A has a circuit structure as shown in FIG. 9A. The circuit structure, shown in FIG. 9A, includes the circuit structure, shown in FIG. 4, a part of which is modified. Thus, like or corresponding component parts bear like reference numerals. The Is detection circuit section 45A of the present embodiment differs from the Is detection circuit section 45 shown in FIG. 4 in respect of features described below. That is, the Is detection circuit section 45A, shown in FIG. 9A, includes a voltage output circuit 92, acting as a "voltage generating section", which is connected to a "−" input terming of the differential amplifier circuit 62. This allows a voltage output from the voltage output circuit 92, to be input to the differential amplifier circuit 62 during the calculation of the current correcting value, thereby causing the potential difference across both terminals of the current-voltage converter 61 to be set to a given value (≠zero).

With the Is detection circuit 45A shown in FIG. 9A, the positive terminal of the differential amplifier circuit 62 is connected to ground via a capacitor C0, This suppresses a variation in voltage of the gas sensing element 10 due to a spike or a surge voltage occurring during the turning-off of the switch 71.

Figure 9B:
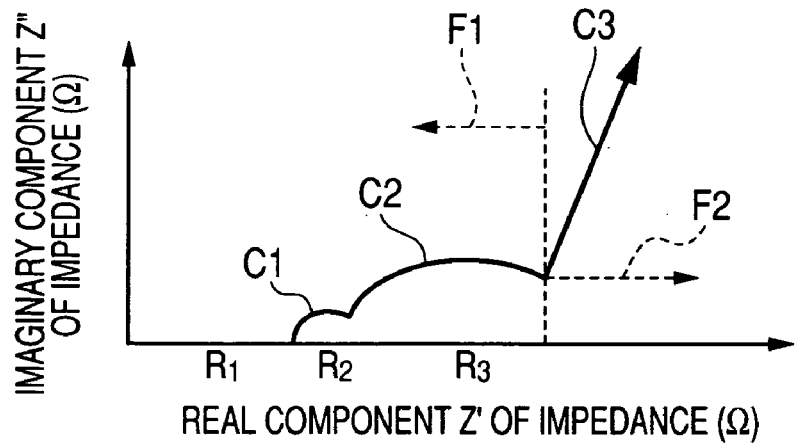
FIG. 9B is a graph showing a frequency dependency result on impedance of the sensor cell when applied with an alternating current voltage at varying frequencies.

FIG. 9B is a graph showing a frequency dependency result on impedance of the sensor cell 35 of the gas sensing element 110 when applied with an alternating current voltage at varying frequencies with a horizontal axis representing a real component Z' of impedance (Ω) and a vertical axis representing an imaginary component Z" of impedance (Ω).

In FIG. 9B, $R_1$ represents an impedance on a real component of the censor cell 35 when the censor cell 35 is applied with an alternating current voltage having a high frequency under which diffusion of $O^{2-}$ occurs with the occurrence of a transfer of electrons; C1 represents a curve covering an impedance $R_2$ on the real component of the censor cell 35 in which grain boundary diffusion of $O^{2-}$ occurs; C2 represents a curve covering an impedance $R_3$ on the real component of the censor cell 35 in which adsorption and dissociation occur with the occurrence of surface diffusion of $O^{2-}$; and C3 represents a curve covering an impedance Z' on the real component of the censor cell 35 in which gas diffusion occurs with the gas sensing element applied with the alternating current voltage having a low frequency. In FIG. 9B, further, F1 represents a frequency range in which an electrode reaction of the sensor cell 35 composed of the solid electrolyte body 21 and the pair of electrodes 37 and 38 and a frequency characteristic of zirconia dominantly appear; and F2 represents a frequency range in which gas diffusion occurs.

Figure 9C:
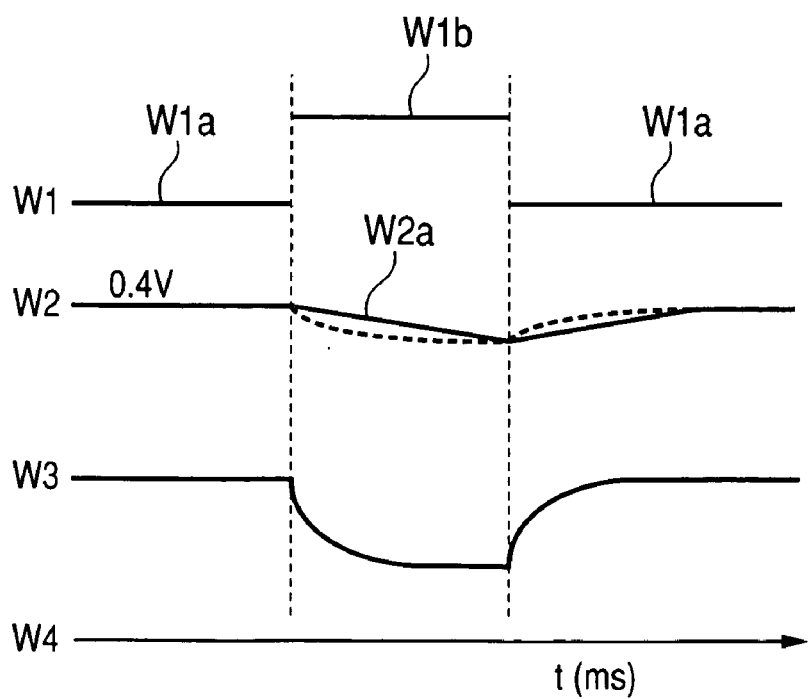
FIG. 9C is a waveform diagram showing the operating state of the censor cell.

FIG. 9C is a waveform diagram showing the operating state of the gas sensing element 110. In FIG. 9C, W1 represents a measuring state under which an output current of the sensor cell 35 is measured with the voltage being applied thereto or a state under which the sensor cell is applied with an electric current to allow a terminal voltage to appear at a given value. W1$a$ indicates time in which the voltage is applied to the sensor cell 35 and W1$b$ indicates that no voltage is applied to the sensor cell 35 to cause an electromotive force to occur between the electrodes of the sensor cell 35. W2 indicates a voltage of 0.4 V applied across the pair of electrodes 37 and 38 of the sensor cell 35 (see FIG. 1) and W2$a$ indicates an electromotive force occurs in the sensor cell 35, and W3 represents a waveform indicating a cell current (element current) flowing through the sensor cell 35; and W4 represents time t(ms).

During a period of W1$b$, the electric current, flowing through the pair of electrodes of the sensor cell 35, is zeroed (for the electromotive force to be measured) with the operation of the circuit described above. The waveforms W2 and W3 indicate a variation in terminal voltage and a variation in element current (cell current) with the electric current flowing through the sensor cell 35 being zeroed with the circuit. With the electric current flowing through the sensor cell 35 being switched to be zeroed, the terminal voltage of the sensor cell 35 results in a variation in voltage caused in the sensor cell 35 due to the occurrence of electromotive force.

More particularly, the feedback input electric pathway L1 is connected to the "−" input terminal of the differential amplifier circuit 62 to which the voltage output circuit 92 is connected via the switch circuit 91. The voltage output circuit 92 is structured of a resistor voltage divider circuit including two resistors with which the fixed voltage Vcc is divided to provide a resulting voltage VX2. Also, a switch circuit 93 is connected to the feedback input circuit L1.

The switch circuits 91 and 93, additionally provided in the circuit shown in FIG. 9A, are arranged to be turned on or turned off (closed or opened) in response to a circuit switching signal SG5 of a binary value of "High" and "Low" input from the microcomputer 41 under a circumstance where the circuit switching signal SG2 is a "Low" signal (i.e., when the switch circuit 67 of the feedback input electric pathway L1 is opened and the switch circuit 71 of the feedback input electric pathway L2 is closed). The circuit switching signal SG5 is input intact to one switch circuit 93 and input to the other switch circuit 91 via an inverting circuit 94.

With the gas sensor control device of the present embodiment, if SG5="H", the switch circuit 93 is closed and the switch 91 is opened. On the contrary, if SG5="L", the switch circuit 93 is opened and the switch 91 is closed. In summary, the switches 91 and 93 are opened or closed at inverted opening and closing time periods.

Here, description will be made of operations executed under a circumstance with SG5="H" and SG5="L" based on the premise of a situation with SG2="L" (with the switch circuit 67 being opened and the switch circuit 71 being closed). It will be appreciated that SG5="H" corresponds to a "first state" and SG5="L" corresponds to a "second state".

If SG5="H", the "−" input terminal of the differential amplifier circuit 62 and the voltage output circuit 92 are disconnected from each other. In such a case, the circuit operation occurs in the same manner as that described with reference to the operation with SG2="L" in FIG. 4. That is, the differential amplifier circuit 62 regulates the voltage of the current-voltage converter 61 at the terminal (the junction B2) opposite to the sensor. This causes the potential difference across both terminals of the current-voltage converter 61 to be zeroed, so that no current flows through the current-voltage converter 61 (as expressed as Current=0 nA). Accordingly, the differential amplifier circuit 66 provides the output VS1 that remains at a value equivalent to a circuit output error under a detecting state with NOx concentration=0 [ppm] (to be equal to the offset value).

Further, if SG5="L", the "–" input terminal of the differential amplifier circuit 62 and the voltage output circuit 92 are connected to each other. In such a case, the differential amplifier circuit 62 regulates the voltage of the current-voltage converter 61 at the terminal (the junction B1) closer to the sensor. This causes the voltage of the current-voltage converter 61 at the terminal (junction B2) opposite to the sensor to lay at a level causing a given voltage potential (=a voltage corresponding to VX2) with respect to the sensor-side terminal (junction B1) of the current-voltage converter 61. When this takes place, the potential difference across the both terminals of the current-voltage converter 61 represents a supposed value depending on the voltage VX2. Such a state corresponds to a state under which a preliminarily determined NOx concentration ($\alpha$ [ppm]) is detected. Accordingly, the output VS1 of the differential amplifier circuit 66 at instant time corresponds to a circuit output error under the detecting state of NOx Concentration=$\alpha$ [ppm].

The output VS1 is obtained in the first state equivalent to the status with NOx concentration=0 [ppm] at which the output VS1 is also obtained in the second state equivalent to the status with NOx concentration=$\alpha$ [ppm]. A gain error can be obtained using these outputs.

Next, the operation of the microcomputer 41 will be described below to explain how the sensor output correcting value is calculated.

Figure 10:
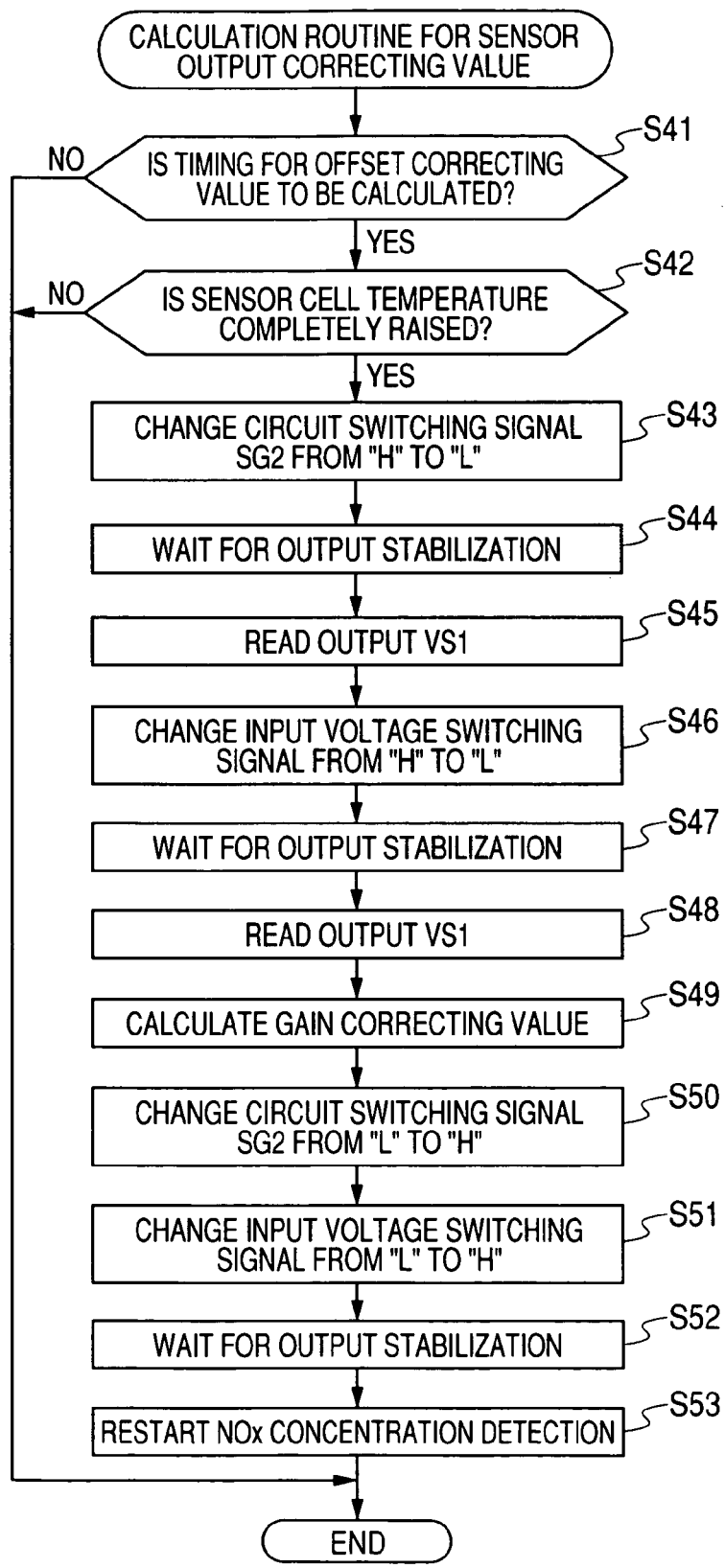
FIG. 10 is a flow chart showing a calculation routine for a sensor output correcting value to be executed for the Is detecting circuit section of the second embodiment shown in FIG. 9.

FIG. 10 is a flow chart showing a routine of the operation to calculate the sensor output correcting value in accordance with the present embodiment. With the present routine, a gain correcting value is calculated as the sensor output correcting value. Also, the routine shown in FIG. 10 is repeatedly executed with the microcomputer 41 at a given time period. Here, description is made of how the gain correcting value is calculated for the output value (VS1) of the Is detection circuit section.

In step S41 in FIG. 10, a query is made as to whether a current time belongs to a calculating timing for the gain correcting value. With the present embodiment, a correction value calculating cycle is set to 10 seconds and each time 10 seconds elapses, step 41 is made positive. If the current time belongs to the calculating timing for the gain correcting value, the operation goes to step S42, wherein a query is made as to whether the sensor cell 35 is raised in temperature up to a given activating temperature (of, for instance, 750° C.). More particularly, the temperature rising state of the sensor cell 35 is determined based on a time elapsed from the engine startup or an impedance detected value of the sensor cell 35.

If the sensor cell 35 is raised in temperature up to a given activating temperature, then, the operation proceeds to step S43, wherein the circuit switchover circuit SG2, output to the Is detection circuit section 45, is switched from "H" to "L". This allows the Is detection circuit section 45 to switch the conducting state (here, from L1→L2) of the feedback input electric pathway L1 and L2 for the differential amplifier circuit 62 accompanied by an effect in which the electric current, flowing through the current-voltage converter 61, is intentionally set to 0 nA. When this takes place, also, the input voltage switchover signal SG5 remains intact to be "High" signal in the "first state" set forth above. In succeeding step S44, a standby operation is executed to wait for stabilizing an output after the circuit switchover circuit SG2 is switched in conducting state from High→Low. After a given time interval has elapsed in standby operation, the operation is executed in S45 to read the output VS1 of the differential amplifier circuit 66. The output VS1, read in step S45, is equivalent to the offset error and it may suffice for the offset correcting value Foff to be calculated based on the VS1 (like an effect achieved in step S15 in FIG. 6).

Subsequently, in step S46, the input voltage switchover signal SG5 is switched from "H" to "L". This allows the Is detection circuit section 45 to be placed in the "second state" under which the "–" input terminal of the differential amplifier circuit 62 and the voltage output circuit 92 are connected to each other. In consecutive step S47, the standby operation is executed to wait for the output stabilization after the circuit switchover circuit SG2 is switched in conducting state from High→Low. After a given time interval has elapsed in standby operation, the operation is executed in S48 to read out the output VS1 of the differential amplifier circuit 66 again.

Thereafter in step S49, a gain correcting value Fgain is calculated based on the output VS1, read in step S45 (that is, the VS1 value read in the first state) and the output VS1, read in step S48 (that is, the VS1 value read in the second state) for storage in the backup device (such as, for instance, EPROM and backup RAM). In other words, the gain correcting value Fgain is stored in the backup device as a learning value to be updated at suitable timing.

Here, the two sensor outputs VS1 represent circuit outputs measured under the state of detecting various NOx concentrations and the use of these binary values enables a sensitivity (gain) of the sensor output for the NOx concentration to be calculated. When this takes place, the supposed NOx concentration in the first state is 0 [ppm] and the supposed NOx concentration in the second state is $\alpha$ [ppm]. Assuming that the sensor output VS1 in the first state is Is1 and the current converted value of the sensor output VS1 in the second state is Is2, then, the gain correcting value Fgain is calculated in a manner described below.

$$Fgain = (Is2 - Is1)/(\alpha - 0)$$
$$= (Is2 - Is1)/\alpha$$

Subsequently, in steps S50 and S51, the input voltage switchover signal SG2 is switched from "L" to "H" and the input voltage switchover signal SG5 is switched from "L" to "H". This allows feedback input electric pathway to the differential amplifier circuit 62 to be switched to L1, under which the "–" input terminal of the differential amplifier circuit 62 and the voltage output circuit 92 are disconnected from each other accompanied by a consequence in which the Is detection circuit section 45 is returned to a normal NOx concentration detecting state.

In succeeding step S52, the standby operation is executed until the output stabilization is obtained after the circuit switching signal SG2 is switched from "L" to "H" and the circuit switching signal SG5 is switched from "L" to "H". After an elapse of a given time interval in the standby operation, the normal NOx concentration detecting operation ids restarted (in step S51).

The gain correcting value Fgain, calculated in such a way described above, is suitably used in correcting the sensor cell current Is (current conversion value of VS1) measured in a sequence. That is, the gain correcting value Fgain is subtracted from the sensor cell current Is, measured when detecting the NOx concentration, allows an aft-correction sensor cell current to be calculated (in a manner as expressed as Aft-correction sensor cell current=Is−Fgain). Then, the NOx concentration is calculated based on the aft-correction sensor cell current.

In actual practice, not only the Is detection circuit section 45 but also the Im detection circuit section 46 execute the calculation on the gain correcting value and the NOx concentration is calculated using both of the gain correcting values delivered from the Is detection circuit section 45 and the Im detection circuit section 46. In this case, the gain correcting value for the sensor cell is subtracted from the sensor cell current Is (measured value) to calculate the aft-correction sensor cell current. Likewise, the gain correcting value for the monitor cell is subtracted from the monitor cell current Im (measured value) to calculate the aft-correction monitor cell current. Then, the NOx concentration is calculated based on a difference (=Aft-Correction Sensor Cell Current−Aft-Correction Monitor Cell Current) between the aft-correction sensor cell current and the aft-correction monitor cell current.

Figure 11A:
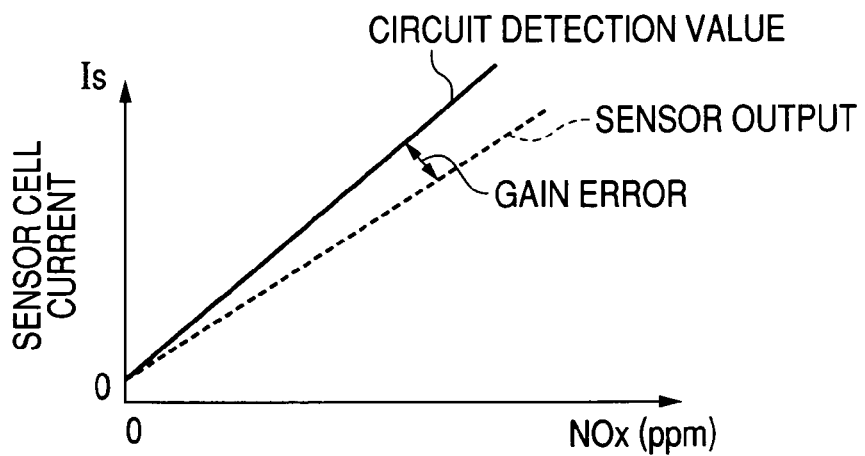
FIG. 11A is a graph showing the relationship between a sensor cell current Is and a NOx concentration with a view to illustrate a gain error.
Figure 11B:
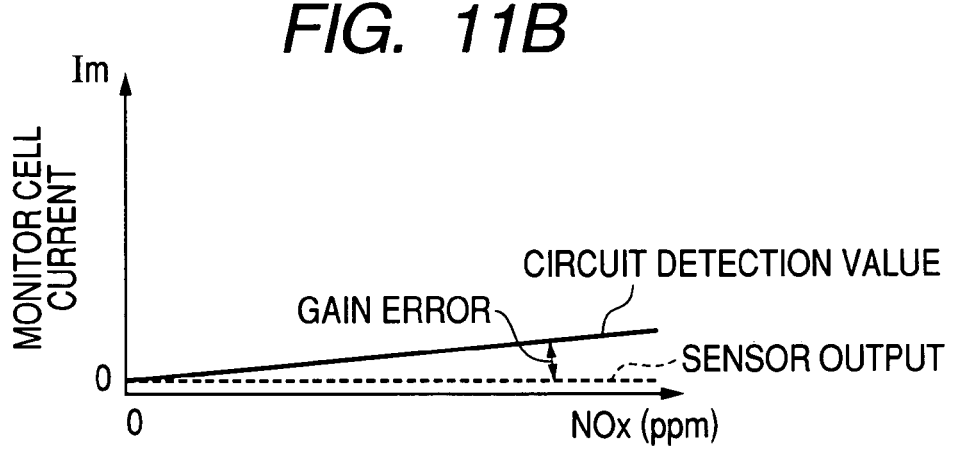
FIG. 11B is a graph showing the relationship between a monitor cell current Im and the NOx concentration with a view to showing the gain error.
Figure 11C:
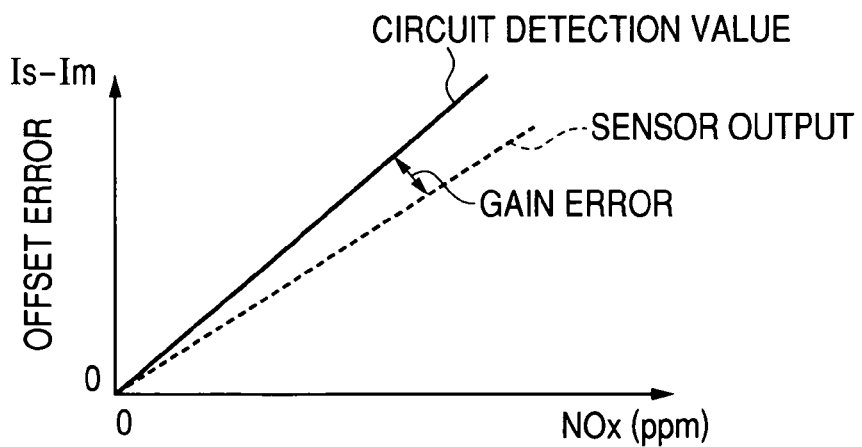
FIG. 11C is a graph showing the relationship between an offset error (Is−Im) and the NOx concentration with a view to showing the gain error.

As shown in FIG. 11, with the NOx sensor circuit 40, a gain error (Is−IM) occurs between the sensor cell current Is and the monitor cell current Im, respectively. In FIG. 11, the term "SENSOR OUTPUT" refers to a current value actually occurred in the sensing element 10 and the term "CIRCUIT DETECTION VALUE" refers to a measured value measured by the NOx sensor circuit 40 (including the Is detection circuit section 45 and the Im detection circuit section 46) in terms of an actual sensor output.

In such a case, the gain error for the sensor output is acquired as the gain correcting value for correcting the sensor cell current Is and the monitor cell current Im using such a gain corrected value. This suppresses a drop in precision of the NOx concentration resulting from the gain error of the circuit detection value.

The NOx censor circuit of the second embodiment has various advantages listed below.

The NOx censor circuit is structured in circuit arrangement so as to acquire the outputs VS1 in the first state equivalent to NOx Concentration=0 and in the second state equivalent to NOx Concentration=α to calculate the gain correcting value Fgain based on the respective outputs. This makes it possible to appropriately obtain the gain correcting value Fgain equivalent to the gain error caused in the NOx sensor circuit 40. In addition, like the first embodiment, no switch circuit is provided on the electric pathway through which the element current (sensor cell current and the monitor cell current) flows. Thus, it becomes possible to avoid an inconvenience in which an error occurs in the element current measured value due to the leakage current caused in the switch circuit.

The gain correcting value Fgain can be properly calculated in a manner set forth above to eliminate an adverse affect arising form the leakage current caused in the switch circuit. This results in a capability of increasing a precision to detect the NOx concentration. Further, even if the output error occurs in the NOx sensor circuit 40 due to the temperature characteristic and temporal change and a variation occurs in such an output error, the output characteristic can be appropriately addressed, while properly enabling the measurement of the NOx concentration.

For the structure causing a given potential difference between both terminals of the current-voltage converter 61, the voltage output circuit 92 is connected to the "−" input terminal of the differential amplifier circuit 62. This causes the potential difference to occur between the both terminals of the current-voltage converter 61 in line with the output voltage of the voltage output circuit 92, making it possible to set the potential difference between the both terminals to an arbitrary level.

Further, in detecting the NOx concentration, those which can be a reference concentration is present only when NOx Concentration=0 ppm under an atmospheric condition. In this case, although it is difficult to calculate the gain correcting value with only the current measuring value where NOx Concentration=0 ppm, shifting the first state to the second state makes it possible for the NOx sensor to obtain the gain correcting value.

(Other Modifications)

The present invention is not limited to the structures of the various embodiments set forth above and may be implemented in modification described below.

With the various embodiments described above, the is detection circuit section 45 takes the form of a structure including an "applied voltage setting circuit" composed of the differential amplifier circuit 62. In an alternative, the applied voltage setting circuit may be comprised of a noninverting amplifier circuit. A circuit structure, shown in FIG. 12, will be described below with a focus on a point different from FIG. 4. Like corresponding parts bear like numerals. With the circuit structure shown in FIG. 12, further, the noninverting circuit is adopted as the applied voltage setting circuit with an alteration made in structure related to a voltage input.

Figure 12:
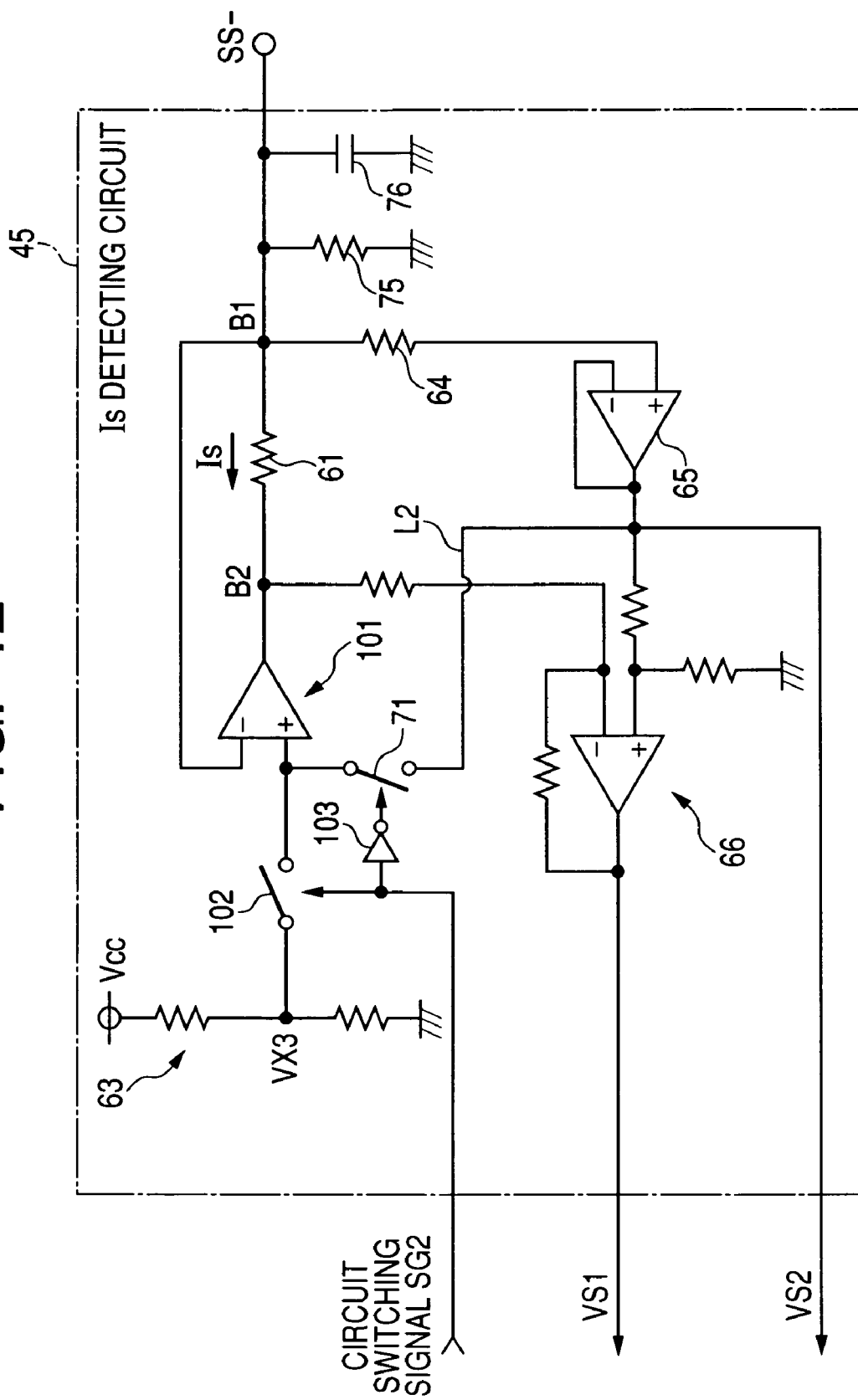
FIG. 12 is a circuit structural view of an Is detecting circuit section of a gas sensor control device of still another embodiment according to the present invention.

With the circuit structure shown in FIG. 12, the noninverting amplifier circuit 101 is provided as the applied voltage setting circuit. The noninverting amplifier circuit 101 has a "−" input terminal connected to the sensor-side terminal (junction B1) of the current-voltage converter 61 and a voltage at the junction B1 is kept at a voltage at a "+" input terminal of the noninverting amplifier circuit 101. A voltage divider point of the resistor voltage divider circuit 63 is connected to the "+" input terminal of the noninverting amplifier circuit 101 via a switch circuit 102, to which an output terminal of a voltage follower 65 is connected via the switch circuit 71.

The switch circuits 102 and 71 are structured in arrangement to be turned on or turned off (closed and opened) in response to the circuit changeover signal SG2 input from the microcomputer 41. The circuit changeover signal SG2 is applied intact to one terminal of the switch circuit 71 and applied to the other switch circuit 71 via the inverting circuit 103.

With the present modified form, if SG2="H", the switch circuit 102 is closed and the switch circuit 71 is opened so that a divided voltage VX3 of the resistor voltage divider circuit 63 is input to the "+" input terminal of the noninverting amplifier circuit 101. Further, if SG2="L", the switch circuit 102 is opened and the switch circuit 71 is closed so that an output of the voltage follower 65 is input to the "+" input terminal of the noninverting amplifier circuit 101. In summary, the switch circuits 102 and 71 are opened and closed with opening and closing time period being reversed in mode, resulting in a structure in which an input voltage of the noninverting amplifier circuit 101 is altered.

With such a circuit structure, when detecting the NOx concentration in normal time, the circuit switching signal SG2 is formed in a "High" signal and the voltage VX3 is applied to the negative terminal SS−. This allows the sensor cell current Is to be measured depending on the NOx concentration in exhaust gases. On the contrary, when calculating the offset correcting value, the circuit switching signal SG2 is formed in a "Low" signal and the output VS2 of the voltage follower 65 is applied to the "+" input terminal of the noninverting amplifier circuit 101 via the feedback input electric pathway L2. By so doing, the potential difference between both terminals of the current-voltage converter 61 can be zeroed in a state with no current flowing through the current-voltage converter 61 (Current=0 nA). Accordingly, the offset correcting value can be calculated in response to the sensor output VS1 occurring at the instant time. In addition, the sensor electromotive force can be detected in response to the sensor-cell terminal voltage VS2.

With the first embodiment, the circuit structure is arranged to allow the sensor-cell/monitor-cell driver circuit section 44 to interrupt the voltage application for protecting the sensor when various failures such as disconnection or the like occur. Such a circuit structure may be altered in other structure. More particularly, the sensor-cell/monitor-cell driver circuit section 44 allows the protector resistor 54 to have a large resistor value (in the order of approximately several 100 kΩ to 1 MΩ) in order to be limited with a predetermined upper limit current (such as for instance aging current). In an alternative, a current output of the operating amplifier 52 is limited. With such a structure, the maximum current, flowing through the sensor cell 35, is limited to protect the sensing element even if failures such as the power supply shortage and ground shortage or the like occur at the negative terminal of the sensor cell 35. In this case, it may be preferred to take a structure in which the cell applied voltage is restricted below an aging voltage for adjusting the sensor characteristic.

With the various embodiments set forth above, it is structured to incorporate the voltage follower 65 in the electric pathway through which the sensor-side terminal of the current-voltage converter 61 and the differential amplifier circuit 62 are connected to each other with a view to providing a structure not to cause the element current to flow through the feedback input electric pathway L2 in the Is detection circuit section 45. In an alternative, the voltage follower 65 may be replaced with the noninverting amplifier circuit. That is, in such a case, a situation stands for the switch circuit 71 to be provided in the electric pathway (feedback input electric pathway L2) between the noninverting amplifier circuit and the differential amplifier circuit 62.

With the various embodiments set forth above, the sensor-cell current measured value VS1 and the monitor-cell current measured value VM1 are input to the microcomputer 41 to allow the microcomputer 41 to calculate the (Is−Im) value as described with reference to FIG. 2. Such a structure can be altered in a structure described below. That is, a (Is−Im) calculating circuit section, composed of, for instance, the differential amplifier circuit, is provided to allow the (Is−Im) calculating circuit section to be applied with the sensor-cell current measured value VS1, output from the Is detection circuit section 45, and the monitor-cell current measured value VM1 output from the Im detection circuit section 46. This allows the calculating circuit section to calculate the (Is−Im) value, which in turn is output to the microcomputer 41.

With the second embodiment mentioned above, the circuit structure is arranged such that in calculating the gain correcting value Fgain, the outputs VS1 are acquired for the first state equivalent to a state with the NOx Concentration=0 [ppm] and the second state equivalent to a state with the NOx Concentration=α [ppm] upon which the gain correcting value Fgain is calculated in response to the respective outputs VS1 under such two states. In an alternative, such a circuit structure may be modified such that in addition to the two states, an output VS1 is acquired tinder a third state with a state (of β≠0, α) equivalent to NOx Concentration=β [ppm] to allow the gain correcting value Fgain to be calculated in response to the respective outputs VS1 under such three states.

Further, another alternative may be arranged in structure such that the outputs VS1 are acquired under the two states, i.e., the states equivalents to NOx Concentration=α [ppm] and NOx Concentration=β [ppm], respectively, to allow the gain correcting value Fgain to be calculated in response to the respective outputs VS1 under such two states.

With the various embodiments set forth above, the sensing element is arranged in a so-called three-cell structure comprised of the pump cell, the sensor cell and the monitor cell. Such a structure may be altered. For instance, the sensing element may take a structure composed of a so-called two-cell structure comprised of the pump cell and the sensor cell. In addition, when using the monitor cell (third cell), the monitor cell may be an electromotive cell to output the electromotive force.

A specified component to be detected may be an object except for NOx. For instance, the gas sensor may be altered to detect objects such as HC (Hydro Carbon) and CO (Carbon Monoxide) in exhaust gases. In such a case, the pump cell is arranged to exhaust extra oxygen from exhaust gases and the sensor cell is arranged to decompose HC and CO in gases after extra oxygen is exhausted, thereby detecting a HC concentration and a CO concentration.

The gas sensor control device may be crystallized as a controller for a gas sensor used in an engine of other type such as a gasoline engine except for the diesel engine. The gas sensor may take a structure to detect gases other than exhaust gases and may be of the type that is used in application except for the automobile.

[Gas Sensing Element of First Modified Form]

A gas sensing element 110 of a first modified form will be described below in detail with reference to FIGS. 13 to 16 of the accompanying drawings.

Figure 13:
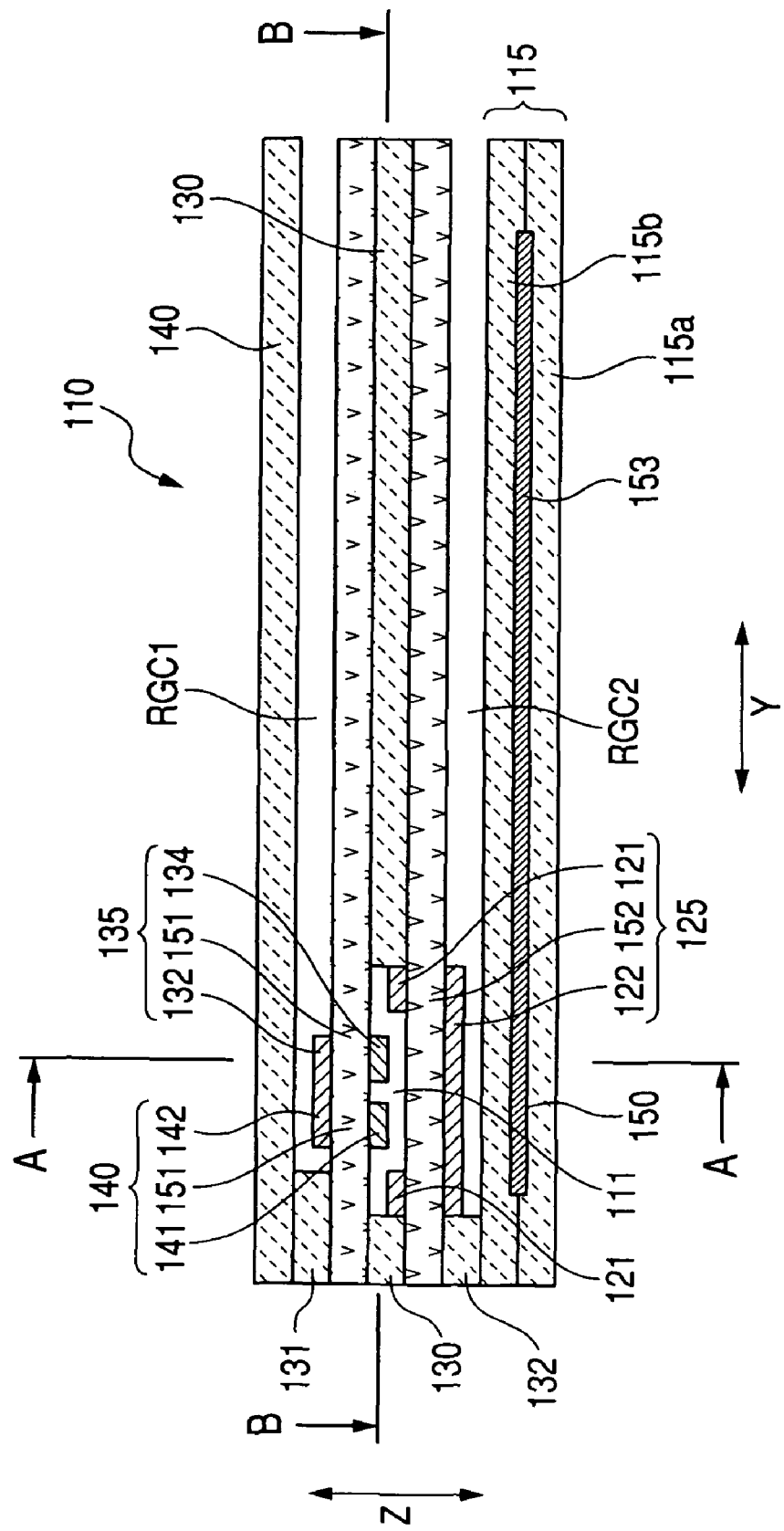
FIG. 13 is a cross sectional view showing a gas sensing element of a first modified form of the gas sensing element shown in FIG. 1.
Figure 14:
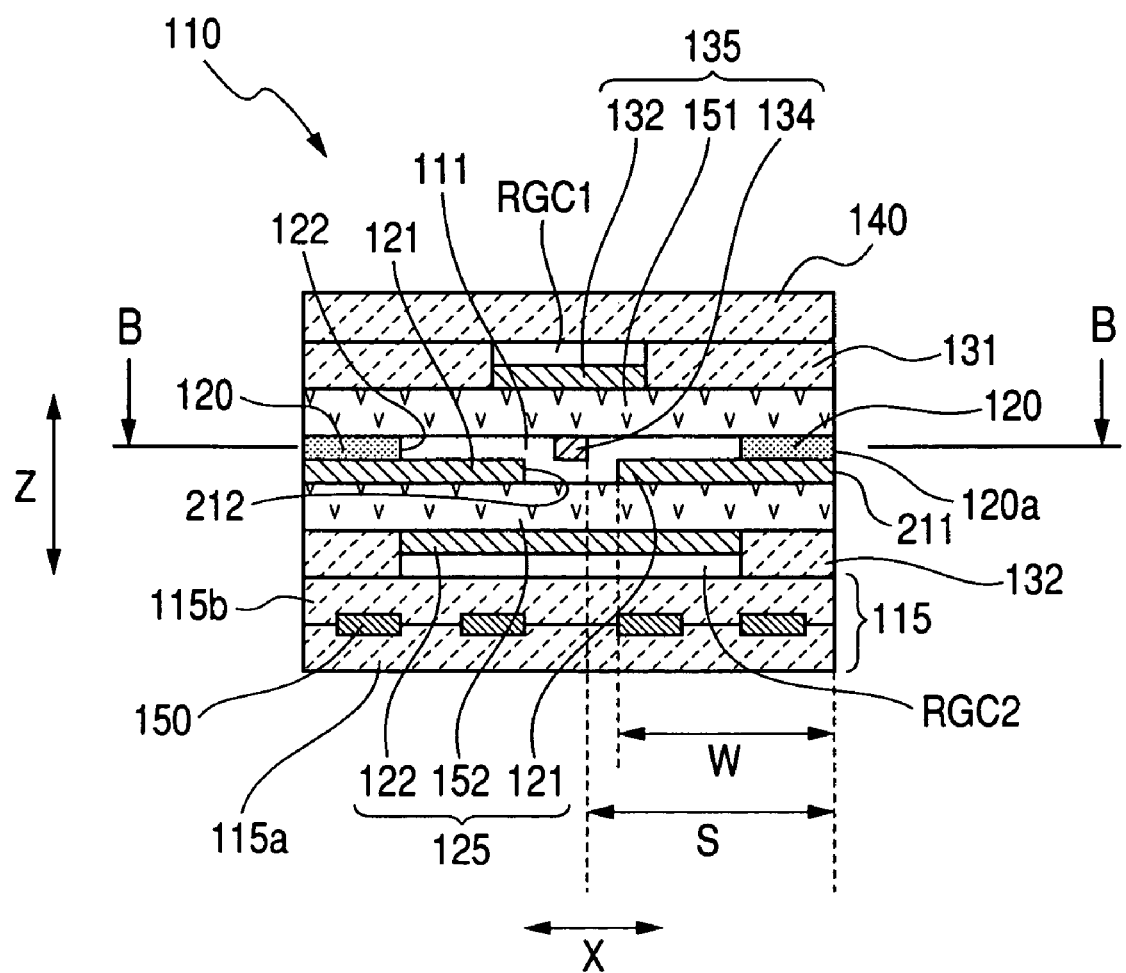
FIG. 14 is a cross sectional view of the gas sensing element taken on line A-A of FIG. 13.

As shown in FIGS. 13 and 14, the gas sensing element 110 includes first and second solid electrolyte bodies 151 and 152, each having oxygen ion conductivity, a measuring gas chamber 111 defined between the first and second electrolyte bodies 151 and 152 for introducing measuring gases, and a diffusion resistance portion 120 for admitting measuring gases to the measuring gas chamber 111 under given diffusion resistance.

Further, the gas sensing element 110 includes a censor cell 135 for detecting a concentration of specified gas contained in measuring gases admitted to the measuring gas chamber 111, an oxygen pump cell 125 for adjusting a concentration of oxygen prevailing in the measuring gas chamber 111, and an oxygen monitor cell 140 for measuring an oxygen concentration in the measuring gas chamber 111.

The sensor cell 135 includes the first solid electrolyte body 151, a measuring electrode 134 formed on the first electrolyte body 151 at one surface thereof in face-to-face relation to the measuring gas chamber 111, and a reference electrode 132 formed on the first electrolyte body 151 at the other surface thereof in pair with the measuring electrode 134.

The oxygen pump cell 125 includes the second solid electrolyte body 152, an inner pump electrodes 121 formed on the second electrolyte body 152 at one surface thereof in face-to-face relation to the measuring gas chamber 111, and an outer pump electrode 122 formed on the second electrolyte body 152 at the other surface thereof in pair with the inner pump electrodes 121.

The oxygen monitor cell 140 includes the first solid electrolyte body 151, an inner monitor electrode 131 formed on the first electrolyte body 151 at one surface thereof in face-to-face relation to the measuring gas chamber 111, and an outer monitor electrode 142 formed on the first electrolyte body 151 at the other surface thereof in pair with the inner monitor electrode 131.

The diffusion resistance portion 120 is formed in a direction perpendicular to a stack direction between the first and second solid electrolyte bodies 151 and 152.

Figure 15:
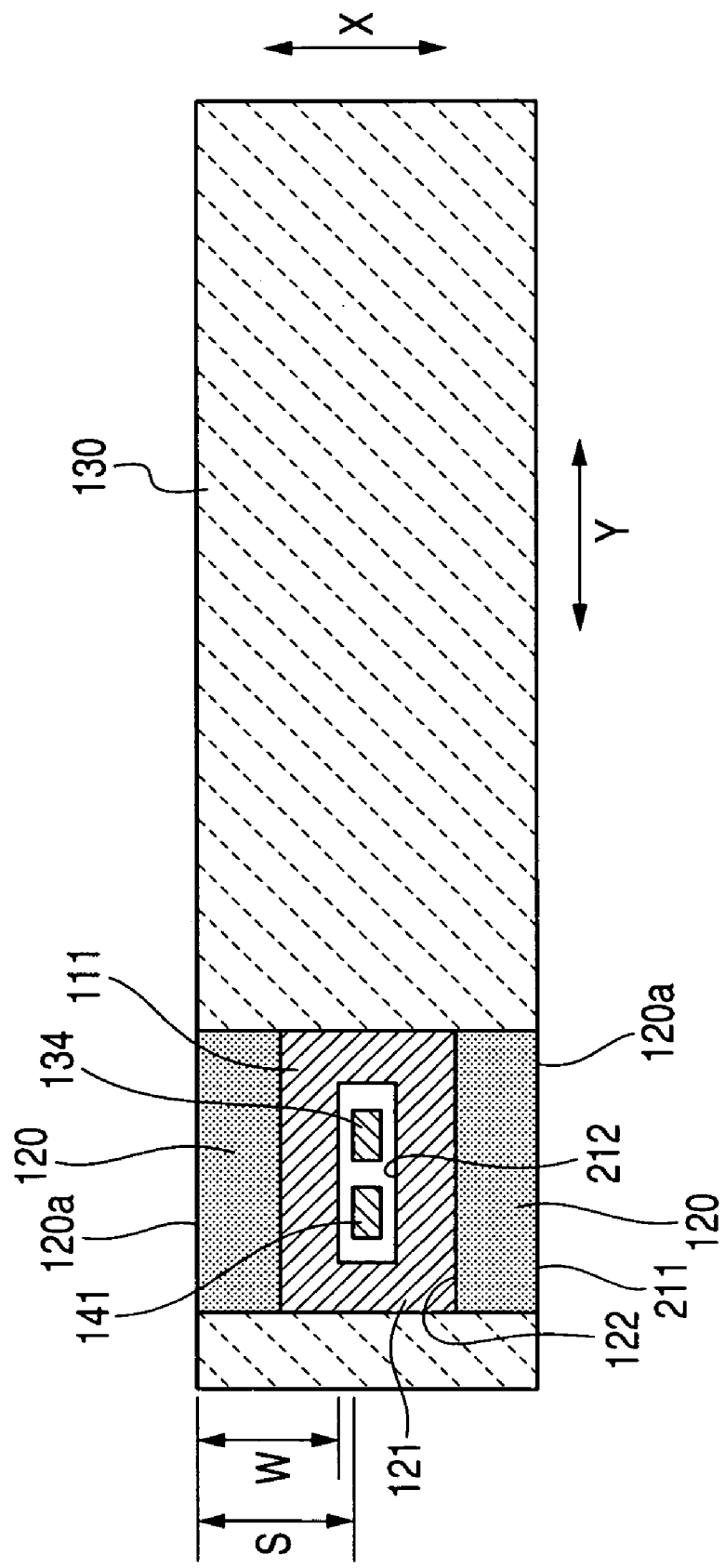
FIG. 15 is a cross sectional view of the gas sensing element taken on line B-B of FIGS. 13 and 14.

As shown in FIG. 15, the measuring electrode 134 is placed in the measuring gas chamber 111 at an area inward of external end wall 212 of the inner pump electrodes 121. In addition, the inner monitor electrode 141 is placed in the measuring gas chamber 111 at an area inward of the internal end walls 212 of the inner pump electrodes 121.

With the present embodiment, further, the measuring electrode 134 and the inner monitor electrode 141 are placed inward of the internal end wall 212 of the inner pump electrodes 121.

As shown in FIGS. 13 and 14, the gas sensing element 110 has a spacer 130 that is sandwiched between the first and second solid electrolyte bodies 151 and 152 to define the measuring gas chamber 111.

Further, a shielding plate 140 is stacked on the first solid electrolyte body 151 at the other surface in opposition to the measuring gas chamber 111 via a spacer 131 for defining a first reference gas compartment RGC1.

Furthermore, a spacer 132 is stacked on the second solid electrolyte body 152 at the one surface thereof in opposition to the measuring gas chamber 111 for defining a second reference gas compartment 102. A ceramic heater 115 is stacked on the second solid electrolyte body 152 via the spacer 132 for heating the oxygen pump cell 125, the sensor cell 135 and the oxygen monitor cell 140.

The reference electrode 132 of the sensor cell 135 and the outer monitor cell electrode 142 of the oxygen monitor cell 140 are composed of a unitized common electrode, which has a function to act as the reference electrode 132 and the outer monitor cell electrode 142. In addition, the reference electrode 132 and the outer monitor cell electrode 142 are formed on the first solid electrolyte body at the other surface thereof in opposition to the measuring electrode 134 and the inner monitor electrode 141 to be exposed to the first reference gas compartment RGC1.

Moreover, the outer pump electrode 122 of the oxygen pump cell 125 is placed on the second solid electrolyte body 152 at the one surface thereof in opposition to the inner pump electrodes 121 to be exposed to the second reference gas compartment 102.

The measuring electrode 134 and the inner monitor electrode 141 are located on the first solid electrolyte body at one surface thereof in areas spaced from each other by a given distance along a longitudinal direction Y of the gas sensing element 110. As shown in FIG. 15, further, the inner pump electrode 121 is formed in an area having a whole circumference so as to surround the measuring electrode 134 and the monitor electrode 141.

As shown in FIG. 14, the diffusion resistance portions 120 and the inner pump electrode 121 are placed adjacent to each other in the stack direction Z. The diffusion resistance portions 120 are formed in a pair at both ends of the measuring gas chamber 111 in a widthwise direction X perpendicular to the stack direction Z and the longitudinal direction Y. With the present embodiment, each of the diffusion resistance portions 120 is made of porous body composed of ceramic such as alumina or the like. The diffusion resistance portions 120 are sandwiched between the inner pump electrode 121 and the first solid electrolyte body 151 and overlap with parts of the inner pump electrode 121 in the stack direction Z.

The shortest distance S between an external end wall 120a of the diffusion resistance portion 120 and the measuring electrode 134 lies in a value ranging from 1 to 3 mm.

The first and second solid electrolyte bodies 151 and 152 have principal components such as zirconia and ceria or the like. In addition, the spacers 130, 131 and 132 have principal components made of alumina.

Figure 16:
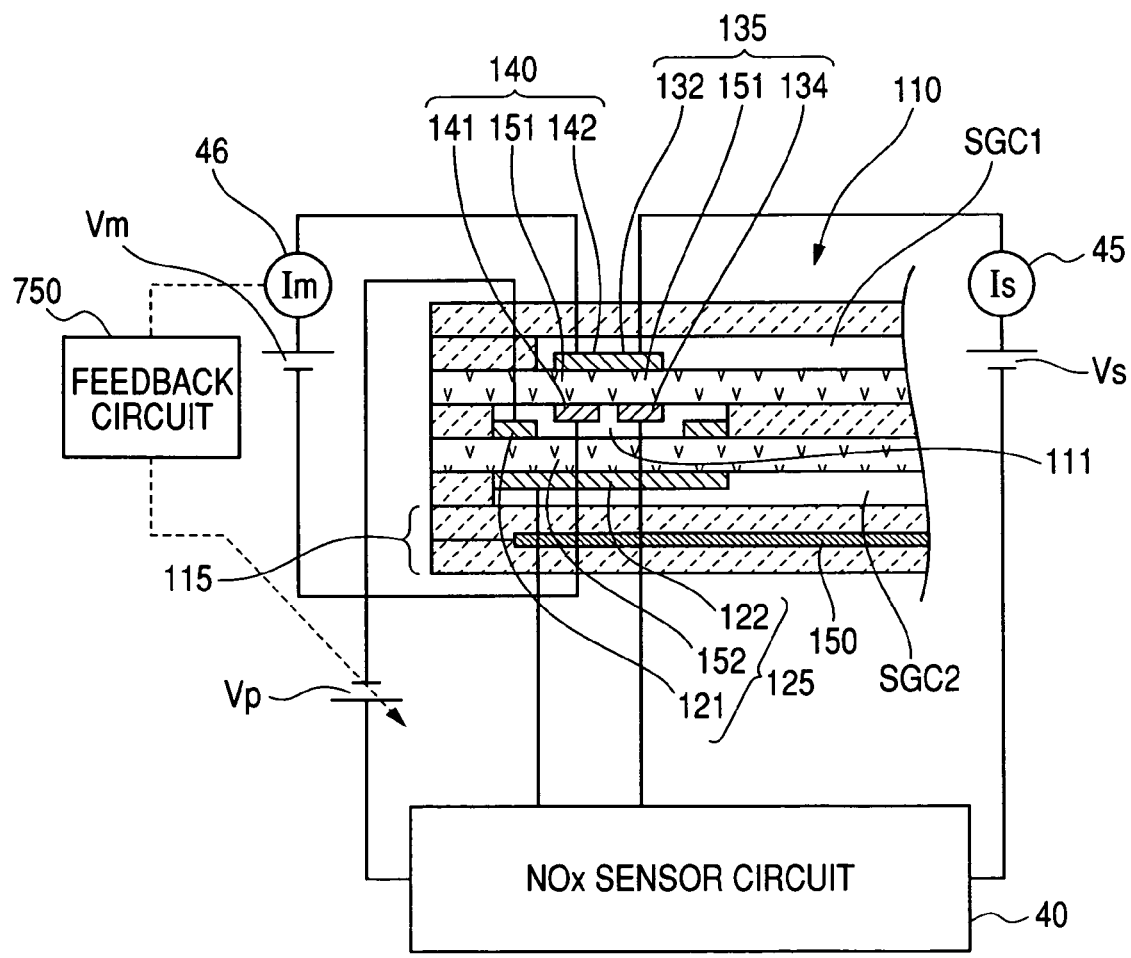
FIG. 16 is a cross sectional view showing the gas sensing element of the first modified form connected to a NOx sensor circuit composed of a sensor circuit, a pump circuit and a monitor circuit.

As shown in FIG. 16, further, the measuring electrode 134 and the reference electrode 132 of the sensor cell 135 are connected via the Is detecting circuit section 45 and the sensor cell power supply VS to the NOx sensor circuit 40.

Furthermore, the measuring electrode 134 and the reference electrode 132 are made of cermet material containing a metallic component having a principal component of Pt and a ceramic component containing a principal component of zirconia. The ceramic component content relative to a total weight of the metallic component and the ceramic component can be determined to lay at a value ranging from, for instance, 10 to 20 wt %.

Further, the measuring electrode 134 includes a Pt—Rh electrode that is active against nitrogen oxides (NOx). The Pt—Rh electrode has an Rh content ranging from, for instance, 10 to 50 wt % relative to a total weight of the metallic component.

Moreover, like the measuring electrode 134 and the reference electrode 132 of the sensor cell 135, the inner pump electrode 121 and the outer pump electrode 122 are made of cermet material containing the metallic component having the principal component of Pt and the ceramic component containing the principal component of zirconia. The ceramic component content relative to a total weight of the metallic component and the ceramic component can be determined to lay at a value ranging from, for instance, 10 to 20 wt %.

Further, the inner pump electrode 121 is made of a Pt—Au electrode that is inactive against nitrogen oxides. The Au content relative to a total weight of the metallic component lies in a value of, for instance, 1 to 10 wt %.

As shown in FIG. 16, the inner monitor electrode 141 and the outer monitor electrode 142 of the oxygen monitor cell 140 is connected to the NOx sensor circuit 40 via the monitor cell power supply Vm and the Im detection circuit section 46.

Like the measuring electrode 134 and the reference electrode 132 of the sensor cell 135, the inner monitor electrode 141 and the outer monitor electrode 142 are made of cermet material containing the metallic component having the principal component of Pt and the ceramic component containing the principal component of zirconia. The ceramic component content relative to a total weight of tee metallic component and the ceramic component can be determined to lay at a value ranging from, for instance, 10 to 20 wt %.

Furthermore, the inner pump electrode 121 is made of a Pt—Au electrode that is inactive against nitrogen oxides. The Au content relative to a total weight of the metallic component lies in a value of, for instance, 1 to 10 wt %.

The oxygen monitor cell 140 includes a feedback circuit 750 that allows an electric current value, measured with the Im detection circuit section 46, to be fed back to the oxygen pump cell 125 such that the oxygen pump cell 125 can be controlled in operation. That is, for instance, a control is executed such that if an electric current value, measured with the Im detection circuit section 46, exceeds a given value, a voltage, applied to the oxygen pump cell 125 from the pump cell power supply Vp, is increased so as to increase a capacity of pumping oxygen delivered from the measuring gas chamber 111 to the second reference gas compartment 102.

Moreover, the measuring electrode 31, the reference electrode 132 (the outer monitor electrode 142), the inner monitor electrode 141, the inner pump electrode 121 and the outer pump electrode 122 are electrically connected to external terminals via electrically conductive lead portions and through-holes (not shown).

As shown in FIGS. 13 and 14, the ceramic heater 115 includes a heater substrate 115a, an insulating layer 115b stacked on the heater substrate 115a and a heating element 150 sandwiched between the heater substrate 115a and the insulating layer 115b.

With the ceramic heater 115, further, the heating element 150, operative to heat when turned on, and a lead portion 153 are formed on a sheet made of alumina by patterning and the insulating layer 115b is placed on the heating element 150. The heating element 150 is made of cermet material composed of ceramic such as, for instance, Pt and alumina or the like.

The ceramic heater 115 serves to allow the heating element 150 to develop a heat when supplied with electric power from the outside for heating the oxygen pump cell 125, the sensor cell 135 and the oxygen monitor cell 140 to active temperatures.

The heating element 150 is supplied with electric power via the lead portion 130 integrally formed on the heating element 150, the through-holes (not shown) and the terminals portions (not shown).

Moreover, the first and second solid electrolyte bodies 151 and 152, the spacers 130, 131 and 132, the insulating layer 115b and the heater substrate 115a can be formed in sheet-like members by a doctor blade method or an extrusion molding method or the like.

Further, the measuring electrode 134, the reference electrode 132, the inner monitor electrode 141, the outer monitor electrode 142, the inner pump electrode 121 and the outer pump electrode 122 can be formed by a screen printing method or the like.

Furthermore, a porous body, forming the diffusion resistance portions 120, can be formed by a screen printing method or the like.

Moreover, the gas sensing element 110 can be formed by stacking ceramic sheets, suitably formed with the various electrodes mentioned above, to form a stack body and firing the stack body in a unitized structure.

Next, an operating principle of the gas sensing element 110 will be described below.

First, measuring gases pass through the diffusion resistance portions 120 under given diffusion resistances to be introduced into the measuring gas chamber 111. The amount of admitted measuring gases is determined in accordance with diffusion resistances of the diffusion resistance portions 120. During a transfer of measuring gases through surface of the inner pump electrode 121 of the oxygen pump cell 125, the oxygen concentration of measuring gases is adjusted with the oxygen pump cell 125.

That is, applying a voltage across the pair of electrodes of the oxygen pump cell 125 to allow the outer pump electrode 122 to act as a positive electrode results in an effect of causing oxygen, contained in measuring gases, to be reduced on the inner pump electrode 121 to form an oxygen ion. The oxygen ion is discharged to the outer pump electrode 122 exposed to the reference gas compartment 102 due to a pumping action. In contrast, if the voltage is applied so as to allow the inner pump electrode 121 to be positive electrode, then, reduction of oxygen occurs on the outer pump electrode 122 to form oxygen ions, which are discharged to the inner pump electrode 121 exposed to the measuring gas chamber 111 due to a pumping action. That is, the oxygen pump cell 125 is structured such that with a voltage applied to the pair of electrodes, the oxygen pump cell 125 allows oxygen to flow into or flow out from the measuring gas chamber 111 for adjusting an oxygen concentration in the measuring gas chamber 111.

Particularly, during the flow of measuring gases through the diffusion resistance portions 120, it is likely that measuring gases tend to be easily brought into contact with the inner pump electrode 121, resulting in a consequence of easily adjusting the oxygen concentration.

Subsequently, measuring gases passing across the inner pump electrode 121 reach the measuring electrode 134 of the sensor cell 135 and the inner monitor electrode 141 of the oxygen monitor cell 140.

With a given voltage (of, for instance, 0.40V) being applied across the pair of electrodes of the oxygen monitor cell 140 such that the outer monitor electrode 142, exposed to the first reference gas compartment RGC1, becomes a positive electrode, reduction of oxygen in measuring gases occurs on the inner monitor electrode 141 exposed to the first reference gas compartment RGC1. This results in the formation of oxygen ions, which are discharged to the inner monitor electrode 141 exposed to the measuring gas chamber 111 due to a pumping action for thereby causing an oxygen ion current to flow.

Here, since the inner monitor electrode 141 is comprised of the cermet electrode made of Pt—Au alloy that is inactive in decomposing nitrogen oxides, the oxygen ion current, flowing through the oxygen monitor cell 140, depends on the amount of oxygen contained in measuring gases and does not depend on the amount of nitrogen oxides. This allows a value of the electric current, flowing through the oxygen monitor cell 140, to be detected, thereby enabling the detection of the oxygen concentration in the measuring gas chamber 111.

Further, the gas sensing element 110 of the present embodiment is structured such that the oxygen pump cell 125 can be controlled via the feedback circuit 750 in accordance with a detected value of the electric current flowing through the oxygen monitor cell 140 to allow the measuring gas chamber 111 to have the oxygen concentration laying at a given fixed value. That is, controlling a voltage applied to the oxygen pump cell 130 in response to an output signal from the oxygen monitor cell 140 so as to allow the oxygen monitor cell 140 to provide an electric current value laying at a desired fixed value (of, for instance, 0.2 μm) results in a capability of controlling the oxygen concentration of the measuring gas chamber 111 at a fixed value.

Furthermore, a given voltage (of, for instance, 0.40V) is applied to the sensor cell 135 such that the reference electrode 132, exposed to the first reference gas compartment RGC1, becomes a positive electrode. As set forth above, since the measuring electrode 134 is comprised of the cermet electrode made of Pt—Rh alloy that is active in decomposing nitrogen oxides, reductions of oxygen and nitrogen oxides, contained in measuring gases prevailing in the measuring gas chamber 111, occur on the measuring electrode 134 to form oxygen ions. The oxygen ions are discharged to the reference electrode 132 exposed to the first reference gas compartment RGC1 due to a pumping action for thereby causing an oxygen ion current to flow across the measuring electrode 134 and the reference electrode 132. This electric current represents an electric current derived from concentrations of NOx and oxygen contained in measuring gases.

Meanwhile, as mentioned above, the electric current flowing through the oxygen monitor cell 140 represents an electric current depending on the oxygen concentration in the measuring gas chamber 111. Thus, it becomes possible to detect a NOx concentration based on a difference between a value of electric current flowing through the sensor cell 135 and a value of electric current flowing through the oxygen monitor cell 140.

The gas sensing element 110 operates in a manner as described below.

The diffusion resistance portions 120 are formed on the first solid electrolyte body 151 so as to extend from the measuring gas chamber 111 in a direction perpendicular to the stack direction Z between the first and second solid electrolyte bodies 151 and 152. This allows a distance S between the external end wall 120*a* of the diffusion resistance portion 120, i.e., an inlet port of measuring gases, and the measuring electrode 134 to be shortened, enabling an increase in response of the gas sensing element 110.

With the gas sensing element 110 of the present embodiment, the diffusion resistance portions 120 are formed on the first solid electrolyte body 151 in areas extending along the widthwise direction X perpendicular to the longitudinal direction Y of the gas sensing element 110. This easily results in an effect of deceasing the distance S between the external end wall 120*a* of each diffusion resistance portion 120, i.e., the inlet port of measuring gases, and the measuring electrode 134. Thus, the gas sensing element 110 can have further increased response.

Moreover, the measuring electrode 134 is formed on the first solid electrolyte body 151 in an area inward of the external end wall 211 of the inner pump electrode 121. This allows the oxygen pump cell 125 to adjust the oxygen concentration in measuring gases before measuring gases reach the measuring electrode 134. Therefore, the gas sensing element 110 can have increased measuring precision.

With the gas sensing element 110 of the present embodiment, especially, the measuring electrode 134 is formed on the first solid electrolyte body 151 in an area inward of an inner end wall 212 of the inner pump electrode 121. This allows the oxygen concentration to be adequately adjusted with the oxygen pump cell 125 and, subsequently, measuring gases with the oxygen concentration being adjusted can be supplied to the measuring electrode 134. Thus, the gas sensing element 110 can have increased precision in measuring a specified gas concentration.

Further, the diffusion resistance portions 12 and the inner pump electrodes 121 are disposed adjacent to each other in the stack direction. Therefore, measuring gases can be adequately held in contact with the inner pump electrodes 121 during a phase in which measuring gases pass across the diffusion resistance portions 120 to be admitted to the measuring gas chamber 111. During such a phase, therefore, the oxygen pump cell 125 can adequately pump oxygen, thereby enabling the oxygen concentration in measuring gases to be adequately adjusted.

Furthermore, with the gas sensing element 110 provided with the oxygen monitor cell 140, the oxygen concentration in the measuring gas chamber 111 can be accurately grasped to obtain a measured result. Permitting the measured result to be used in a feedback control for controlling the oxygen pump cell 125 while causing the measured result to be used in correcting the measured value of the sensor cell 135, enabling an increase in measuring precision. In addition, the inner monitor electrode 141 is placed in an area inward of the external end wall 211 of the inner pump electrode 121. This enables the oxygen monitor cell 120 to accurately measure the oxygen concentration of measuring gases whose oxygen concentration is adjusted with the oxygen pump cell 125.

In particular, if an attempt is made to decrease the distance S between the external end wall 120*a* of the diffusion resistance portion 120 and the measuring electrode 134 to obtain improved response, then, there is a risk of a difficulty occurring in adequately ensuring oxygen pumping capability. Therefore, providing the oxygen monitor cell 140 results in capabilities of minimizing the fluctuation in oxygen concentration in the measuring gas chamber 111 and correcting the measured value. Thus, it becomes possible to secure precision of detecting a specified gas concentration (NOx concentration).

With the gas sensing element 110 of the present embodiment, moreover, the inner monitor electrode 141 is disposed in an area inward of the inner end wall 212 of the inner pump electrode 121. This enables measuring gases, whose oxygen concentration is adequately adjusted with the oxygen pump cell 125, to be supplied to the inner monitor electrode 141, thereby enabling an increase in precision of measuring the oxygen concentration.

Further, the gas sensing element 110 of the present embodiment is structured such that a voltage applied to the oxygen pump cell 125 is controlled in response to a detection signal on the oxygen concentration in the oxygen monitor cell 140. This allows the oxygen concentration to be sustained at a fixed value in the measuring gas chamber 111. Especially, if an attempt is made to decrease the distance S between the external end wall 120*a* of the diffusion resistance portion 120 and the measuring electrode 134 to obtain improved response, then, the inner pump electrode 121 tends to have a decreased width W, causing a risk of a difficulty in adequately ensuring oxygen pumping capability. Therefore, permitting the oxygen monitor cell 140 to monitor the oxygen concentration in the measuring gas chamber 111 while causing a resulting detection signal to be supplied to the oxygen pump cell 125 in a feedback loop, enabling the oxygen concentration to be easily adjusted.

Furthermore, the oxygen monitor cell 140 is structured such that when a given voltage is applied across the inner monitor electrode 141 and the outer monitor electrode 142, an electric current is caused to flow depending on the oxygen concentration in measuring gases. Further, another arrangement is made such that a specified gas concentration (NOx concentration) is detected depending on a difference between an electric current flowing through the sensor cell 135 and an electric current flowing through the oxygen monitor cell 140. This enables the measures value on the specified gas concentration (NOx concentration) in the sensor cell 135 to be corrected, making it possible to obtain an accurate measuring value.

Further, since the dispersion resistance portions 12 are made of the porous body, diffusion resistance can be easily adjusted.

Furthermore, the shortest distance S between the external end wall 120*a* of the diffusion resistance portion 120 and the measuring electrode 134 is set to a value ranging from 1 to 3 mm. This results in a capability of obtaining the gas sensing element 110 with adequately improved response while ensuring adequately improved measuring precision.

With the present embodiment, as set forth above, it becomes possible to provide a gas sensing element with excellent response and increased measuring precision.

[Gas Sensing Element of Second Modified Form]

Figure 17:
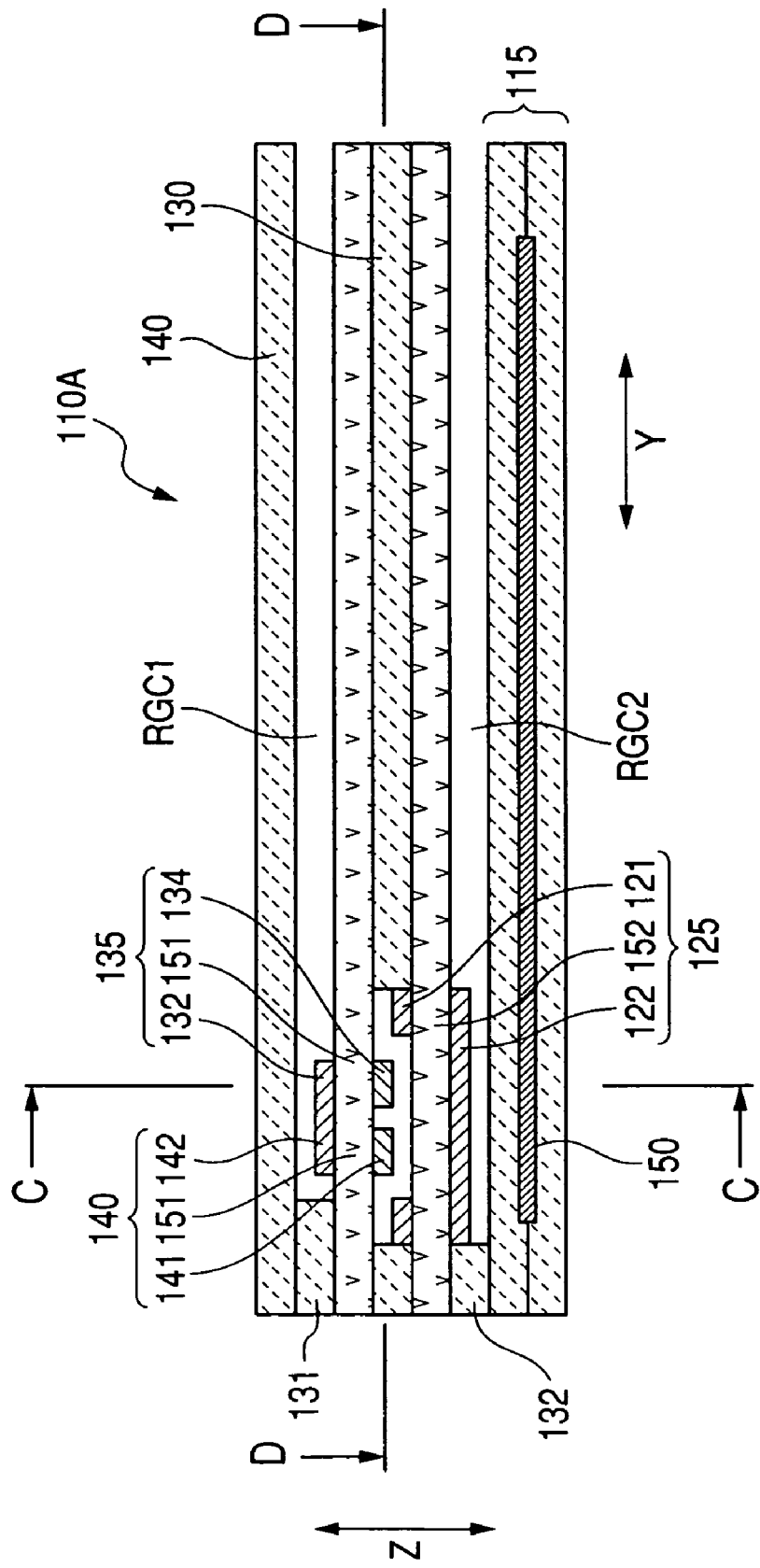
FIG. 17 is a cross sectional view showing a gas sensing element of a second modified form of the gas sensing element shown in FIG. 1.
Figure 18:
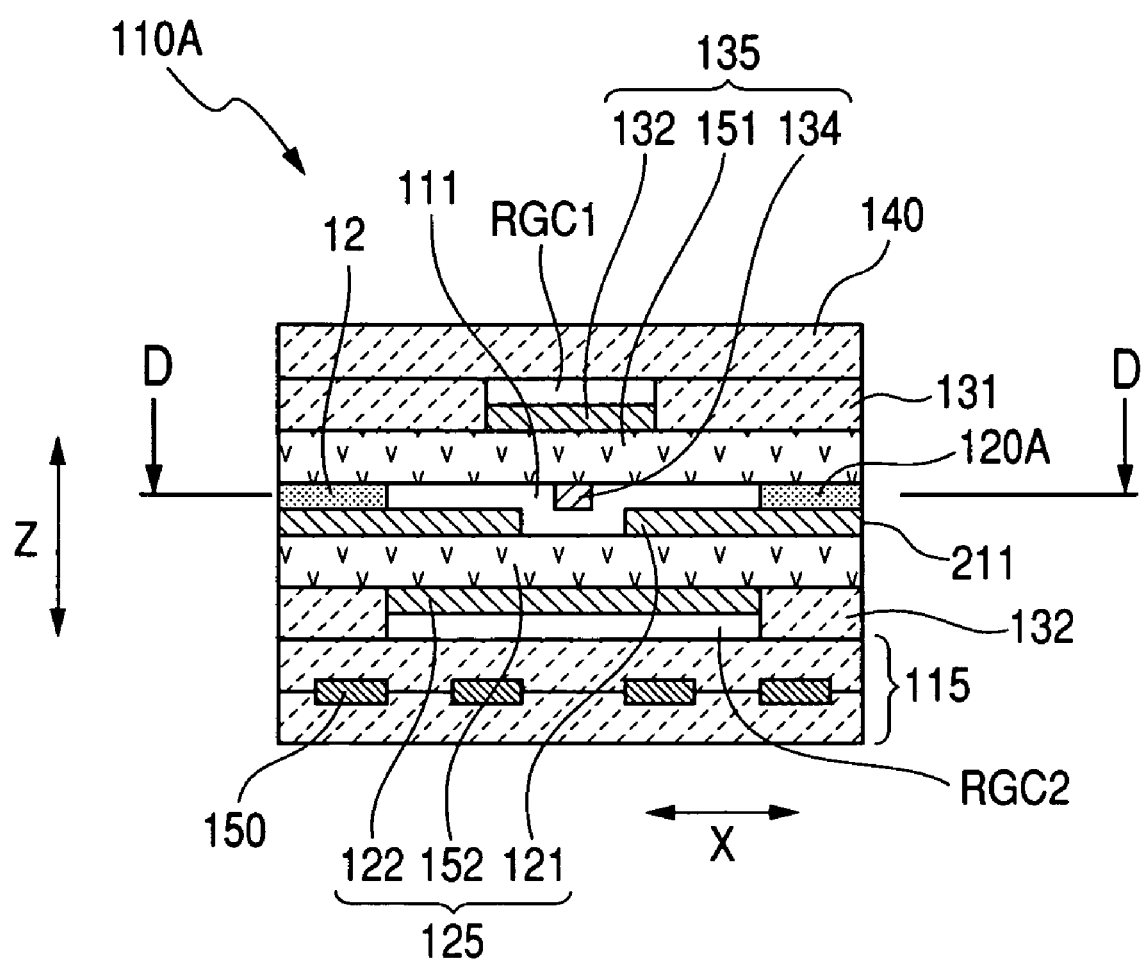
FIG. 18 is a cross sectional view of the gas sensing element taken on line C-C of FIG. 17.
Figure 19:
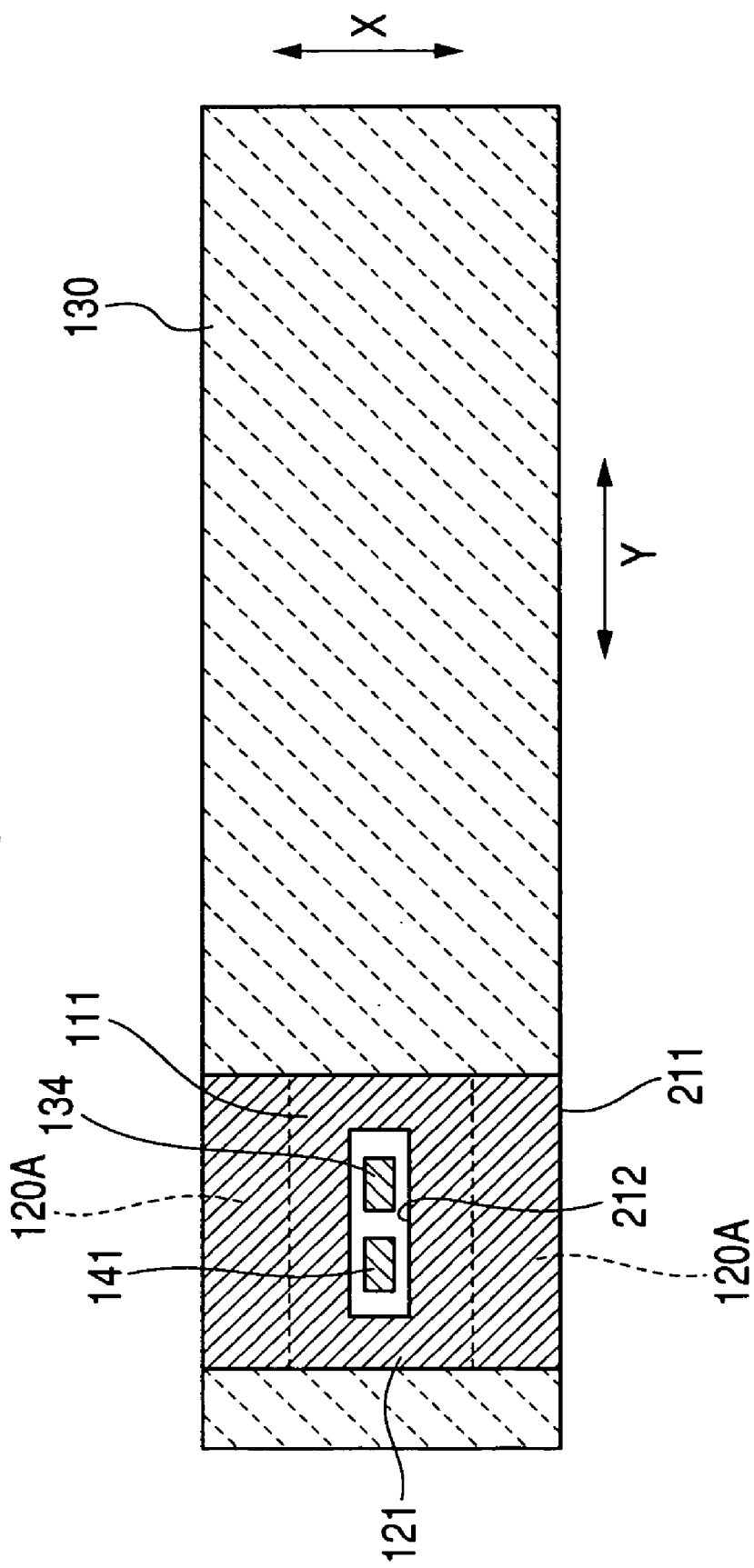
FIG. 19 is a cross sectional view of the gas sensing element taken on line D-D of FIGS. 17 and 18.

A gas sensing element 110A of a second modified form will be described below in detail with reference to FIGS. 17 to 19 with like component parts bearing the same reference numerals as those of the gas sensing element of the first modified form shown in FIGS. 13 to 16.

The gas sensing element 110A of the second modified form differs from the gas sensing element 110 of the first modified form in respect of structures of gas diffusion resistance portions 120A. That is, with the gas sensing element 110A of the second modified form, the gas diffusion resistance portions 120A are not made of porous bodies, used for the gas diffusion resistance portions 120 of the gas sensing element 110 of the first modified form, but are formed of slits with minimized clearances. The slits are formed in structure by suitably adjusting a thickness in the stack direction Z so as to obtain desired diffusion resistances. This thickness can be set to a value of, for instance, 5 to 50 μm.

The gas sensing element 110A of the second modified form has the same other structure as that of the gas sensing element 110 of the first modified form.

With the gas sensing element 110A of the present modification, there is no need arising for performing step of forming a porous body, thereby achieving a reduction in production cost.

In addition, the gas sensing element 110A of the present modification performs the same operation as that of the gas sensing element 110 of the first modified form and, hence, detailed description of the same is herein omitted.

[Gas Sensing Element of Third Modified Form]

Figure 20:
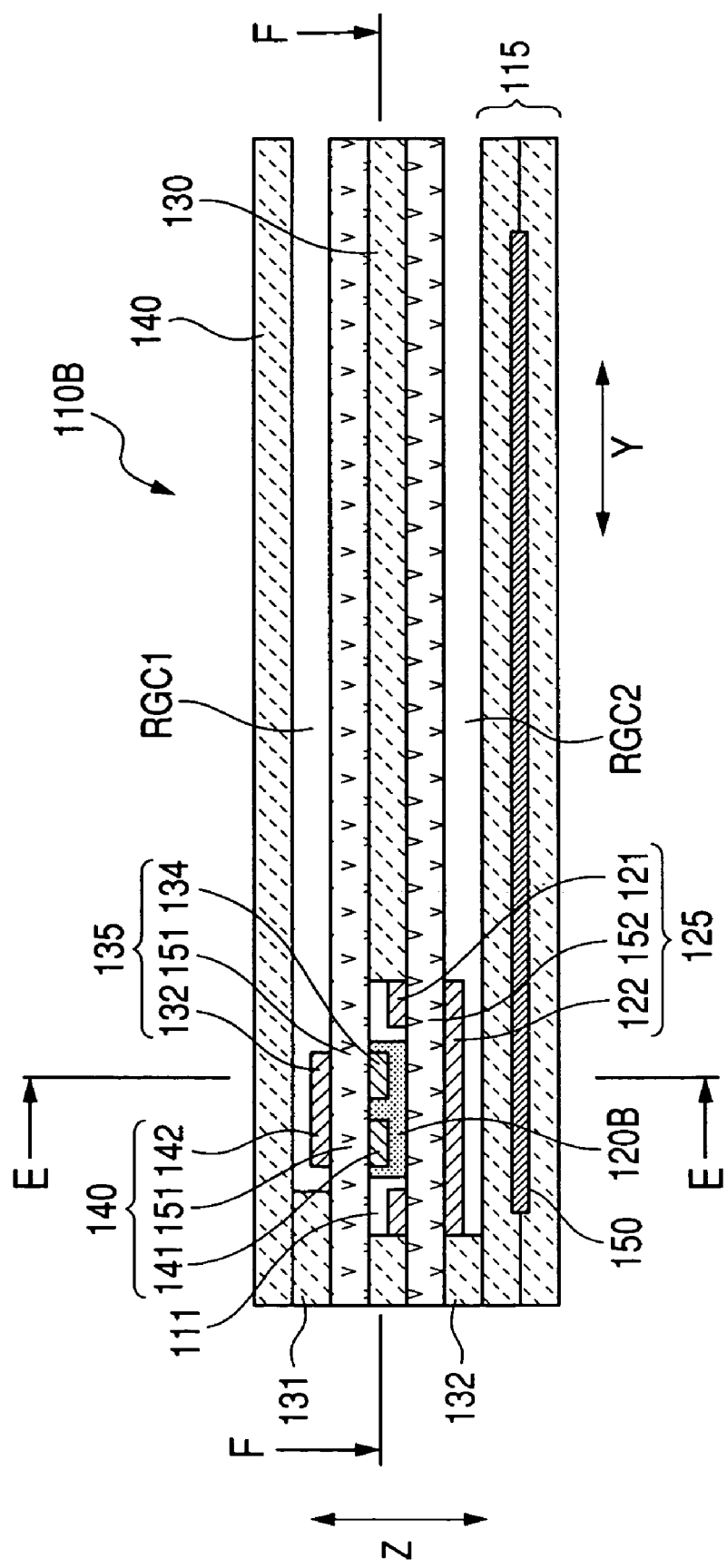
FIG. 20 is a cross sectional view showing a gas sensing element of a third modified form of the gas sensing element shown in FIG. 1.
Figure 21:
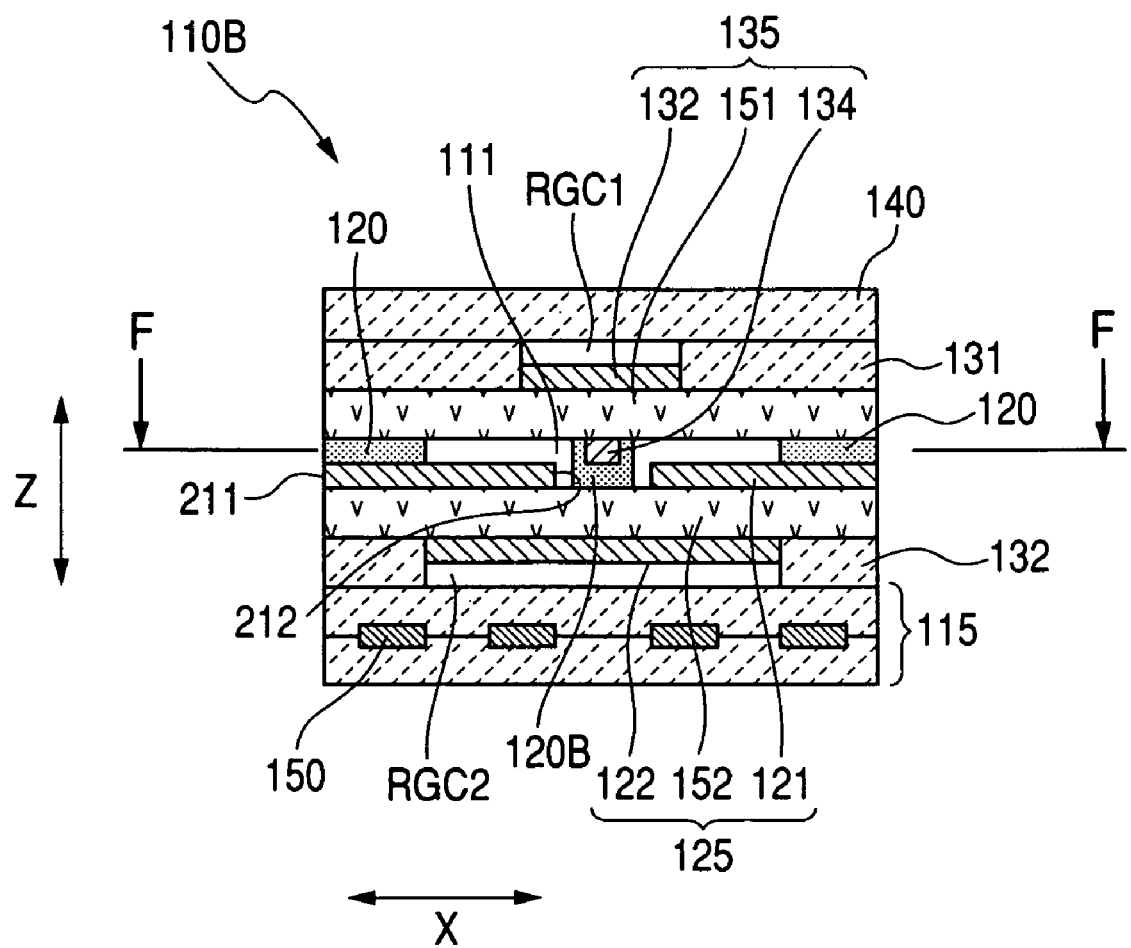
FIG. 21 is a cross sectional view of the gas sensing element taken on line E-E of FIG. 20.
Figure 22:
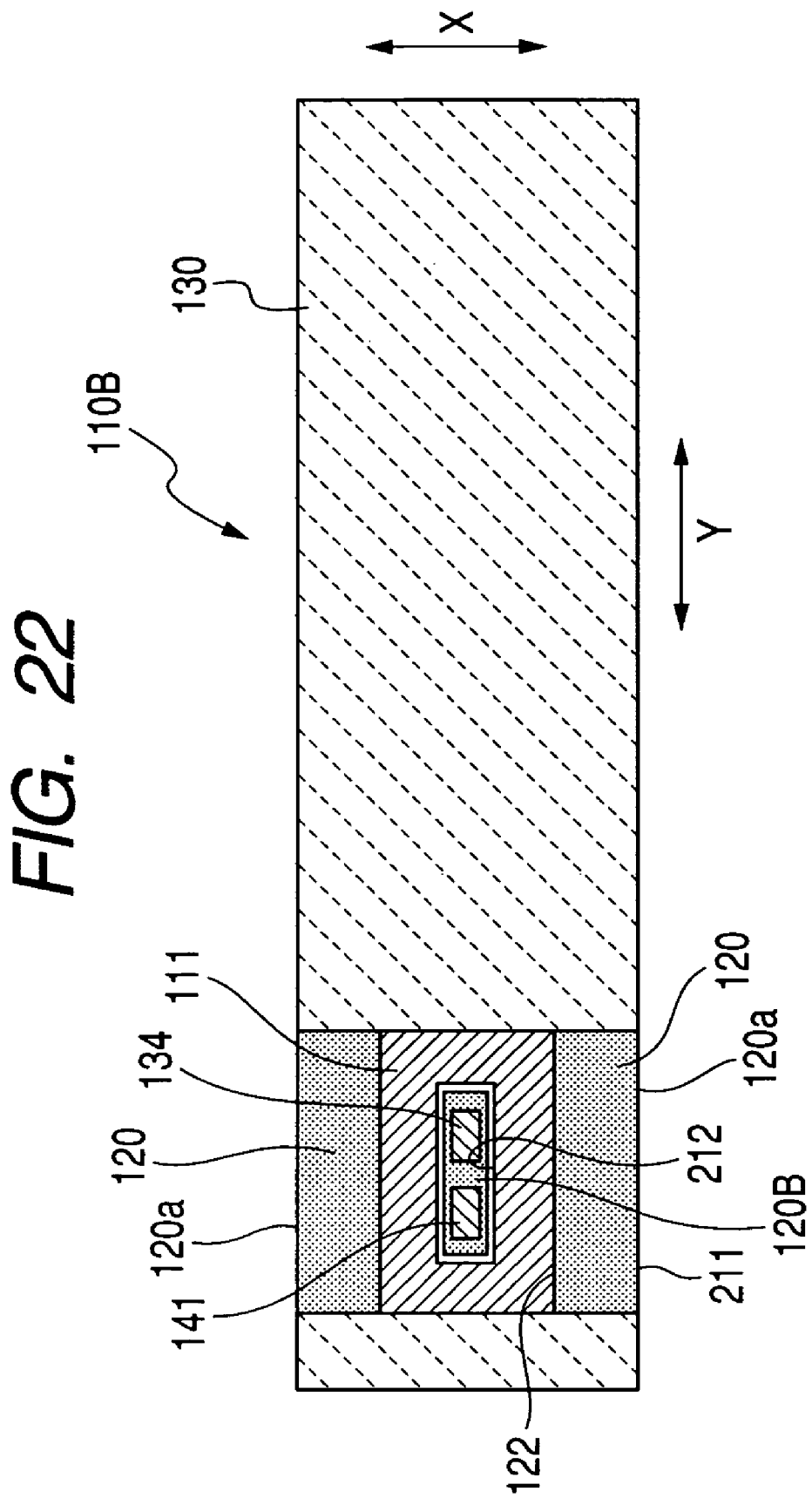
FIG. 22 is a cross sectional view of the gas sensing element taken on line F-F of FIGS. 20 and 21.

A gas sensing element 110B of a third modified form will be described below in detail with reference to FIGS. 20 to 22 with like component parts bearing the same reference numerals as those of the gas sensing element of the first modified form shown in FIGS. 13 to 16.

The gas sensing element 110B of the third modified form differs from the gas sensing element 110 of the first modified form in that a gas diffusion resistance portion 120B is provided between the measuring electrode 134 and the inner pump electrode 121 for providing diffusion resistance for measuring gases.

The gas diffusion resistance portion 120B is comprised of a porous body, made of ceramic such as alumina or the like, which is formed on the first solid electrolyte body 151 so as to cover both the measuring electrode 134 and the oxygen monitor electrode. In addition, the gas diffusion resistance portion 120B is located in an area inward of the inner end wall 212 of the inner pump electrode 121.

The gas sensing element 110B of the third modified form has the same other structure as that of the gas sensing element 110 of the first modified form.

With the gas sensing element 110B of the present modification, measuring gases, first adjusted with the oxygen pump cell 125 in adequate oxygen concentration, can be supplied to the measuring electrode 134, enabling a specified gas concentration to be detected with improved precision.

The gas sensing element 110B of the present modification performs the same operation as that of the gas sensing element 110 of the first modified form and, hence, detailed description of the same is herein omitted.

[Gas Sensing Element of Fourth Modified Form]

Figure 23:
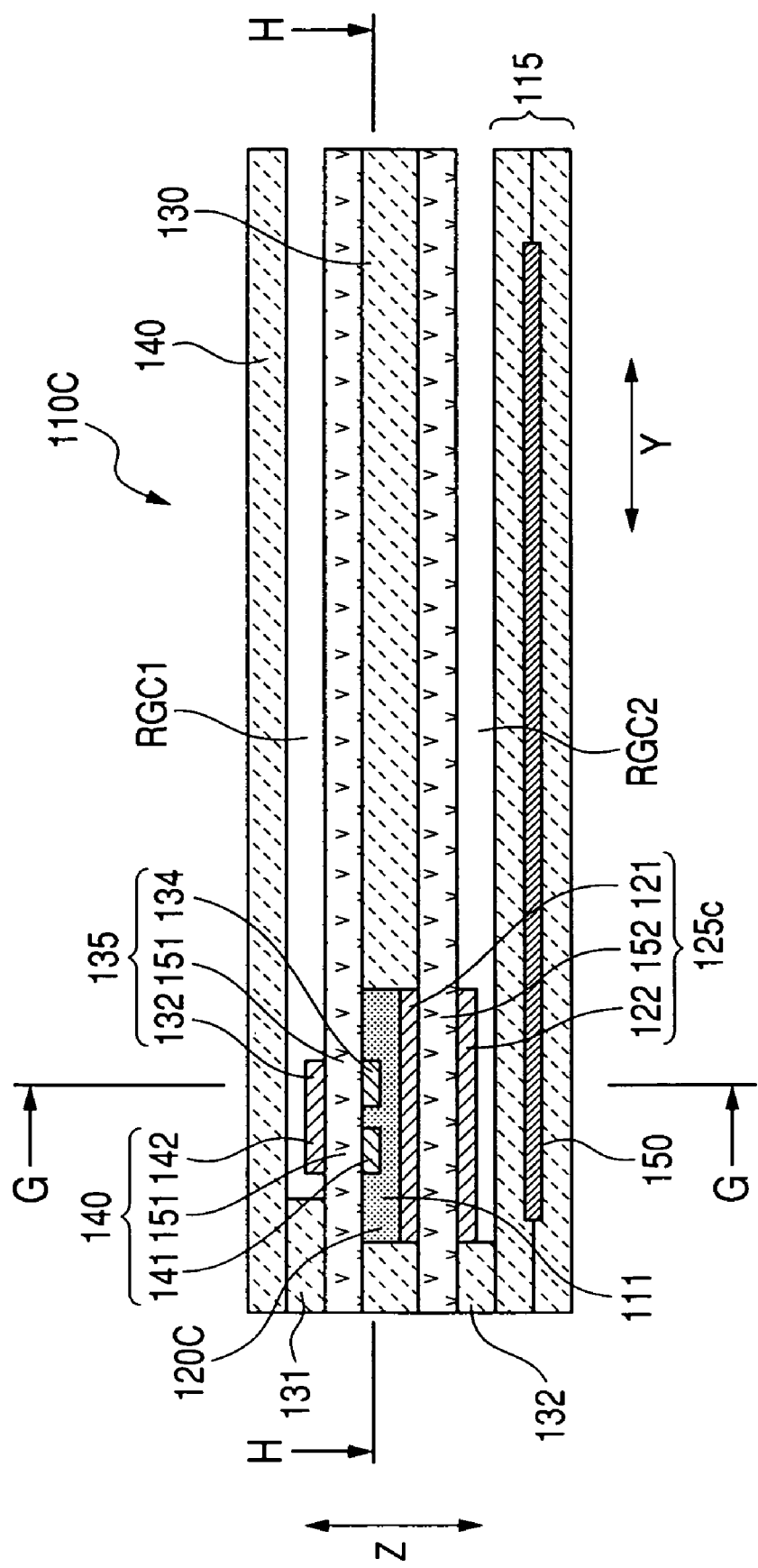
FIG. 23 is a cross sectional view showing a gas sensing element of a fourth modified form of the gas sensing element shown in FIG. 1.
Figure 24:
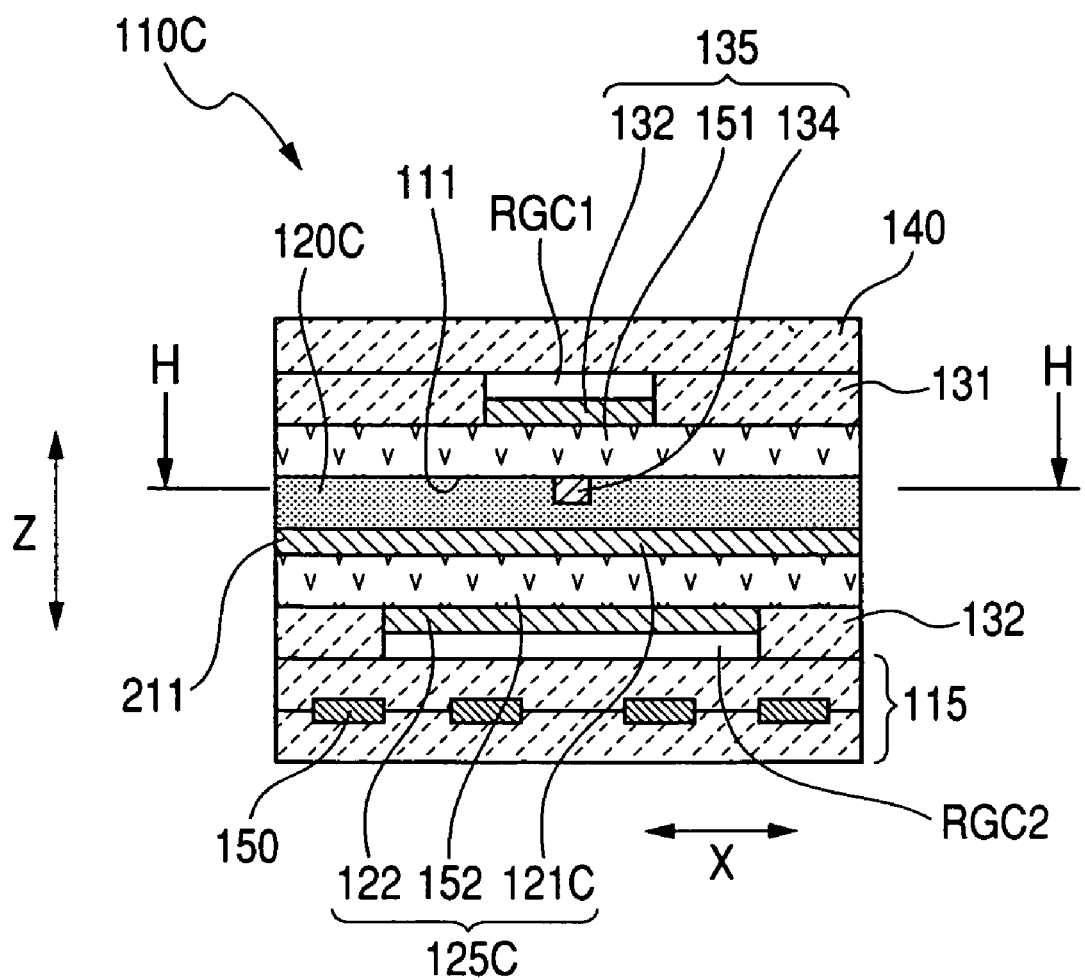
FIG. 24 is a cross sectional view of the gas sensing element taken on line G-G of FIG. 23.
Figure 25:
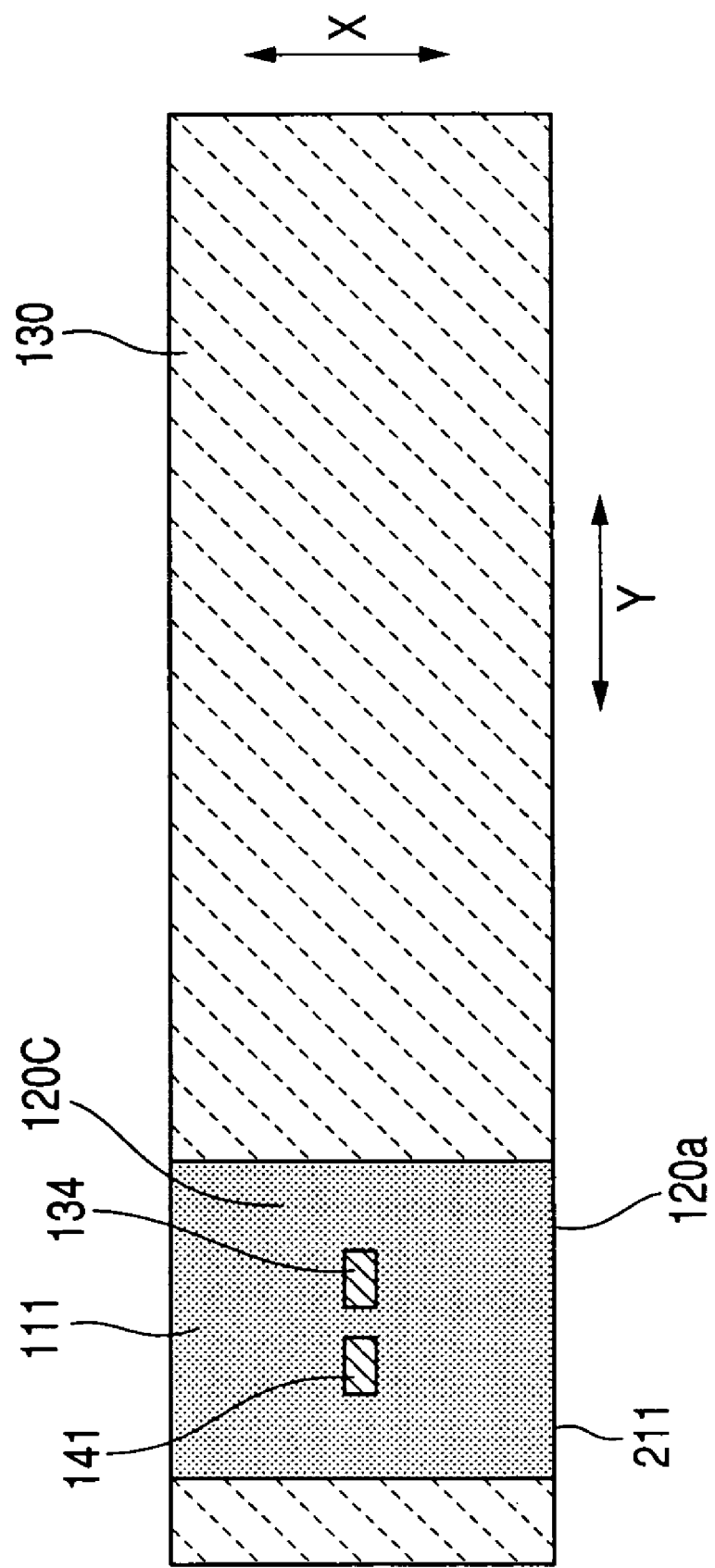
FIG. 25 is a cross sectional view of the gas sensing element taken on line H-H of FIGS. 23 and 24.

A gas sensing element 110C of a fourth modified form will be described below in detail with reference to FIGS. 23 to 25 with like component parts bearing the same reference numerals as those of the gas sensing element of the first modified form shown in FIGS. 13 to 16.

The gas sensing element 110C of the fourth modified form differs from the gas sensing element 110 of the first modified form in that an oxygen pump cell 125C has an inner pump electrode 121C formed on the second solid electrolyte body 152 in a whole surface area facing the measuring gas chamber 111 and a gas diffusion resistance portion 120C is formed in a whole of the measuring gas chamber 111 so as to cover the measuring electrode 134 and the inner monitor electrode 141 for providing diffusion resistance for measuring gases.

The gas sensing element 110C of the present modified form has the same other structure as that of the gas sensing element 110 of the first modified form.

With the gas sensing element 110C of the present modification, the oxygen pump cell 125C can easily adjust the oxygen concentration in the measuring gas chamber 111.

The gas sensing element 110C of the present modification performs the same operation as that of the gas sensing element 110 of the first modified form and, hence, detailed description of the same is herein omitted.

[Gas Sensing Element of Fifth Modified Form]

Figure 26:
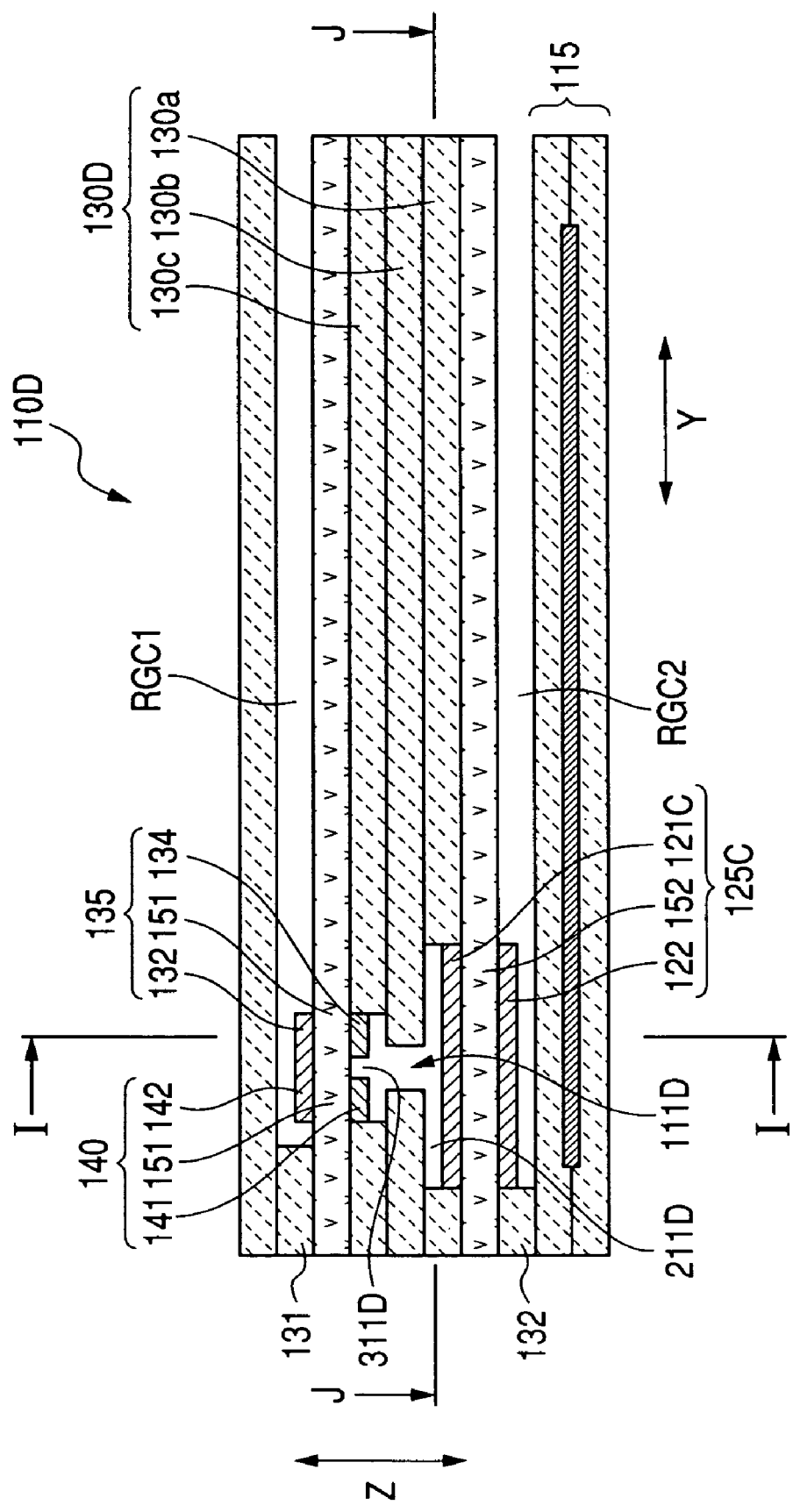
FIG. 26 is a cross sectional view showing a gas sensing element of a fifth modified form of the gas sensing element shown in FIG. 1.
Figure 27:
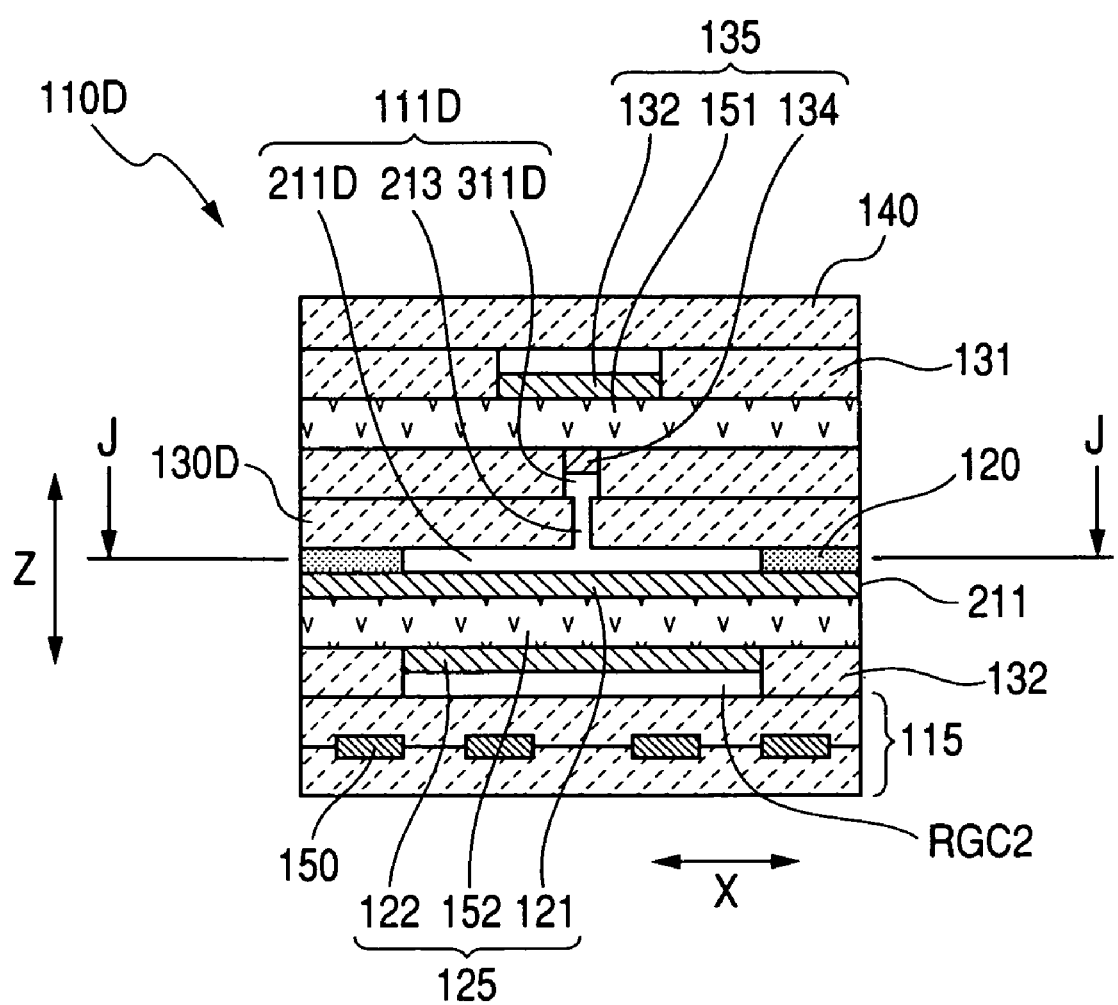
FIG. 27 is a cross sectional view of the gas sensing element taken on line I-I of FIG. 26.
Figure 28:
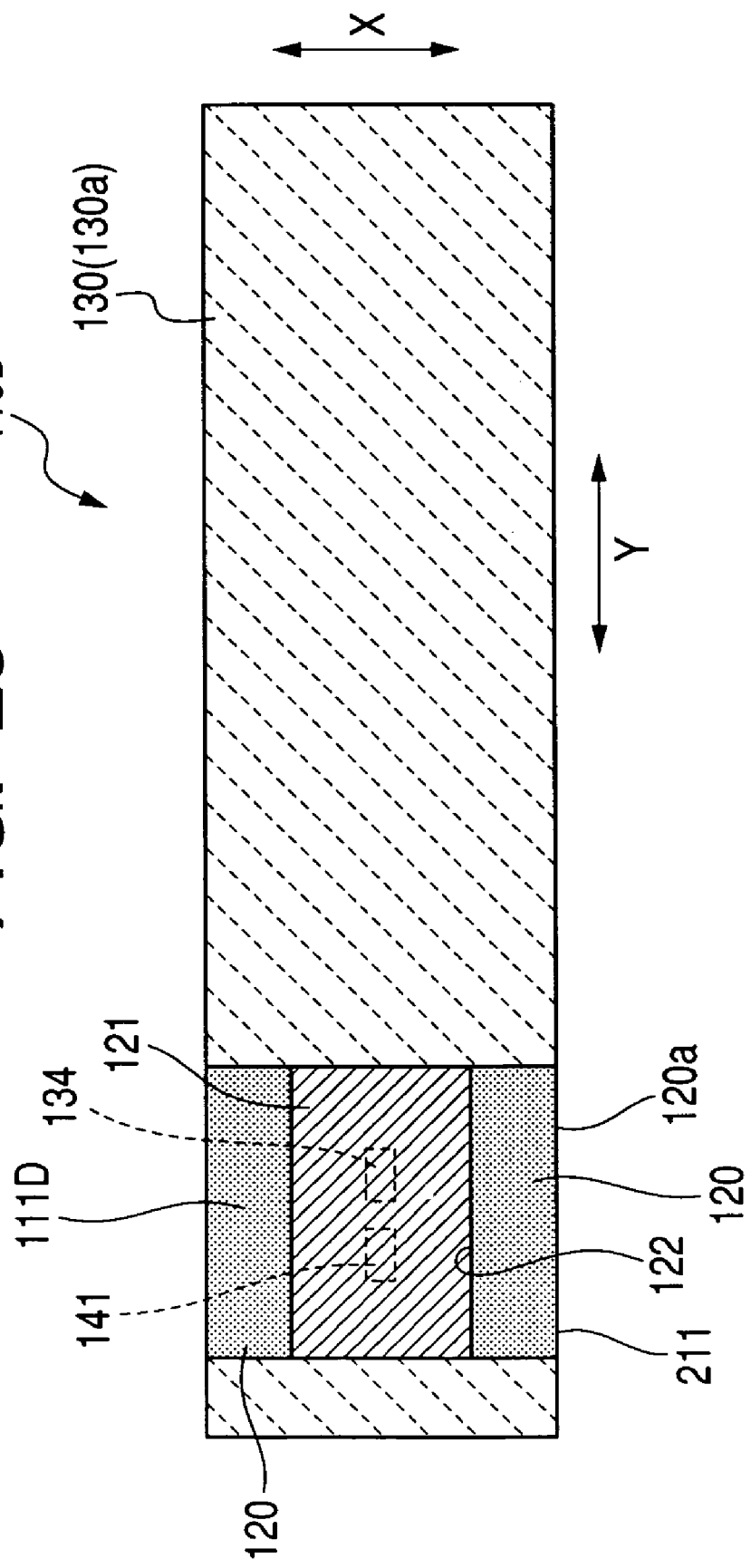
FIG. 28 is a cross sectional view of the gas sensing element taken on line J-J of FIGS. 26 and 27.

A gas sensing element 110D of a fifth modified form will be described below in detail with reference to FIGS. 26 to 28 with like component parts bearing the same reference numerals as those of the gas sensing element 110C of the fourth modified form mentioned above.

The gas sensing element 110D of the fifth modified form differs from the gas sensing element 110C of the fourth modified form in that a measuring gas chamber 111D includes a first measuring gas chamber 211D and a second measuring gas chamber 311D which communicate each other via a restricted portion 213 and the inner pump electrode 121C faces the first measuring gas chamber 211D while the measuring electrode 134 and the inner monitor electrode 141 face the second measuring gas chamber 311D In addition, the inner pump electrode 121 C is formed on the second solid electrolyte body 152 in a whole surface area thereof at a position placed in face-to-face relation to the first measuring gas chamber 211D.

A space 130 is provided between the first and second solid electrolyte bodies 151 and 152 and includes ceramic layers 130a, 130b and 130c in three layers having cutout portions formed at different positions. The ceramic layer 130a has a first cutout portion by which the restricted portion 213 is defined and the ceramic layer 130c has a third cutout portion by which the second measuring gas chamber 311D is defined The gas sensing element 110C of the present modified form has the same other structure as that of the gas sensing element 110 of the first modified form.

With the gas sensing element 110D of the present modification, measuring gases are admitted tough the diffusion resistance portions 120 to the first measuring gas chamber 211D in which the oxygen pump cell 125C adjusts the oxygen concentration. Thereafter, measuring gases pass across the restricted portion 213 to flow into the second measuring gas chamber 311D, in which the sensor cell 135 detects a specified gas concentration and the oxygen monitor cell 140 detects an oxygen concentration.

Therefore, it becomes possible to obtain the gas sensing element 110D with further excellent measuring precision.

The gas sensing element 110D of the present modification performs the same operation as that of the gas sensing element 110C of the fourth modified form and, hence, detailed description of the same is herein omitted.

[Gas Sensing Element of Sixth Modified Form]

Figure 29:
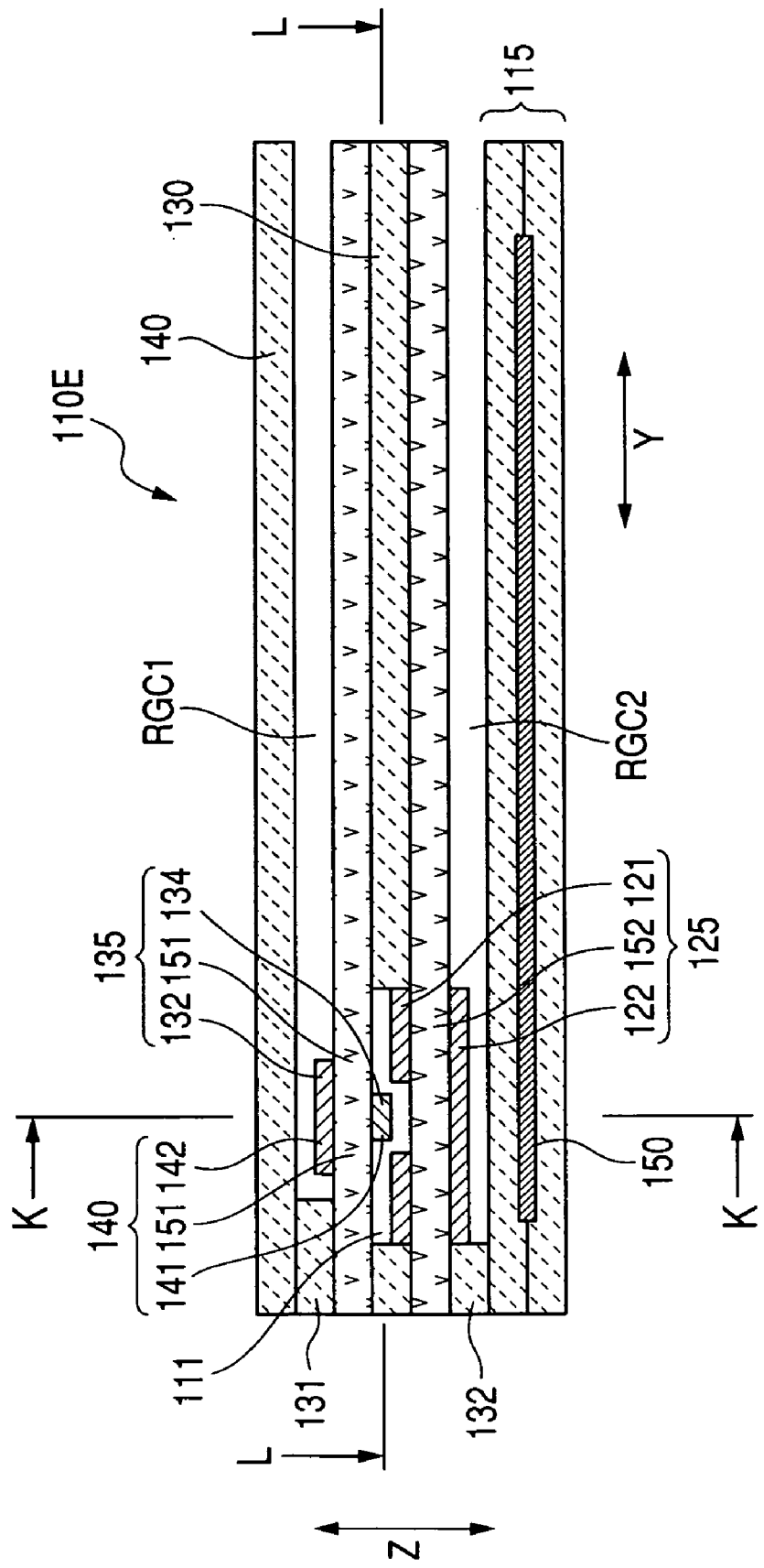
FIG. 29 is a cross sectional view showing a gas sensing element of a sixth modified form of the gas sensing element shown in FIG. 1.
Figure 30:
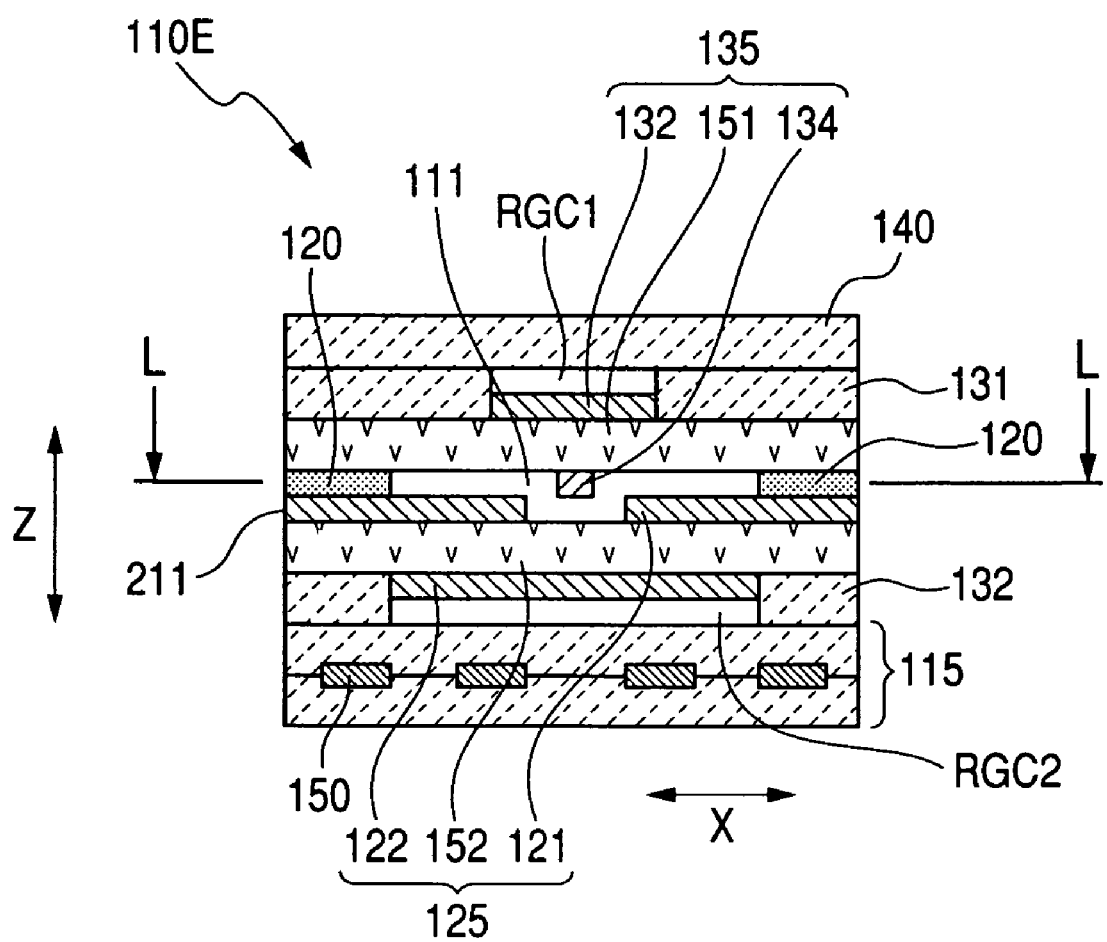
FIG. 30 is a cross sectional view of the gas sensing element taken on line K-K of FIG. 29.
Figure 31:
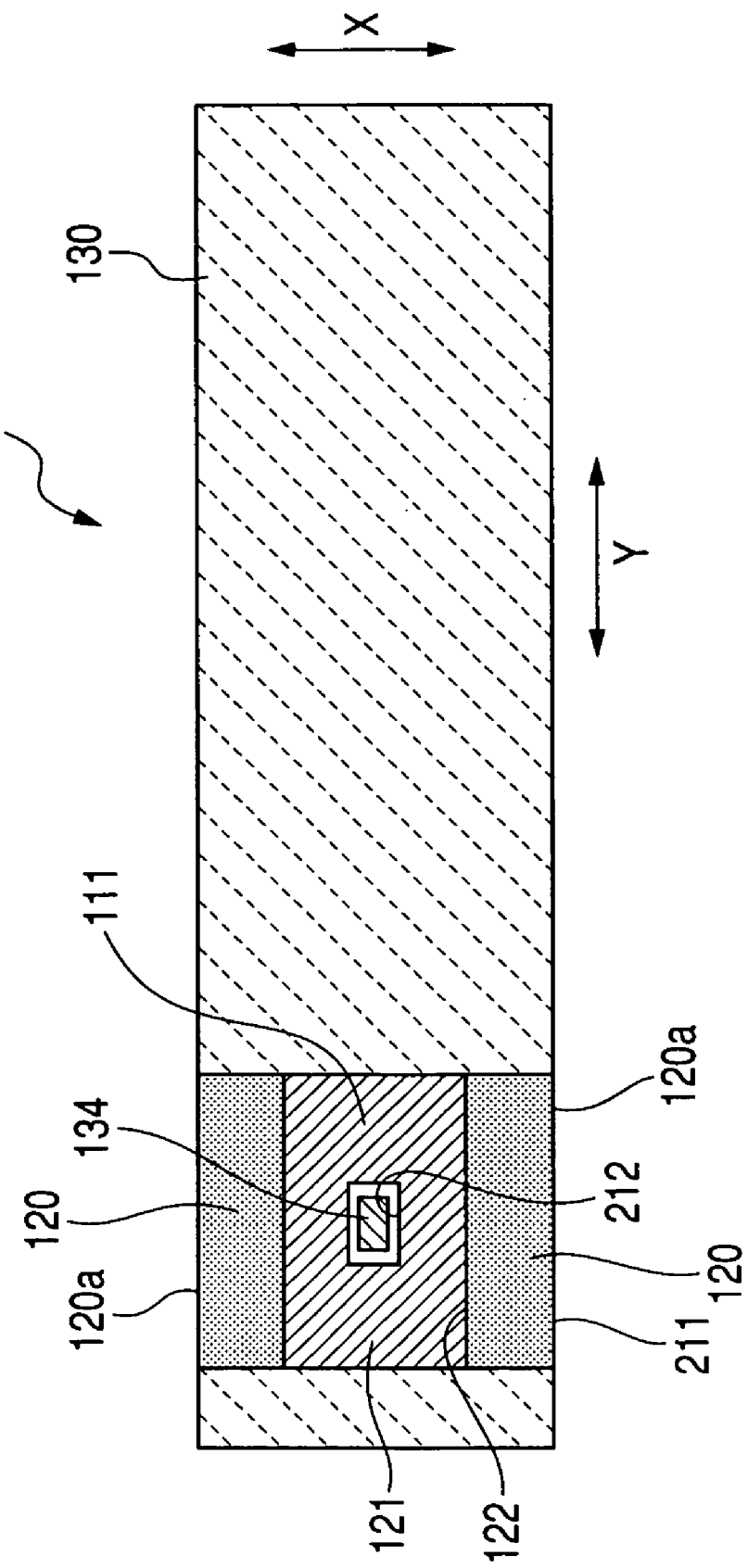
FIG. 31 is a cross sectional view of the gas sensing element taken on line L-L of FIGS. 29 and 30.

A gas sensing element 110D of a sixth modified form will be described below in detail with reference to FIGS. 29 to 31 with like component parts bearing the same reference numerals as those of the gas sensing elements 110 to 110D of the first to fifth modified forms mentioned above.

The gas sensing element 110E of the sixth modified form differs from the gas sensing elements 110 to 110D of the first to fifth modified forms in the absence of the monitor cell 140.

With such a structure, the oxygen pump cell 125 serves to adequately discharge oxygen from the measuring gas chamber 111 for decreasing the oxygen concentration to the extent in that the sensor cell 135 has no adverse affect in detecting the specified gas concentration (NOx concentration).

The gas sensing element 110E of the present modified form has the same other structure as that of the gas sensing element 110 of the first modified form.

With the present modified form, the gas sensing element 110E can be easily manufactured in a simplified structure at low cost.

The gas sensing element 110E of the present modification performs the same operation as that of the gas sensing element 110 of the first modified form and, hence, detailed description of the same is herein omitted.

[Gas Sensing Element of Seventh Modified Form]

Figure 32:
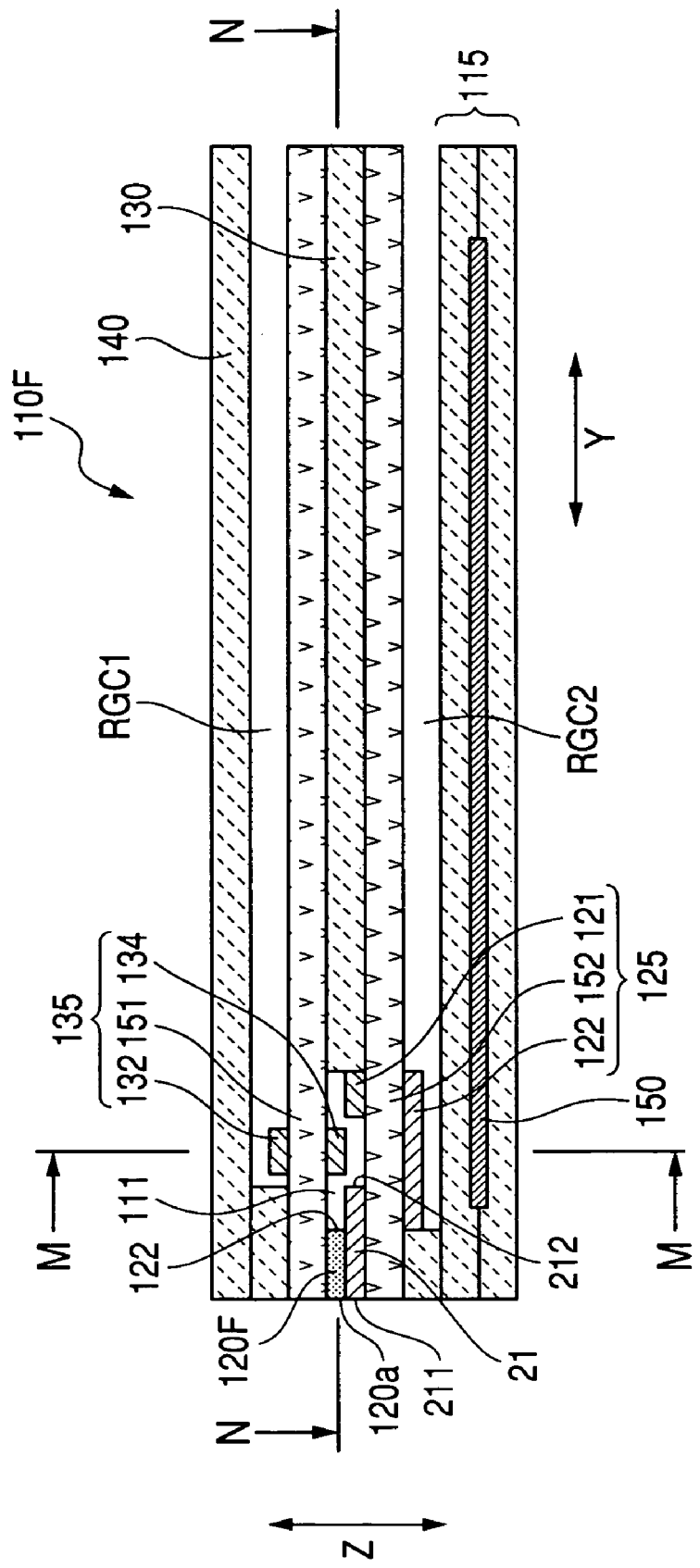
FIG. 32 is a cross sectional view showing a gas sensing element of a seventh modified form of the gas sensing element shown in FIG. 1.

A gas sensing element 110F of a seventh modified form will be described below in detail with reference to FIGS. 32 to 34 with like component parts bearing the same reference numerals as those of the gas sensing element 110 of the first modified form mentioned above.

The gas sensing element 110F of the seventh modified form differs from the gas sensing elements 110 of the first modified form in that the gas sensing element 110F has a distal end formed with a diffusion resistance portion 120F.

Figure 33:
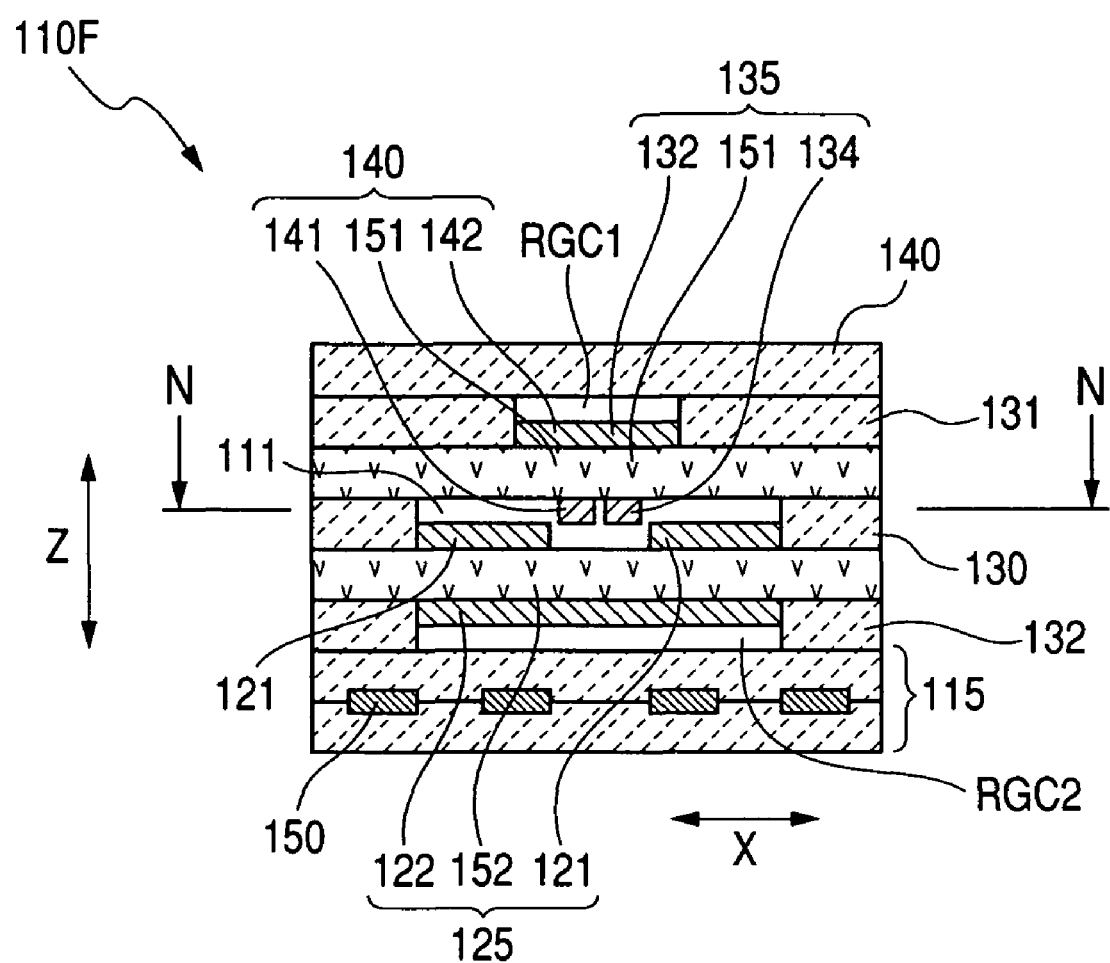
FIG. 33 is a cross sectional view of the gas sensing element taken on line M-M of FIG. 32.
Figure 34:
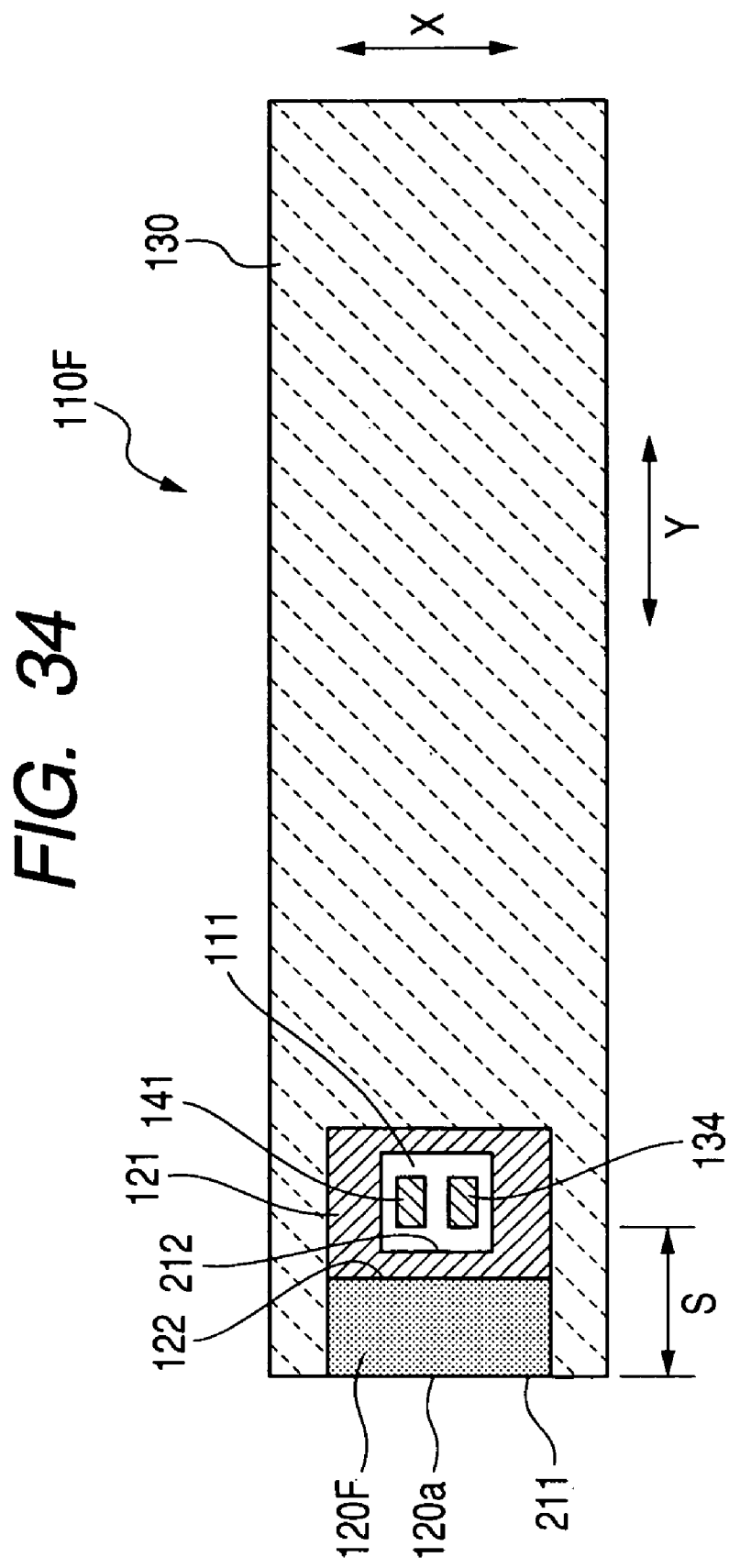
FIG. 34 is a cross sectional view of the gas sensing element taken on line N-N of FIGS. 32 and 33.

As will be apparent from FIGS. 33 and 34, further, the measuring electrode 134 of the sensor cell 135 and the inner monitor electrode 141 of the oxygen monitor cell 140 are formed on the first solid electrolyte body 151 to be spaced apart from each other in the widthwise direction X in parallel to each other.

The gas sensing element 110E of the present modified form has the same other structure as that of the gas sensing element 110 of the first modified form.

In normal practice, the sensor cell 135 is provided on the gas sensing element 110F in an area close proximity to the distal end thereof. Therefore, providing 110F diffusion resistance portion 120F on the distal end of the gas sensing element 20F along the longitudinal direction Y thereof makes it possible to adequately minimize the distance S between the external end wall of the delusion resistance portion 120F, i.e., the inlet port for measuring gasses, and the measuring electrode 134.

As set forth above, further, placing the measuring electrode 134 and the inner monitor electrode 141 along the widthwise direction X in parallel to each other allows the measuring electrode 134 and the inner monitor electrode 141 to be spaced from the external end wall 120a of the diffusion resistance portion 120F by an equaled distance. Thus, the oxygen concentration, detected with the oxygen monitor cell 140, and the oxygen concentration in measuring gases actually held in the measuring electrodes 134 can be equal to each other. This results in a capability of detecting the specified gas concentration (NOx concentration) of measuring gases with improved precision.

The gas sensing element 110F of the present modified form has the same other structure as that of the gas sensing element 110 of the first modified form.

[Gas Sensing Element of Eighth Modified Form]

Figure 35:
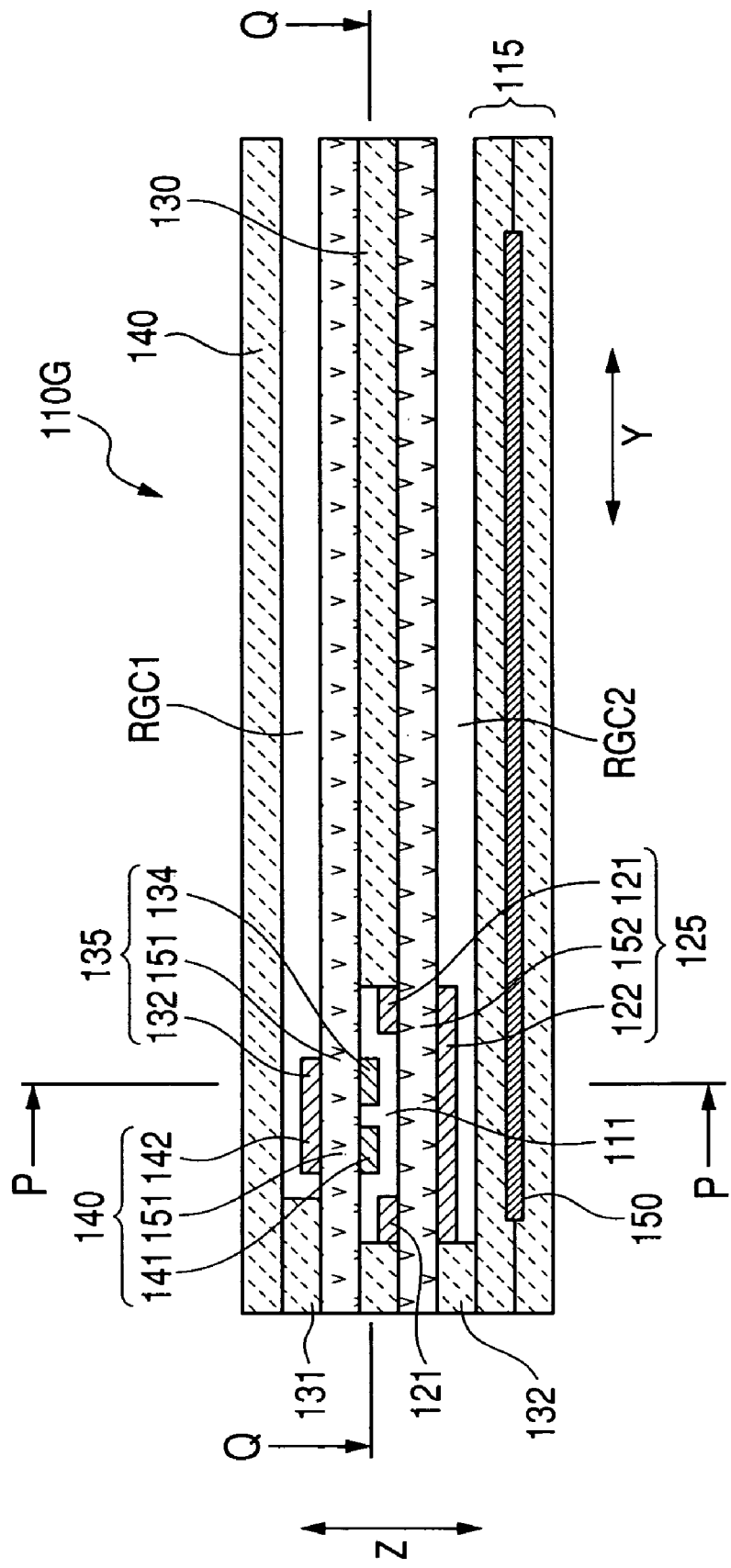
FIG. 35 is a cross sectional view showing a gas sensing element of an eighth modified form of the gas sensing element shown in FIG. 1.
Figure 36:
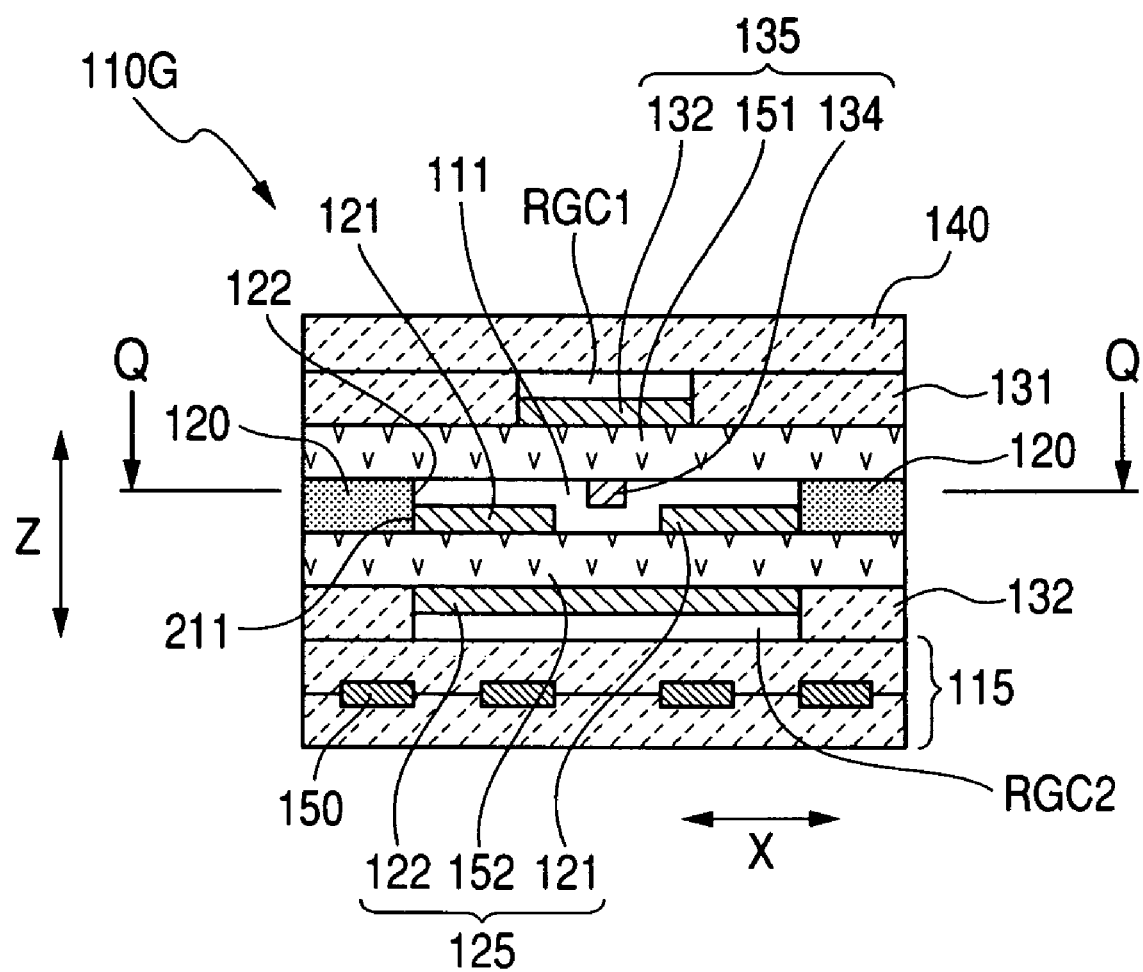
FIG. 36 is a cross sectional view of the gas sensing element taken on line P-P of FIG. 35.

A gas sensing element 110G of an eighth modified form will be described below in detail with reference to FIGS. 35 to 37 with like component parts bearing the same reference numerals as those of the gas sensing element 110 of the first modified form mentioned above.

The gas sensing element 110G of the present modified form differs from the gas sensing elements 110 of the first modified form in that the inner pump electrodes 121 are placed in areas inward of the diffusion resistance portions 120.

That is, the diffusion resistance portions 120 and the inner pump electrodes 121 are not overlapped in the stack direction Z. In addition, the inner end walls 122 of the diffusion resistance portion 120 and the external end walls 211 of the inner pump electrode 121 are held in abutting contact with each other in the widthwise direction X.

The gas sensing element 110F of the present modified form has the same other structure as that of the gas sensing element 110 of the first modified form.

With the gas sensing element 110G of the present modified form, measuring gases, reliably passed across the diffusion resistance portions 120, can be brought into contact with the inner pump electrode 121, thereby enabling the oxygen pump cell 125 to achieve a control of oxygen pumping capacity in a further reliable manner.

Thus, it becomes possible to obtain the gas sensing element 110G with excellent measuring precision.

The gas sensing element 110G of the present modification performs the same operation as that of the gas sensing element 110 of the first modified form and, hence, detailed description of the same is herein omitted.

While the specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present inventions which is to be given the full breadth of the following claims and all equivalents thereof.

What is claimed is:

1. A gas sensor control device connected to a gas sensor, including a gas sensing element composed of a solid electrolyte body and a pair of electrodes formed on the solid electrolyte body, in which an element current occurs depending on a concentration of a specified component in measuring gases upon receipt of a voltage applied across the pair of electrodes, the gas sensor control device comprising:

a current-voltage converter having one terminal connected to one electrode of the pair of electrodes for measuring the element current flowing therethrough;

an output circuit for outputting a measured result in response to the element current, measured with the current-voltage converter, as an element current measured value;

an applied voltage setting circuit connected to the other terminal of the current-voltage converter to set an applied voltage to be applied across the pair of electrodes of the sensing element;

a first electric pathway connected between the output circuit and the applied voltage setting circuit to apply the element current measured value thereto;

a second electric pathway, connected between the one terminal of the current-voltage converter and the applied voltage setting circuit, in which no element current flows;

switch means provided in the second electric pathway for selectively opening and closing the second electric pathway; and calculating means for calculating the concentration of the specified component based on the element current measured value output from the output circuit in the presence of the voltage applied from the applied voltage setting circuit;

wherein actuating the switch means allows the applied voltage setting circuit to set the applied voltage at a regulated level such that a potential difference between both terminals of the current-voltage converter lies at a predetermined specified value.

2. The gas sensor control device according to claim 1, wherein:
the output acquiring means allows the switch means to be closed to zero the potential difference between the both terminals of the current-voltage converter to acquire the output value of the output circuit under a condition where the potential difference remains zeroed.

3. The gas sensor control device according to claim 2, wherein:
the first electric pathway includes a first feedback pathway, through which the output of the output circuit is input in feedback to the applied voltage setting circuit, and the second electric pathway includes a second feedback pathway, through which a voltage appearing at the sensor-side terminal of the current-voltage converter is input in feedback to the applied voltage setting circuit;
wherein the switch means is provided in the second feedback pathway;
whereby during normal concentration detecting operation, the first feedback pathway is brought into a conducting state to allow the applied voltage setting circuit to set the applied voltage depending on the output of the output circuit input in feedback via the first feedback pathway;
whereas during an operation to calculate the current correcting value for correcting the element current, only the second feedback pathway is brought into a conducting state to allow the applied voltage setting circuit to set the applied voltage depending on a sensor-side terminal voltage of the current-voltage converter input in feedback via the second feedback pathway.

4. The gas sensor control device according to claim 2, further comprising:
means for causing the applied voltage of the applied voltage setting circuit to be regulated to voltages inducing a plurality of potential differences with respect to a sensor-side terminal voltage of the current-voltage converter when the switch means is brought into a closed state so as to acquire an output value from the output circuit under a plurality of states with the voltages being regulated; and
wherein the correcting value calculating means calculates a gain correcting value as the current correcting value in response to the output value of the output circuit acquired under the plurality of states.

5. The gas sensor control device according to claim 2, wherein:
the gas sensing element of the gas sensor includes the solid electrolyte body and first and second cells, exposed to a gas chamber, each of which is composed of a pair of electrodes formed on the solid electrolyte body, the first cell regulating an oxygen quantity of measuring gases, admitted to the measuring gas chamber, to a given concentration level and the second cell detecting a specified component of the measuring gases with the oxygen quantity being regulated with the first cell; and
the current-voltage converter measures a second cell current caused in the second cell to provide a second cell current measured value based on which a concentration of the specified component is calculated.

6. The gas sensor control device according to claim 2, further comprising:
failure determining means for determining a failure occurring in at least one of the sensing element and a sensor circuit based on a current correcting value for correcting the element current resulting from the correcting value calculating means.

7. The gas sensor control device according to claim 1, further comprising:
electromotive force detecting means operative to cause the switch means to be closed to allow a potential difference between both terminals of the current-voltage converter to be brought into a zeroed state for detecting an electromotive force occurring in the sensing element under the zeroed state; and
failure determining means for executing a failure determination of at least one of the sensing element and a sensor circuit, connected thereto, based on the electromotive force detected with the electromotive force detecting means.

8. The gas sensor control device according to claim 7, wherein:
inputting a sensor-side terminal voltage of the current-voltage converter to the applied voltage setting circuit in a feedback loop such that the set voltage set by the applied voltage setting circuit becomes equal to the sensor-side terminal voltage;
whereby the potential difference between the both terminals of the current-voltage converter is zeroed.

9. The gas sensor control device according to claim 7, wherein:
the first electric pathway includes a first feedback pathway causing the output of the output circuit to be input to the applied voltage setting circuit in a feedback loop and the second electric pathway includes a second feedback pathway causing the voltage at the sensor-side terminal of the current-voltage converter to be input to the applied voltage setting circuit in a feedback loop;
wherein the switch means is provided in the second feedback pathway;
wherein during a normal concentration detecting operation, only the first feedback pathway is brought into a conductive state to allow the applied voltage setting circuit to set the applied voltage depending on the output of the output circuit input thereto via the first feedback pathway in feedback loop; and
whereas during an operation to detect the electromotive force, only the second feedback pathway is brought into a conductive state to allow the applied voltage setting circuit to set the applied voltage depending on the sensor-side terminal voltage of the current-voltage converter input via the second feedback pathway in a feedback loop such that the potential difference between the both terminals of the current-voltage converter is zeroed.

10. The gas sensor control device according to claim 7, further comprising:
voltage application interrupting means for interrupting the application of the set voltage to the sensing means when the failure determining means determines that a failure is present.

11. The gas sensor control device according to claim 7, wherein:
the gas sensing element of the gas sensor includes the solid electrolyte body and first and second cells, exposed to a gas chamber, each of which is composed of a pair of electrodes formed on the solid electrolyte body, the first cell regulating an oxygen quantity of measuring gases, admitted to the measuring gas chamber, to a given concentration level and the second cell detecting a specified component of the measuring gases with the oxygen quantity being regulated with the first cell; and
wherein the current-voltage converter measures the element current occurring in the second cell.

12. The gas sensor control device according to claim 11, wherein:
the electromotive force detecting means executes the electromotive force detection subjected to the presence in which an oxygen concentration in the measuring gas chamber lies at a low oxygen level representing the given concentration level.

13. The gas sensor control device according to claim 2, wherein:
the gas sensing element includes the solid electrolyte body, having one surface exposed to a reference gas compartment and the other surface exposed to a measuring gas chamber, first and second cells including pairs of electrodes formed on the solid electrolyte body at one end portion thereof in face-to-face relation to the reference gas chamber and the measuring gas chamber, respectively, and a diffusion resistance portion formed on the other surface of the solid electrolyte body in an area adjacent to the measuring gas chamber to admit measuring gases therein;
wherein the first cell is operative to regulate an oxygen quantity of measuring gases, admitted to file measuring gas chamber, to a given concentration level and the second cell is operative to detect a specified component of the measuring gases with the oxygen quantity being regulated with the first cell.

14. The gas sensor control device according to claim 2, wherein:
the gas sensing element includes first and second solid electrolyte bodies, each having one surface exposed to a reference gas compartment and the other surface exposed to a measuring gas chamber, a first cell including a first pair of electrodes formed on one end portion of the first solid electrolyte body in face-to-face relation to the reference gas compartment and the measuring gas chamber, respectively, and a second pair of electrodes formed on the one end portion of the second solid electrolyte body in face-to-face relation to the reference gas compartment and the measuring gas chamber, respectively, and a diffusion resistance portion interposed between the first and second solid electrolyte bodies in an area adjacent to the measuring gas chamber to admit measuring gases therein;
wherein the first cell is operative to regulate an oxygen quantity of measuring gases, admitted to the measuring gas chamber, to a given concentration level, and the second cell is operative to pump the measuring gases to the measuring gas chamber.

15. The gas sensor control device according to claim 14, wherein:
the first cell includes a reference electrode formed on the first solid electrolyte body on the one surface thereof to be exposed to the reference gas compartment and a measuring electrode formed on the other surface of the first solid electrolyte body to be exposed to the measuring gas chamber; and
the second cell includes a reference electrode formed on the second solid electrolyte body on the one surface thereof to be exposed to the reference gas compartment and an inner pump electrode formed on the other surface of the second solid electrolyte body in face-to-face relation to the measuring gas chamber.

16. The gas sensor control device according to claim 3, wherein:
the gas sensing element has a gas diffusing range frequency above which the gas sensing element has a gas diffusion capability to enable the measuring gases to be admitted to an inside of the gas sensing element; and
the element current is zeroed during a time interval less than the gas diffusion enabling frequency range.

17. The gas sensor control device according to claim 3, wherein:
the element current lies at a value of 4 nA/ppm or less.

* * * * *